United States Patent
McWhirter et al.

(10) Patent No.: US 10,143,186 B2
(45) Date of Patent: *Dec. 4, 2018

(54) COMMON LIGHT CHAIN MOUSE

(75) Inventors: John McWhirter, Tarrytown, NY (US);
Lynn Macdonald, Harrison, NY (US);
Sean Stevens, Del Mar, CA (US);
David R. Buckler, Sleepy Hollow, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/022,759

(22) Filed: Feb. 8, 2011

(65) Prior Publication Data

US 2011/0195454 A1    Aug. 11, 2011

Related U.S. Application Data

(60) Provisional application No. 61/302,282, filed on Feb. 8, 2010.

(51) Int. Cl.
| | |
|---|---|
| A01K 67/027 | (2006.01) |
| C07K 16/46 | (2006.01) |
| C07K 16/00 | (2006.01) |
| C07K 16/28 | (2006.01) |
| C12N 15/85 | (2006.01) |
| C12N 15/90 | (2006.01) |
| C07K 16/22 | (2006.01) |

(52) U.S. Cl.
CPC .......... *A01K 67/0278* (2013.01); *C07K 16/00* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 16/22* (2013.01); *C07K 2317/21* (2013.01); *C07K 2317/24* (2013.01); *C07K 2317/515* (2013.01); *C07K 2317/565* (2013.01); *C07K 2317/567* (2013.01); *C07K 2317/76* (2013.01); *C07K 2317/92* (2013.01); *C07K 2319/30* (2013.01); *C12N 2800/204* (2013.01)

(58) Field of Classification Search
CPC .......... A01K 67/0278; A01K 2217/072; A01K 2227/105; A01K 2217/15; A01K 2267/01; C07K 16/00; C07K 2317/515; C07K 2317/24; C12N 15/8509
USPC ................................ 800/18, 21, 6
See application file for complete search history.

(56) References Cited

U.S. PATENT DOCUMENTS

| | | |
|---|---|---|
| 5,545,807 A | 8/1996 | Surani et al. |
| 5,574,205 A | 11/1996 | Kucherlapati et al. |
| 5,667,988 A | 9/1997 | Barbas et al. |
| 5,770,429 A | 6/1998 | Lonberg et al. |
| 5,789,208 A | 8/1998 | Sharon |
| 5,888,789 A | 3/1999 | Rodriguez |
| 5,939,598 A | 8/1999 | Kucherlapati et al. |
| 6,075,181 A | 6/2000 | Kucherlapati et al. |
| 6,080,560 A | 6/2000 | Russell et al. |
| 6,096,551 A | 8/2000 | Barbas et al. |
| 6,114,598 A | 9/2000 | Kucherlapati et al. |
| 6,139,835 A | 10/2000 | Kucherlapati et al. |
| 6,150,584 A | 11/2000 | Kucherlapati et al. |
| 6,162,963 A | 12/2000 | Kucherlapati et al. |
| 6,514,752 B1 | 2/2003 | Kucherlapati et al. |
| 6,551,592 B2 | 4/2003 | Lindhofer et al. |
| 6,596,541 B2 * | 7/2003 | Murphy et al. ............... 435/463 |
| 6,657,103 B1 | 12/2003 | Kucherlapati et al. |
| 6,673,986 B1 | 1/2004 | Kucherlapati et al. |
| 6,713,610 B1 | 3/2004 | Kucherlapati et al. |
| 6,914,128 B1 | 7/2005 | Salfeld et al. |
| 6,998,514 B2 | 2/2006 | Bruggemann |
| 7,052,873 B2 | 5/2006 | Tsuchiya |

(Continued)

FOREIGN PATENT DOCUMENTS

| | | |
|---|---|---|
| CN | 1199422 A | 11/1998 |
| CN | 1277632 A | 12/2000 |

(Continued)

OTHER PUBLICATIONS

Mendez et al. (1997) Nat. Genetics, vol. 15, 146-156.*

(Continued)

*Primary Examiner* — Anne Marie S Wehbe

(74) *Attorney, Agent, or Firm* — Choate, Hall & Stewart, LLP; Brenda Herschbach Jarrell; Stephanie L. Schonewald

(57) ABSTRACT

A genetically modified mouse is provided, wherein the mouse is incapable of rearranging and expressing an endogenous mouse immunoglobulin light chain variable sequence, wherein the mouse expresses only one or two human light chain variable domains encoded by human immunoglobulin sequences operably linked to the mouse kappa (κ) constant gene at the endogenous mouse κ locus, wherein the mouse expresses a reverse chimeric antibody having a light chain variable domain derived from one of only two human light chain variable region gene segments and a mouse κ constant domain, and a human heavy chain variable domain and a mouse heavy chain constant domain, from an endogenous mouse heavy chain locus. Bispecific epitope-binding proteins that are fully human are provided, comprising two different heavy chains that associate with an identical light chain that comprises a variable domain derived from one of two different human light chain variable region gene segments.

28 Claims, 3 Drawing Sheets

Specification includes a Sequence Listing.

(56) References Cited

U.S. PATENT DOCUMENTS

| | | |
|---|---|---|
| 7,064,244 B2 | 6/2006 | Jakobovits et al. |
| 7,067,284 B1 | 6/2006 | Barbas et al. |
| 7,084,260 B1 | 8/2006 | Lonberg et al. |
| 7,105,348 B2 | 9/2006 | Murphy et al. |
| 7,119,248 B1 | 10/2006 | Rajewsky et al. |
| 7,129,084 B2 | 10/2006 | Buelow et al. |
| 7,183,076 B2 | 2/2007 | Arathoon et al. |
| 7,262,028 B2 | 8/2007 | Van Berkel et al. |
| 7,435,871 B2 | 10/2008 | Green et al. |
| 7,501,552 B2 | 3/2009 | Lonberg et al. |
| 7,534,604 B2 | 5/2009 | Fandl et al. |
| 7,585,668 B2 | 9/2009 | Buelow et al. |
| 7,605,237 B2 | 10/2009 | Stevens et al. |
| 7,642,228 B2 | 1/2010 | Carter et al. |
| 7,704,498 B2 | 4/2010 | Gerritsen et al. |
| 7,879,985 B2 | 2/2011 | Urso et al. |
| 7,910,798 B2 | 3/2011 | Tanamachi et al. |
| 8,158,419 B2 | 4/2012 | Lonberg et al. |
| 8,502,018 B2 | 8/2013 | Murphy et al. |
| 8,592,562 B2 | 11/2013 | Kannan et al. |
| 8,642,835 B2 | 2/2014 | MacDonald et al. |
| 9,248,182 B2 | 2/2016 | De Kruif et al. |
| 2002/0088016 A1 | 7/2002 | Bruggemann |
| 2003/0017534 A1 | 1/2003 | Buelow et al. |
| 2003/0078385 A1 | 4/2003 | Arathoon et al. |
| 2003/0108925 A1 | 6/2003 | Dix et al. |
| 2003/0138440 A1 | 7/2003 | Fang et al. |
| 2003/0217373 A1 | 11/2003 | Green et al. |
| 2004/0015880 A1 | 1/2004 | Floyd et al. |
| 2004/0018626 A1 | 1/2004 | Murphy et al. |
| 2004/0052773 A1 | 3/2004 | Bogen et al. |
| 2004/0146991 A1 | 7/2004 | Tsuji et al. |
| 2005/0059082 A1 | 3/2005 | Breitling et al. |
| 2005/0153392 A1 | 7/2005 | Buelow et al. |
| 2005/0170398 A1 | 8/2005 | Van Berkel et al. |
| 2005/0229263 A1 | 10/2005 | Buelow |
| 2006/0015949 A1 | 1/2006 | Lonberg et al. |
| 2006/0015957 A1* | 1/2006 | Lonberg et al. ............... 800/18 |
| 2006/0021074 A1 | 1/2006 | Kellermann et al. |
| 2006/0026696 A1 | 2/2006 | Buelow et al. |
| 2006/0083747 A1 | 4/2006 | Winter et al. |
| 2006/0099207 A1 | 5/2006 | Wu et al. |
| 2006/0117398 A1 | 6/2006 | Buelow et al. |
| 2006/0153826 A1 | 7/2006 | Arnould et al. |
| 2006/0199204 A1 | 9/2006 | Dix et al. |
| 2007/0009957 A1 | 1/2007 | Bowdish et al. |
| 2007/0280945 A1 | 12/2007 | Stevens et al. |
| 2008/0069822 A1* | 3/2008 | Jensen et al. ............... 424/159.1 |
| 2009/0083879 A1 | 3/2009 | Dhugga |
| 2009/0092582 A1 | 4/2009 | Bogin et al. |
| 2009/0093059 A1 | 4/2009 | Baszczynski et al. |
| 2009/0181855 A1 | 7/2009 | Vasquez et al. |
| 2009/0258392 A1 | 10/2009 | Gallo et al. |
| 2010/0069614 A1 | 3/2010 | Houtzager et al. |
| 2010/0146647 A1* | 6/2010 | Logtenberg et al. ............... 800/4 |
| 2010/0286374 A1 | 11/2010 | Kannan et al. |
| 2010/0310586 A1* | 12/2010 | Dolcetti et al. ............... 424/184.1 |
| 2010/0331527 A1* | 12/2010 | Davis et al. ............... 530/387.3 |
| 2011/0195454 A1 | 8/2011 | McWhirter et al. |
| 2012/0021409 A1 | 1/2012 | McWhirter et al. |
| 2012/0070861 A1 | 3/2012 | Macdonald et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0222140 A1 | 8/2012 | Kuroiwa et al. |
| 2013/0045492 A1 | 2/2013 | Babb et al. |
| 2013/0096020 A1 | 4/2013 | Throsby et al. |
| 2013/0096287 A1 | 4/2013 | Macdonald et al. |
| 2013/0145484 A1 | 6/2013 | Logtenberg et al. |
| 2013/0185821 A1 | 7/2013 | Babb et al. |
| 2013/0198879 A1 | 8/2013 | McWhirter et al. |
| 2013/0198880 A1 | 8/2013 | Babb et al. |
| 2013/0302836 A1 | 11/2013 | McWhirter et al. |
| 2014/0322756 A1 | 10/2014 | Arathoon et al. |
| 2015/0059009 A1 | 2/2015 | McWhirter et al. |
| 2015/0313193 A1 | 11/2015 | McWhirter et al. |
| 2016/0219847 A1 | 8/2016 | McWhirter et al. |
| 2016/0238600 A1 | 8/2016 | Hoogenboom et al. |

FOREIGN PATENT DOCUMENTS

| | | |
|---|---|---|
| CN | 1484707 A | 3/2004 |
| CN | 1560081 A | 1/2005 |
| CN | 1671416 A | 9/2005 |
| CN | 1675245 A | 9/2005 |
| CN | 101688228 A | 3/2010 |
| CN | 101962408 A | 2/2011 |
| CN | 102123582 A | 7/2011 |
| EP | 0364096 A2 | 4/1990 |
| EP | 1298207 A1 | 4/2003 |
| EP | 1 439 234 A1 | 7/2004 |
| EP | 1505148 B1 | 4/2009 |
| EP | 1605058 B1 | 5/2009 |
| EP | 2 147 594 A1 | 1/2010 |
| EP | 2 427 357 | 3/2012 |
| EP | 2 501 817 | 9/2012 |
| EP | 2 505 654 A1 | 10/2012 |
| EP | 2 517 556 A2 | 10/2012 |
| EP | 2 517 557 A2 | 10/2012 |
| EP | 2 556 747 A2 | 2/2013 |
| EP | 2 564 695 A1 | 3/2013 |
| EP | 2 582 230 | 4/2013 |
| JP | 2006-515503 A | 6/2006 |
| JP | 2007-054076 A | 3/2007 |
| RU | 2262511 C2 | 10/2005 |
| RU | 2434882 C2 | 11/2011 |
| WO | WO-90/04036 A1 | 4/1990 |
| WO | WO-91/00906 A1 | 1/1991 |
| WO | WO-91/08216 A1 | 6/1991 |
| WO | WO-92/03918 A1 | 3/1992 |
| WO | 1994/002602 A1 | 2/1994 |
| WO | WO-94/04690 A1 | 3/1994 |
| WO | WO-94/25585 A1 | 11/1994 |
| WO | WO-95/17085 A1 | 6/1995 |
| WO | WO-95/17500 A1 | 6/1995 |
| WO | WO-97/13852 A1 | 4/1997 |
| WO | WO-97/42313 A1 | 11/1997 |
| WO | WO 98/24893 A2 | 6/1998 |
| WO | WO-98/39416 A1 | 9/1998 |
| WO | WO-98/46645 A2 | 10/1998 |
| WO | 1998/050431 A2 | 11/1998 |
| WO | WO-1999/018212 A1 | 4/1999 |
| WO | WO-99/45962 A1 | 9/1999 |
| WO | WO-00/63403 A2 | 10/2000 |
| WO | WO-01/64929 A1 | 9/2001 |
| WO | WO-02/08409 A2 | 1/2002 |
| WO | WO-02/12437 A2 | 2/2002 |
| WO | WO-02/18948 A2 | 3/2002 |
| WO | 02/036789 A2 | 5/2002 |
| WO | WO-02/053596 A2 | 7/2002 |
| WO | WO-2002/066630 A1 | 8/2002 |
| WO | WO-02/085944 A2 | 10/2002 |
| WO | WO-02/085945 A2 | 10/2002 |
| WO | WO-03/002609 A2 | 1/2003 |
| WO | WO-03/052416 A2 | 6/2003 |
| WO | WO-03/061363 A2 | 7/2003 |
| WO | WO-03/106495 A2 | 12/2003 |
| WO | 2004/009618 A2 | 1/2004 |
| WO | WO-2004/006955 A1 | 1/2004 |
| WO | WO-2004/049794 A2 | 6/2004 |
| WO | WO-2004/050838 A2 | 6/2004 |
| WO | WO-2004/058820 A2 | 7/2004 |
| WO | WO-2004/106375 A1 | 12/2004 |
| WO | WO-2005/019463 A1 | 3/2005 |
| WO | WO-2005/038001 A2 | 4/2005 |
| WO | WO-2006/117699 A2 | 11/2006 |
| WO | WO-2006/122442 A1 | 11/2006 |
| WO | WO-2007/096779 A2 | 8/2007 |
| WO | WO-2007/117410 A2 | 10/2007 |
| WO | WO-2008/022391 A1 | 2/2008 |
| WO | WO-2008/054606 A2 | 5/2008 |
| WO | WO-2008/076379 A2 | 6/2008 |
| WO | WO-2008/081197 A1 | 7/2008 |
| WO | WO-2008/112922 A2 | 9/2008 |

(56) References Cited

FOREIGN PATENT DOCUMENTS

| | | |
|---|---|---|
| WO | WO-2008/151081 A1 | 12/2008 |
| WO | WO-2009/013620 A2 | 1/2009 |
| WO | WO-2009/051974 A1 | 4/2009 |
| WO | WO-2009/089004 A1 | 7/2009 |
| WO | WO-2009/097006 A2 | 8/2009 |
| WO | WO-2009/129247 A2 | 10/2009 |
| WO | WO-2009/143472 A2 | 11/2009 |
| WO | 2009157771 | 12/2009 |
| WO | WO-2010/039900 A2 | 4/2010 |
| WO | WO-2010/053751 A1 | 5/2010 |
| WO | WO-2010/054007 A1 | 5/2010 |
| WO | WO-2010/070263 A1 | 6/2010 |
| WO | WO-2010/097385 A1 | 9/2010 |
| WO | 2010/128897 A1 | 11/2010 |
| WO | WO-2010/136598 A1 | 12/2010 |
| WO | WO-2010/151792 A1 | 12/2010 |
| WO | 2011004192 A1 | 1/2011 |
| WO | WO-2011/062207 A1 | 5/2011 |
| WO | 2011/072204 A1 | 6/2011 |
| WO | 2011/097603 A1 | 8/2011 |
| WO | 2011097603 A1 | 8/2011 |
| WO | WO-2011/143545 A1 | 11/2011 |
| WO | 2011/158009 A1 | 12/2011 |
| WO | WO-2011/163311 A1 | 12/2011 |
| WO | WO-2011/163314 A1 | 12/2011 |
| WO | WO-2012/018764 A1 | 2/2012 |
| WO | 2012/141798 A1 | 10/2012 |
| WO | 2012/148873 A2 | 11/2012 |
| WO | 2013022782 A1 | 2/2013 |
| WO | WO-2013/059230 A1 | 4/2013 |
| WO | WO-2013/079953 A1 | 6/2013 |
| WO | WO-2013/134263 A1 | 9/2013 |
| WO | WO-2013/184761 A1 | 12/2013 |
| WO | WO-2014/160179 A1 | 10/2014 |
| WO | WO-2014/160202 A1 | 10/2014 |

OTHER PUBLICATIONS

Sirac et al.(2006) Blood, vol. 108, 536-543.*
Aucouturier et al. (1993) J. Immunol., vol. 150(8), 3561-3568.*
Merchant et al. (1998) Nat. Biotech., vol. 16, 677-681.*
De Wildt et al. (1999) J. Mol. Biol., vol. 285, 895-901.*
V-BASE Sequence Directory http://www2.mrc-lmb.cam.ac.uk/vbase/list2.php.*
V-BASE sequence directory (1997) www2.mrc-lmb.cam.ac.uk.*
Longo et al. (2008) J. Immunol., vol. 181, 1299-1306.*
International search report for PCT application No. PCT/US2011/023971, dated Apr. 11, 2011.
Written opinion of the International Searching Authority for PCT application No. PCT/US2011/023971, dated Apr. 11, 2011.
Brezinschek H.P., et al. "Pairing of variable heavy and variable kappa chains in individual naïve and memory B cells." J. Immunol. (1998) 160(10): 4762-4767.
Carmack, C.E., et al. "Influence of a V kappa 8 L chain transgene on endogenous rearrangements and the immune response to the HA(Sb) determinant on influenza virus." J. Immunol. (1991) 147(6): 2024-2033.
Cascalho M., et al. "A quasi-monoclonal mouse." Science. (1996) 272(5268): 1649-1652.
De Wildt R.M., et al. "Analysis of heavy and light chain pairings indicates that receptor editing shapes the human antibody repertoire." J. Mol. Biol. (1999) 285(3): 895-901.
Fraenkel S., et al. "Allelic 'choice' governs somatic hypermutation in vivo at the immunoglobulin kappa-chain locus." Nat. Immunol. (2007) 8(7): 715-722.
Gay D., et al. "Receptor editing: an approach by autoreactive B cells to escape tolerance." J. Exp. Med. (1993) 177(4): 999-1008.
Green L.L., et al. "Antigen-specific human monoclonal antibodies from mice engineered with human Ig heavy and light chain YACs." Nat. Genet. (1994) 7(1): 13-21.
Green L.L., et al. "Regulation of B cell development by variable gene complexity in mice reconstituted with human immunoglobulin yeast artificial chromosomes." J. Exp. Med. (1998) 188(3): 483-495.
O'Brien R.L., et al. "Somatic hypermutation of an immunoglobulin transgene in kappa transgenic mice." Nature. (1987) 326(6111): 405-409.
Pelanda R., et al. "A prematurely expressed Ig(kappa) transgene, but not V(kappa)J(kappa) gene segment targeted into the Ig(kappa) locus, can rescue B cell development in lambda5-deficient mice." Immunity. (1996) 5(3): 229-239.
Prak E.L., et al. "Light chain replacement: a new model for antibody gene rearrangement." J. Exp. Med. (1995) 182 (2): 541-548.
Bauer, S.R., et al. "Structure and pre-B lymphocyte restricted expression of the VpreB gene in humans and conservation of its structure in other mammalian species." The EMBO Journal (1988) 7(1): 111-116.
Tsubata, T., et al. "The Products of Pre-B Cell-specific Genes(Lambda5 and VpreB) and the Immunoglobulin mu Chain Form a Comples That Is Transported onto the Cell Surface." Journal of Experimental Medicine (1990) 172: 973-976.
Leitzgen, K., et al. "Assembly of Immunoglobulin Light Chains as a Prerequisite for Secretion." Journal of Biological Chemistry (1997) 272(5): 3117-3123.
Donohoe, M.E., et al. "Transgenic Human Lambda5 Rescues the Murine Lambda5 Nullizygous Phenotype." Journal of Immunology (2000) 164: 5269-5276.
Rojas, G., et al. "Phage antibody fragments library combining a single human light chain variable region with immune mouse heavy chain variable regions." Journal of Biotechnology (2002) 94: 287-298.
Xu, L., et al. "Combinatorial surrobody libraries." Proceedings of the National Academy of Sciences USA (2008) 105 (31): 10756-10761.
De Kruif, J., et al. "Human Immunoglobulin Repertoires against Tetanus Toxoid Contain a Large and Diverse Fraction of High-Affinity Promiscuous VH Genes." Journal of Molecular Biology (2009) 387: 548-558.
Smith, B.P., et al. "The unique and immunoglobulin-like regions of surrogate light chain component lambda5 differentially interrogate immunoglobulin heavy-chain structure." Molecular Immunology (2010) 47: 1195-1206.
Arnold, L.W., et al. 1994. "Development of B-1 cells: segregation of phosphatidyl choline-specific B cells to the B-1 population occurs after immunoglobulin gene expression." J. Exp. Med. 179: 1585-1595.
Hengstschlager, M., et al. 1994. "A lambda1 transgene under the control of a heavy chain promoter and enhancer does not undergo somatic hypermutation." Eur. J. Immunol. 24: 1649-1656.
Gonzalez-Fernandez, A., and C. Milstein. 1993. "Analysis of somatic hypermutation in mouse Peyer's patches using immunoglobulin kappa light-chain transgenes." PNAS USA. 90: 9862-9866.
Jolly, C.J., et al. 1997. "Rapid methods for the analysis of immunoglobulin gene hypermutation: application to transgenic and gene targeted mice." Nucleic Acids Research. 25(10): 1913-1919.
Goyenechea, B., and C. Milstein. 1996. "Modifying the sequence of an immunoglobulin V-gene alters the resulting pattern of hypermutation." PNAS USA. 93: 13979-13984.
Klotz, E.L., et al. 1998. "Somatic hypermutation of an artificial test substrate within an Ig kappa transgene." J. Immunol. 161: 782-790.
Klotz, E.L., and U. Storb. 1996. "Somatic hypermutation of a lambda2 transgene under the control of the lambda enhancer or the heavy chain intron enhancer." J. Immunol. 157: 4458-4463.
Kong, Q., et al. 1998. "A lambda 3' enhancer drives active and untemplated somatic hypermutation of a lambda1 transgene." J. Immunol. 161: 294-301.
Sirac, C., et al. 2006. "Role of the monoclonal kappa chain V domain and reversibility of renal damage in a transgenic model of acquired Fanconi syndrome." Blood. 108(2): 536-543.
Aucouturier, P., et al. 1993. "Monoclonal Ig L chain and L chain V domain fragment crystallization in myeloma-associated Fanconi's syndrome." J. Immunol. 150(8 Pt. 1): 3561-3568.

(56) References Cited

OTHER PUBLICATIONS

Storb, et al., "Transgenic Mice with μ and κ Genes Encoding Antiphosphorycholine Antibodies", J. Exp Med, 164:627-641 (Aug. 1986).
Request to provoke an interference U.S. Appl. No. 13/750,753, filed Jan. 25, 2013.
International Search Report and Written Opinion for PCT Application No. PCT/US2013/029125 dated Jun. 20, 2013.
Carter, P., "Bispecific human IgG by design," Journal of Immunological Methods, vol. 248, No. 1-2, pp. 7-15 (2001).
Davies, et al., "Creation of Mice Expressing Human Antibody Light Chains by Introduction of a Yeast Artificial Chromosome Containing the Core Region of the Human Immunoglobulin κ Locus", Nature Biotechnology 11:911-914, (1993).
Desienhofer, J., "Crystallographic Refinement and Atomic Models of a Human Fc Fragment and Its Complex with Fragment B of Protein A from *Staphylococcus aureus* at 2.9- and 2.8-Å Resolution," Biochemistry, vol. 20, No. 9, pp. 2361-2370 (1981).
Edwards, D.R., et al., "The ADAM Metalloproteinases", Molecular Aspects of Medicine, 29(5): 258-289 (2008).
Featherstone, K., et al., "The Mouse Immunoglobulin Heavy Chain V-D Intergenic Sequence Contains Insulators That May Regulate Ordered V(D)J Recombination", The Journal of Biological Chemistry, 285(13):9327-9338 (2010).
Goletz et al., "Selection of Large Diversities of Antiidiotypic Antibody Fragments by Phage Display", J. Mol. Biol. 315:1087-97, (2002).
Han, C., et al., "Comprehensive Analysis of Reproductive ADAMs: Relationship of ADAM4 and ADAM6; with an ADAM Complex Required for Fertilization in Mice", Biology of Reproduction, 80(5): 1001-1008 (2009).
Hochedlinger, et al., "Monoclonal Mice Generated by Nuclear Transfer from Mature B and T Donor Cells", Nature 415 (6875):1035-1038, (2002).
Jakobovits, A. et al., "From XenoMouse technology to panitumumab, the first fully human antibody product from transgenic mice," Nature Biotechnology, vol. 25, No. 10, pp. 1134-1143 (2007).
Lefranc, M., "Nomenclature of the Human Immunoglobulin Genes," Current Protocols in Immunology, Supplement 40, pp. A.1P.1-A.1P.37 (2001).
Lindhofer, H. et al., "Preferential Species-Restricted Heavy/Light Chain Pairing in Rat/Mouse Quadromas," The Journal of Immunology, vol. 155, pp. 219-225 (1995).
Lonberg et al., "Antigen-specific Human Antibodies from Mice Comprising Four Distinct Genetic Modifications", Nature 368:856-859, (1994).
Marvin, J. et al., "Recombinant approaches to IgG-like bispecific antibodies," Acta Pharmacologica Sinica, vol. 26, No. 6, pp. 649-658 (2005).
Merchant, A. et al., "An efficient route to human bispecific IgG," Nature Biotechnology, vol. 16, No. 7, pp. 677-681 (1998).
Moran, Nuala "Mouse Platforms Jostle for Slice of Humanized Antibody Market", Nature Biotech 3:267-8, 2013.
Nicholson, I. et al., "Antibody Repertoires of Four- and Five-Feature Translocus Mice Carrying Human Immunoglobulin Heavy Chain and κ and λ Light Chain Yeast Artificial Chromosomes," Journal of Immunology, vol. 163, pp. 6898-6906 (1999).
Storb, et al., "Transgenic Mice with μ And κ Genes Encoding Antiphosphorycholine Antibodies", J. Exp Med, 164:627-641.
Taylor et al., "A Transgenic Mouse that Expresses a Diversity of Human Sequence Heavy and Light Chain Immunoglobulins", Nucleic Acid Research, 20(23):6287-6295 (1992).
Taylor et al., "Human immunoglobulin transgenes undergo rearrangement, somatic mutation and class switching in mice that lack endogenous IgM", Int. Immunol. 6:579-591 (1994).
European Communication for Application No. 12 173 456.0 dated Dec. 5, 2012.
European Examination for Application No. 11 703 799.4 dated Oct. 9, 2012.
European Search Report for Application No. 12 173 456.0 dated Aug. 10, 2012.
International Search Report and Written Opinion for PCT Application No. PCT/US2012/034737 dated Dec. 6, 2012.
International Search Report for PCT/US2012/049600 (7 pages), dated Nov. 23, 2012.
Summons to attend oral proceedings arranged in connection with European patent application 09075279.1 (Publication No. EP 2 147 594 A1) dated Mar. 6, 2013.
Third Party Observations Under Article 115 EPC against European Parent Application No. 09075279.1.
Third Party Observations on European patent application 11 703 799.4-2405 (Publication No. EP 2 501 817) dated Feb. 28, 2013.
Reply to Third Party Observations on European patent application 11 703 799.04 (Publication No. EP 2 501 817) filed in EPO dated May 20, 2013.
U.S. Non-Final Office Action for U.S. Appl. No. 13/093,156 dated Sep. 6, 2012.
U.S. Non-Final Office Action for U.S. Appl. No. 13/412,936 dated Sep. 6, 2012.
Giallourakis, C.C., et al., Elements between the IgH variable (V) and diversity (D) clusters influence antisense transcription and lineage-specific V(D)K recombination PNAS, 107(51):22207-22212 (2010).
Hendricks, J., et al., "Organization of the variable region of the immunoglobin heavy-chain gene locus of the rat," Immunogenetics, 62:479-486 (2010).
Kim, T. et al., "Expression and relationship of mail reproductive ADAMs in mouse," Biology of Reproduction, 74:744-750 (2006).
Lonberg, N., "Human antibodies from transgenic animals," Nature Biotechnology, 23(9):1117-1125 (2005).
Seals, D.F., et al., "the ADAMs family of metalloproteases: multidomain; proteins with multiple functions," Genes and Development, 17(1):7-30 (2003).
International Search Report and Written Opinion dated Sep. 4, 2013, from related International Patent Application No. PCT/US2013/044257 filed Jun. 5, 2013.
After Final Consideration Pilot Program Request as filed in U.S. Appl. No. 13/798,310 on Jul. 18, 2014 (2 pages).
Choi et al., Characterization and comparative genomic analysis of intronless Adams with testicular gene expression: Apr. 2004; Genomics 83(4): 636-646.
Declaration Appendix as filed in U.S. Appl. No. 13/798,310 on Jul. 18, 2014 (7 pages).
Declaration under 37 CFR 1.131 as filed in U.S. Appl. No. 13/798,310 on Jul. 18, 2014 (21 pages).
Exhibit A as filed in U.S. Appl. No. 13/798,310 on Jul. 18, 2014 (2 pages).
Exhibit B as filed in U.S. Appl. No. 13/798,310 on Jul. 18, 2014 (2 pages).
Exhibit C as filed in U.S. Appl. No. 13/798,310 on Jul. 18, 2014 (1 page).
Exhibit D as filed in U.S. Appl. No. 13/798,310 on Jul. 18, 2014 (1 page).
Exhibit E as filed in U.S. Appl. No. 13/798,310 on Jul. 18, 2014 (3 pages).
Goodhardt et al., Rearrangement and Expression of rabbit immunoglobulin K light chain gene in transgenic mice; Jun. 1987; PNAS, 84: 4229-4233.
International Search Report for PCT/US2014/025982 dated Jul. 22, 2014 (6 pages).
International Search Report for PCT/US2014/026040 dated Jul. 29, 2014 (5 pages).
Janeway's Immunobiology, Seventh Edition, Murphy, Travers and Walpot, eds., Garland Science, New York and London, Ch. 4, pp. 145-155 (2008).
Kaushik et al, "Stochastic pairing of heavy-chain and κ light-chain variable gene families occurs in polyclonally activated B cells," Proc. Natl. Acad. Sci. USA, vol. 87: 4932-4936 (1990).
Nagle (2007) Regeneron helps make Sanofi VelocImmune to its "weak pipeline", <http://www.outsourcing-pharma.com>— Published Dec. 3, 2007.

(56) References Cited

OTHER PUBLICATIONS

News in Brief Article (2007) Big Pharma vies for mice, Nature Biotechnology 2007, 25(6): 613—Published Jun. 2007.
Sasaki et al., "Canonical NF-κB Activity, Dispensable for B Cell Development, Replaces BAFF-Receptor Signals and Promotes B Cell Proliferation upon Activation," Immunity 24: 729-739 (2006).
Scott, Christopher T., "Mice with a human touch," Nature Biotechnology, 25(10): 1075-1077 (2007).
U.S. Non-Final Office Action for U.S. Appl. No. 13/412,936 (dated Sep. 6, 2012).
Written Opinion for PCT/US2012/034737, (dated Dec. 6, 2012).
Written Opinion for PCT/US2012/049600 (8 pages), dated Nov. 23, 2012.
Written Opinion for PCT/US2014/025982 dated Jul. 22, 2014 (7 pages).
Written Opinion for PCT/US2014/026040 dated Jul. 29, 2014 (8 pages).
Chinese Search report dated May 15, 2013, from related Chinese Patent Application No. 201180013714.0.
GenBank Accession No. ABA26122, immunoglobulin light chain variable region, partial [Homo sapiens], Rabquer et al., 2 pages, first references Dec. 31, 2005.
GenBank Accession No. M87478, Human rearranged IgK mRNA VJC region, Aucouturier et al., 1 page, first referenced Mar. 3, 1992, first seen at NCBI Apr. 27, 1993.
Goyenechea, B. et al., Cells strongly expressing Ig(kappa) transgenes show clonal recruitment of hypermutation: a role for both MAR and the enhancers, EMBO J., 16(13):3987-94 (1997).
Hömig-Hölzel, C. et al., Constitutive CD40 signaling in B cells selectively activates the noncanonical NF-kappaB pathway and promotes lymphomagenesis, J. Exp. Med., 205(6):1317-29 (2008).
Jakobovits, A., Production of fully human antibodies by transgenic mice, Curr. Opin. Biotechnol., 6(5):561-6 (1995).
Kabat, E.A., and Wu, T.T., Identical V region amino acid sequences and segments of sequences in antibodies of different specificities. Relative contributions of VH and VL genes, minigenes, and complementarity-determining regions to binding of antibody-combining sites, J. Immunol., 147(5)1 709-19 (1991).
Klöhn, P.C. et al., IBC's 23rd Annual Antibody Engineering, 10th Annual Antibody Therapeutics international conferences and the 2012 Annual Meeting of the Antibody Society: Dec. 3-6, 2012, San Diego, CA, Mabs, 5(2):178-201 (2013).
No Author Listed, Additional post-filing data and letter filed by the Applicant/Patentee for corresponding European application 09075279. 1, now opposed patent EP 2147594 B1, 4 pages (Jun. 13, 2013).
No Author Listed, Next generation transgenic mice for therapeutic human antibodies, Description of MeMoTM, filed by the Applicant/ Patentee in prosecution for corresponding European application 09075279.1, now opposed patent EP 2147594 B1, 2 pages (Dec. 22, 2011).
Orban, P.C. et al., Tissue- and site-specific DNA recombination in transgenic mice, Proc. Natl. Acad. Sci. U S A., 89(15):6861-5 (1992).
Popov, A.V. et al., A human immunoglobulin lambda locus is similarly well expressed in mice and humans, J. Exp. Med., 189(10):1611-20 (1999).
Rickert, R.C. et al., B lymphocyte-specific, Cre-mediated mutagenesis in mice, Nucleic Acids Res., 25(6):1317-8 (1997).
Sharpe, M.J. et al., Somatic hypermutation of immunoglobulin kappa may depend on sequences 3' of C kappa and occurs on passenger transgenes, EMBO J., 10(8):2139-45 (1991).
Simon, T. and Rajewsky, K., Antibody domain mutants demonstrate autonomy of the antigen binding site, EMBO J., 9(4):1051-6 (1990).
Third Party Observations under Article 115 EPC for EP 12 173 456.0, 8 pages (Nov. 3, 2014).
Al-Lazikani, B. et al., Standard conformations for the canonical structures of immunoglobulins, J. Mol. Biol., 273(4):927-48 (1997).
Arnaout, R. et al., High-resolution description of antibody heavy-chain repertoires in; humans PLoS One, 6(8):e22365 (2011).

Askew, G.R. et al., Site-directed point mutations in embryonic stem cells: a gene-targeting tag-and-exchange strategy, Mol. Cell Biol., 13(7):4115-24 (1993).
Author Not Known, Chapter 8: The Development and Survival of Lymphocytes, Janeway's Immunobiology, 8th Edition, Eds. Kenneth Murphy et al, Garland Science (ISBN: 9780815342434), whole document, in particular page 279 and Figure 8.4, (2011).
Baeuerle, P.A. and Reinhardt, C., Bispecific T-cell engaging antibodies for cancer; therapy, Cancer Res., 69(12):4941-4 (2009).
Billiard, F. et al., Ongoing Dll4-Notch signaling is required for T-cell homeostasis in the adult thymus, Eur. J. Immunol., 41(8):2207-16 (2011).
Blaas, L. et al., Bacterial artificial chromosomes improve recombinant protein production in mammalian cells, BMC Biotechnol., 9:3 (2009).
Brezinschek, H.P. et al., Analysis of the human VH gene repertoire. Differential effects of selection and somatic hypermutation on human peripheral CD5(+)/IgM+ and CD5(-)/IgM+ B; Cells, J. Clin. Invest., 99(10):2488-501 (1997).
Bruggemann, M. et al., A repertoire of monoclonal antibodies with human heavy chains from transgenic mice, Proceedings of the National of Academy of Science USA, 86:6709-6713 (1989).
Bruggemann, M., Human Antibody Expression in Transgenic Mice, Archivum Immunologiae et Therapiae Experimentalis, 49:203-208 (2001).
Brüggemann, M., Human Monoclonal Antibodies from Translocus Mice, Molecular Biology of B Cells, Eds. Honjo, T. and Neuberger, M.S., New York, NY: Academic Press, pp. 547-561 (2004).
Chothia, C. and Lesk, A.M., Canonical structures for the hypervariable regions of; Immunoglobulins, J. Mol. Biol., 196(4):901-17 (1987).
Choulika, A. et al., Induction of homologous recombination in mammalian chromosomes by using the I-Scel system of Saccharomyces cerevisiae, Mol. Cell. Biol., 15:4 1968-73 (1995).
Cohen-Tannoudji, M. et al., I-Scel-induced gene replacement at a natural locus in; embryonic stem cells, Mol. Cell. Biol., 18(3):1444-8 (1998).
Combriato, G. and Klobeck, H.G., Regulation of human Ig lambda light chain gene expression by NF-kappa B, J. Immunol., 168(3):1259-66 (2002).
Corcos, D. et al, Pre-B-cell development in the absence of lambda 5 in transgenic mice expressing a heavy-chain disease protein, Curr. Biol., 5(10):1140-8 (1995).
Cowen, N.J. et al., Purification and Sequence Analysis of the mRNA Coding for an Immunoglobulin Heavy Chain, European J. of Biochem., 61(2): 355-368 (1976).
Dechiara, T.M. et al., Chapter 16: VelociMouse: Fully ES Cell-Derived F0 Generation Mice Obtained from the Injection of ES Cells into 8-Cell Stage Embryos, Gene Knockout Protocols: Second Edition, vol. 530, Humana Press (2009).
Declaration of Andrew M. Scharenberg, M.D., filed in prosecution of U.S. Appl. No. 12/130,818, 21 pages, signed Oct. 4, 2010.
Declaration of Lynn E. Macdonald, including Annexes 1-4, as together made publicly available at least upon submission to and online publication by the European Patent Office on Mar. 12, 2015, 13 pages, signed Mar. 3, 2015.
Desmyter, A. et al., Crystal structure of a camel single-domain VH antibody fragment in complex with lysozyme, Nat. Struct. Biol., 3(9):803-11 (1996).
Donoho, G. et al., Analysis of gene targeting and intrachromosomal homologous recombination stimulated by genomic double-strand breaks in mouse embryonic stem cells, Mol. Cell. Biol., 18(7):4070-8 (1998).
Echelard, Y., Year of the ox, Nat. Biotechnol., 27(2):146-7 (2009).
Els Conrath, K. et al., Camel single-domain antibodies as modular building units in bispecific and bivalent antibody constructs, J. Biol. Chem., 276(10):7346-50 (2001).
Epinat, J.C., et al. A novel engineered meganuclease induces homologous recombination in yeast and mammalian cells, Nucleic Acids Res., 31(11):2952-62 (2003).
Ewert, S. et al., Biophysical properties of human antibody variable domains, J. Mol. Biol., 325(3):531-53 (2003).

(56) References Cited

OTHER PUBLICATIONS

Farner, N.L. et al., Molecular mechanisms and selection influence the generation of the human V lambda J lambda repertoire, J. Immunol., 162(4):2137-45 (1999).

Fell, H.P. et al., Homologous recombination in hybridoma cells: heavy chain chimeric antibody produced by gene targeting, Proc. Natl. Acad. Sci. U S A., 86(21):8507-11 (1989).

Fischer, N. and Léger, O., Bispecific antibodies: molecules that enable novel therapeutic strategies, Pathobiology, 74(1):3-14 (2007).

Gallo, M.L. et al., The human immunoglobulin loci introduced into mice: V (D) and J gene segment usage similar to that of adult humans, Eur. J. Immunol., 30(2):534-40 (2000).

GenBank Accession No. X97051, GI:564822, first referenced Jan. 9, 1997, updated Nov. 14, 2006 (29 pages).

Hagiwara, S., Transgenic expression of VpreB-3 under the control of the immunoglobulin heavy chain enhancer and SV40 promoter, Kobe J. Med. Sci., 42(1):43-59 (1996).

Harding, F.A. and Lonberg, N., Class switching in human immunoglobulin transgenic Mice, Ann. N Y Acad. Sci., 764:536-46 (1995).

Hardy, R.R and Hayakawa, K., B cell development pathways, Annu. Rev. Immunol., 19:595-621 (2001).

IMGT V-Quest Analysis of Sequence of GenBank M87478, 7 pages.

Inlay, M. et al., Essential roles of the kappa light chain intronic enhancer and 3' enhancer in kappa rearrangement and demethylation, Nat. Immunol., 3(5):463-8 (2002).

Irving, R.A. et al., Ribosome display and affinity maturation: from antibodies to single V-domains and steps towards cancer therapeutics, J. Immunol. Methods, 248(1-2):31-45 (2001).

Jendreyko, N. et al., Intradiabodies, bispecific, tetravalent antibodies for the simultaneous functional knockout of two cell surface receptors, J. Biol. Chem., 278(48):47812-9 (2003).

Knappik, A. et al., Fully synthetic human combinatorial antibody libraries (HuCAL) based on modular consensus frameworks and CDRs randomized with trinucleotides, J. Mol. Biol., 296(1):57-86 (2000).

Kuroiwa, Y. et al., Cloned transchromosomic calves producing human immunoglobulin, Nat. Biotechnol., 20(9):889-94 (2002).

Le Gall, F. et al., Effect of linker sequences between the antibody variable domains on the formation, stability and biological activity of a bispecific tandem diabody, Protein Eng. Des. Sel., 17(4):357-66 (2004).

Lee, H. et al., Human C5aR knock-in mice facilitate the production and assessment of anti-inflammatory monoclonal antibodies, Nat. Biotechnol., 24(10):1279-84 (2006).

Lefranc, M.P. and Lefranc, G., Immunoglobulin Facts Book, London: Academic Press, pp. 3-44, 98-100, and 102 (2001).

Lefranc, M.P. Nomenclature of the human immunoglobulin heavy (IGH) genes, Exp. Clin. Immunogenet., 18(2):100-16 (2001).

Lefranc, M.P., Nomenclature of the human immunoglobulin kappa (IGK) genes, Exp. Clin. Immunogenet., 18(3):161-74 (2001).

Liao, M.J. and Van Dyke, T., Critical role for ATM in suppressing V(D)J recombination-driven thymic lymphoma, Genes Dev., 13(10):1246-50 (1999).

Logtenberg, T., Antibody cocktails: next-generation biopharmaceuticals with improved potency, Trends Biotechnol., 25(9):390-4 (2007).

Lonberg, N., Human Monoclonal Antibodies from Transgenic Mice, Therapeutic Antibodies, Handbook of Experimental Pharmacology, Eds. Chernajovsky, Y and Nissim, A., Berlin Heidelberg: Springer-Verlag, 181: 69-97 (2008).

Luby, T.M. et al., The mu Switch Region Tandem Repeats Are Important, but Not Required, for Antibody Class Switch Recombination, J. Exp. Med., 193(2):159-168 (2001).

Macdonald, et al.. Velocigene Technology Extended to Humanization of Several Megabases of Complex Gene Loci., Presented at 1st International MUGEN Conference on Animal Models for Human Immunological Disease, Athens, Greece (Sep. 10-13, 2006).

Manis, J.P. et al., Mechanism and control of class-switch recombination, Trends. Immunol., 23(1):31-9 (2002).

Martinez-Jean, C. et al., Nomenclature and overview of the mouse (Mus musculus and Mus sp.) immunoglobulin kappa (IGK) genes, Exp. Clin. Immunogenet., 18(4):255-79 (2001).

Murphy, A., Veloclmmune: Immunoglobulin Variable Region Humanized Mice, Recombinant Antibodies for Immunotherapy, Ed. Little, M., New York, NY: Cambridge University Press, pp. 100-107 (2009).

Murphy, Kenneth, Janeway's Immunobiology, 8th Edition., New York: Garland Science, Chapter 5, Sections 5-1 to 5-4, pp. 157-162 (2012).

Muyldermans, S. et al., Sequence and structure of VH domain from naturally occurring camel heavy chain immunoglobulins lacking light chains, Protein Eng., 7(9):1129-35 (1994).

Muyldermans, S., Single domain camel antibodies: current status, J. Biotechnol., 74(4):277-302 (2001).

Nemazee, D., Receptor editing in lymphocyte development and central tolerance, Nat. Rev. Immunol., 6(10):728-40 (2006).

Nguyen, V.K. et al., Heavy-chain only antibodies derived from dromedary are secreted and displayed by mouse B cells, Immunology, 109(1):93-101 (2003).

Nucleotide Sequence RID Y55HBK1 W114, last accessed Aug. 6, 2014 (2 pages).

Porteus, M.H. and Carroll, D., Gene targeting using zinc finger nucleases, Nat.; Biotechnol., 23(8):967-73 (2005).

Prelle, K. et al., Pluripotent stem cells—model of embryonic development, tool for gene targeting, and basis of cell therapy, Anat. Histol. Embryol., 31(3):169-86 (2002).

Ramsden, D.A. et al., Conservation of sequence in recombination signal sequence spacers. Nucleic Acids Res., 22(10):1785-96 (1994).

Ravetch, J.V., Structure of the human immunoglobulin mu locus: characterization of embryonic and rearranged J and D genes, Cell, 27(3 Pt 2):583-91 (1981).

Reusch, et al., Beyond mAbs with TandAbs, Innovations in Pharmaceutical Technology, 4 pages (Jun. 2011).

Riechmann, L. and Muyldermans, S., Single domain antibodies: comparison of camel VH and camelised human VH domains, J. Immunol. Methods., 231(1-2):25-38 (1999).

Rodríguez, C.I., et al., High-efficiency deleter mice show that FLPe is an alternative to Cre-loxP, Nat. Genet., 25(2):139-40 (2000).

Rosner, K. et al., Third complementarity-determining region of mutated VH immunoglobulin genes contains shorter V, D, J, P, and N components than non-mutated genes, Immunology, 103(2):179-87 (2001).

Rouet, P., et al. Introduction of double-strand breaks into the genome of mouse cells by expression of a rare-cutting endonuclease, Mol. Cell. Biol., 14:12 8096-8106 (1994).

Schroeder, H.W. Jr., Similarity and divergence in the development and expression; of the mouse and human antibody repertoires, Dev. Comp. Immunol., 30(1-2):119-35 (2006).

Sekiguchi, et al. Mechanism of V(D)J Recombination, Molecular Biology of B Cells, Eds. Honjo, Alt, and Neuberger, London, UK: Elsevier Academic Press, pp. 61-82 (2004).

Shih, H.H., Discovery Process for Antibody-Based Therapeutics, Development of Antibody-Based Therapeutics 426, Eds. Tabrizi, M.A. et al., Springer New York, pp. 9-32 (2012).

Sirac, C. et al., Toward understanding renal Fanconi syndrome: step by step advances through experimental models, Contrib. Nephrol., 169:247-61 (2011).

Soriano, P., Generalized lacZ expression with the ROSA26 Cre reporter strain, Nat. Genet., 21(1):70-1 (1999).

Steipe, B., et al. Sequence statistics reliably predict stabilizing mutations in a protein domain, J. Mol. Biol., 240(3):188-92 (1994).

Stevens et al., Human Antibody Discovery, Veloclmmune—A novel platform, Pharma Focus Asia, Issue 8: 72-74 (2008).

Stevens, S. et al. Velocimmune: Humanization of Immunoglobulin Loci Using Velocigene Technology, Presented at 1st International MUGEN Conference on Animal Models for Human Immunological Disease, Athens, Greece (Sep. 10-13, 2006).

Tanha, J. et al., Optimal design features of camelized human single-domain antibody libraries, J. Biol. Chem., 276(27):24774-80 (2001).

Third Party Observations pursuant to Art. 115 EPC and R. 114 EPC against EP Application No. 12717033.0, 11 pages (May 4, 2015).

(56) References Cited

OTHER PUBLICATIONS

Third Party Observations pursuant to Article 115 EPC and R. 114 EPC against European Application No. 11703799.4, 5 pages (Apr. 10, 2015).
Tomizuka, K. et al., Double trans-chromosomic mice: maintenance of two individual human chromosome fragments containing Ig heavy and kappa loci and expression of fully human antibodies, Proc. Natl. Acad. Sci. U S A., 97(2):722-7 (2000).
Tonegawa, S., Somatic generation of antibody diversity, Nature, 302(5909):575-81 (1983).
Torres and Kuhn, Laboratory Protocols for Conditional Gene Targeting, 42-53 (1997).
UniProt Entry Q5QGZ9, retrieved Jan. 21, 2015 from <http://www.uniprot.org/Q5QGZ9> (16 pages).
Van Spriel, A.B. et al., Immunotherapeutic perspective for bispecific antibodies, Immunol. Today, 21(8):391-7 (2000).
Vasquez, K.M. et al., Manipulating the mammalian genome by homologous recombination, Proc. Natl. Acad. Sci. U S A., 98(15):8403-10 (2001).
Vaughan, T.J. et al., Human antibodies with sub-nanomolar affinities isolated from a large non-immunized phage display library, Nat. Biotechnol., 14(3):309-14 (1996).
Vieira, P. and Rajewsky, K., The half-lives of serum immunoglobulins in adult mice,; Eur. J. Immunol., 18(2):313-6 (1988).
Winter, D.B. et al., Insertion of 2 kb of bacteriophage DNA between an immunoglobulin promoter and leader exon stops somatic hypermutation in a kappa transgene, Mol. Immunol., 34(5):359-66 (1997).
Wu, H. et al., Double replacement: strategy for efficient introduction of subtle mutations into the murine Col1a-1 gene by homologous recombination in embryonic stem cells, Proc. Natl. Acad. Sci. U S A., 91(7):2819-23 (1994).
Yang, X.W. et al., Homologous recombination based modification in *Escherichia coli* and germline transmission in transgenic mice of a bacterial artificial chromosome, Nat. Biotechnol. 15(9):859-65 (1997).
Zemlin, M. et al., Expressed Murine and Human CDR-H3 Intervals of Equal Length Exhibit Distinct Repertoires that Differ in their Amino Acid Composition and Predicted Range of Structures, JMB, 334:733-749 (2003).
Zheng, J. et al., Immunoglobulin gene transcripts have distinct VHDJH recombination characteristics in human epithelial cancer cells, J. Biol. Chem., 284(20):13610-9 (2009).
Author Not Known, Mouse strain, document #3 submitted with Third Party Observation, filed in GB2012052956, 4 pages (Mar. 26, 2014).
Bot, A. et al., V2-Light Chain Genes Reconstitute Immune Responses to Defined Carbohydrate Antigens or Haptens by Utilizing Different VH Genes, Molecular Immunology, 33(17/18):1359-1368 (1996).
Chen, C. et al., Deletion and Editing of B Cells that Express Antibodies to DNA, Journal of Immunology, 152(4):1970-1982 (1994).
Declaration of Brink dated Apr. 30, 2015, as filed in AU Application No. 2009263082, 34 pages.
Declaration of Brink dated Jun. 2, 2015, as filed in AU Application No. 2009263082, 38 pages.
Declaration of DeFranco dated Dec. 21, 2014, as filed in AU Application No. 2009263082, 56 pages.
Declaration of DeFranco dated Oct. 19, 2015, as filed in AU Application No. 2009263082, 31 pages.
Declaration of Denley dated May 1, 2015, as filed in AU Application No. 2009263082, 493 pages.
Declaration of Goodnow dated Oct. 19, 2015, as filed in AU Application No. 2009263082, 81 pages.
Declaration of Hudson dated Jun. 2, 2015, as filed in AU Application No. 2009263082, 81 pages.
Declaration of Hudson dated May 1, 2015, as filed in AU Application No. 2009263082, 52 pages.
Declaration of Murphy dated Dec. 19, 2014, as filed in AU Application No. 2009263082, 18 pages.
Declaration of Tarlinton dated Dec. 21, 2014, as filed in AU Application No. 2009263082, 40 pages.
Declaration of Tarlinton dated Oct. 19, 2015, as filed in AU Application No. 2009263082, 24 pages.
Hartley, S. and Goodnow, C., Censoring of self-reactive B cells with a range of receptor affinities in transgenic mice expressing heavy chains for a lysozyme-specific antibody, International Immunology, 6:1417-1425 (1994).
Houdebine, L.M. Transgenic Animals: Generation and Use. Amsterdam: Harwood Academic Publishers.pp. 397-403 (1997).
Opposition dated Aug. 11, 2014, in EP Application No. 09075279.1, 983 pages.
Opposition dated Aug. 20, 2015, in EP Application No. 09075279.1, 25 pages.
Opposition dated Sep. 22, 2014, in AU Application No. 2009263082, 35 pages.
Opposition filed in European Application No. 10186063.3, 1351 pages (Jul. 15, 2014).
Phan, T. et al., Altered Migration, Recruitment, and Somatic Hypermutation in the Early Response of Marginal Zone B Cells to T Cell-Dependent Antigen, The Journal of Immunology, 174(8):4567-78 (2005).
Phan, T. et al., B Cell Receptor-independent Stimuli Trigger Immunoglobulin (Ig) Class Switch Recombination and Production of IgG Autoantibodies by Anergic Self-Reactive B Cells, The Journal of Experimental Medicine, 197(7):845-860 (2003).
Phan, T.G. et al., High affinity germinal center B cells are actively selected into the plasma cell compartment, J. Exp. Med., 203(11):2419-24 (2006).
Ritchie, K. et al., Allelic exclusion and control of endogenous immunoglobulin gene rearrangement in kappa transgenic mice, Nature, 312:517-520 (1984).
Third Party Observation dated Apr. 8, 2014, in CA Application No. 2729095, 16 pages.
Third Party Observation dated Apr. 25, 2012, in EP Application No. 09075279.1, 145 pages.
Third Party Observation dated Feb. 28, 2013, in EP Application No. 11703799.4, 43 pages.
Third Party Observation dated Jul. 1, 2013, in EP Application No. 09075279.1, 6 pages.
Third Party Observation dated Jun. 24, 2013, in EP Application No. 09075279.1, 15 pages.
Third Party Observation dated May 16, 2013, in EP Application No. 09075279.1, 82 pages.
Third Party Observation dated Nov. 18, 2014, in EP Application No. 11703799.4, 132 pages.
Third Party Observation dated Nov. 3, 2014, in EP Application No. 12173456.0, 274 pages.
Third Party Observation dated Oct. 3, 2013, in EP Application No. 09075279.1, 3 pages.
Third Party Observation dated Oct. 21, 2013, in AU Application No. 2009263082, 24 pages.
Third Party Observation dated Oct. 25, 2012, in EP Application No. 09075279.1, 27 pages.
Third Party Observation dated Sep. 12, 2013, in EP Application No. 09075279.1, 5 pages.
Third Party Observation dated Sep. 16, 2015, in CA Application No. 2729095, 15 pages.
Third Party Observation dated Sep. 5, 2013, in EP Application No. 09075279.1, 11 pages.
Third Party Observation dated Sep. 7, 2015, in EP Application No. 12173456.0, 68 pages.
Third Party Observation pursuant to Article 115 EPC for EP 14170196.1, 6 pages (Jul. 1, 2015).
Third Party Submission dated Feb. 18, 2013, in U.S. Appl. No. 13/093,156, 179 pages.
Third Party Submission dated Feb. 19, 2014, in U.S. Appl. No. 13/750,753, 282 pages.
Third Party Submission dated Feb. 24, 2014, in U.S. Appl. No. 13/750,753, 97 pages.
Third Party Submission dated Feb. 27, 2014, in U.S. Appl. No. 13/948,818, 10 pages.
Third Party Submission dated Jan. 28, 2013, in U.S. Appl. No. 12/589,181, 13 pages.

(56) References Cited

OTHER PUBLICATIONS

Third Party Submission dated Jun. 12, 2013, in U.S. Appl. No. 13/750,753, 100 pages.
Third Party Submission filed in U.S. Appl. No. 13/795,637, 117 pages (Mar. 18, 2014).
Tiegs, S. et al., Receptor Editing in Self-reactive Bone Marrow B Cells,The Journal of Experimental Medicine, 177:1009-1020 (1993).
Written Opinion for PCT/US2013/044257, 5 pages (Sep. 4, 2013).
Xu, J. and Davis, M. Diversity in the CDR3 Region of VH Is Sufficient for Most Antibody Specificities, Immunity, 13:37-45 (2000).
Author Not Known, Chapter 6: The Development of B Lymphocytes, Immuno Biology: The Immune System in Health and Disease, 4th Edition, Janeway et al. ed., pp. 195-208 (1999).
Bode, J. et al., The transgeneticist's toolbox: novel methods for the targeted modification of eukaryotic genomes, Biol. Chem., 381(9-10):801-13 (2000).
Brief comments on third party observations, EP 11703799.1-1410, submitted to EPO by David Power, 3 pages (Apr. 20, 2015).
Brüggemann, M. and Neuberger, M.S., Strategies for expressing human antibody repertoires in transgenic mice, Immunol. Today, 17(8):391-7 (1996).
Campbell, K.H. et al., Sheep cloned by nuclear transfer from a cultured cell line, Nature, 380(6569):64-6 (1996).
Casellas, R. et al., Contribution of receptor editing to the antibody repertoire, Science, 291(5508):1541-4 (2001).
De Kruif, J. et al., Rapid selection of cell subpopulation-specific human monoclonal antibodies from a synthetic phage antibody library, Proc. Natl. Acad. Sci. U S A, 92(9):3938-42 (1995).
Declaration of Dr. Joel Martin, Opposition filed against European Patent No. EP 2314629 B1, 13 pages (May 18, 2016).
Dinnyés, a. et al., Somatic cell nuclear transfer: recent progress and challenges, Cloning Stem Cells, 4(1):81-90 (2002).
English Translation of Arguments dated Jan. 14, 2014, as filed in Merus Japanese Patent No. 5749161, 6 pages.
English Translation of Arguments dated Jan. 5, 2015, as filed in Merus Japanese Patent No. 5749161, 9 pages.
Extended European Search Report for EP 15186515.1, 8 pages (dated Feb. 3, 2016).
Final Written Submissions for Oral Proceedings Scheduled for Jun. 22, 2016, Opposition to Merus B.V.'s EP 2314629 B1, 13 pages (May 20, 2016).
Flavell, D.J., et al., Therapy of human T-cell acute lymphoblastic leukaemia with a combination of anti-CD7 and anti-CD38-SAPORIN immunotoxins is significantly better than therapy with each individual immunotoxin, Br. J. Cancer., 84(4):571-8 (2001).
Forrest, K. B., Opinion of the United States District Court, *Regeneron Pharmaceuticals, Inc.* v. *Merus B.V.*, 114 pages (Nov. 2, 2015).
Giddings, G. et al., Transgenic plants as factories for biopharmaceuticals, Nat. Biotechnol., 18(11):1151-5 (2000).
Hiatt, A. et al. Production of antibodies in transgenic plants, Nature, 342(6245):76-8 (1989).
Huls, G. et al., Antitumor immune effector mechanisms recruited by phage display-derived fully human IgG1 and IgA1 monoclonal antibodies, Cancer Res., 59(22):5778-84 (1999).
Jakobovits, Therapeutic Antibodies from XenoMouse Transgenic Mice, Recombinant Antibodies for Immunotherapy, Ed. Little, M., New York, NY: Cambridge University Press, Chapter 7, pp. 89-99 (2009).
Jones, D. et al., High-level expression of recombinant IgG in the human cell line per.c6, Biotechnol. Prog., 19(1):163-8 (2003).
Joyner, A.L. ed., Gene Targeting: A Practical Approach, Second Edition, Oxford University Press, entire book, 193 pages (2000).
Kasprzyk, P.G. et al., Therapy of an animal model of human gastric cancer using a combination of anti-erbB-2 monoclonal antibodies, Cancer Res., 52(10):2771-6 (1992).
Kontermann, R.E., Dual targeting strategies with bispecific antibodies, MAbs., 4(2):182-97 (2012).

Kroesen, B.J. et al., Bispecific antibodies for treatment of cancer in experimental animal models and man, Adv. Drug Deliv. Rev., 31(1-2):105-129 (1998).
Larrick, J.W. and Thomas, D.W., Producing proteins in transgenic plants and animals, Curr. Opin. Biotechnol., 12(4):411-8 (2001).
Lefranc, M-P. and Lefranc, G., The Immunoblobulin Facts Books, San Diego, CA: Academic Press, entire book, pp. 1-457 (2001).
Lonberg, N., Fully human antibodies from transgenic mouse and phage display platforms, Curr. Opin. Immunol., 20(4):450-9, and supplemental material, 16 pages (2008).
Matsuda, F. et al., The Complete Nucleotide Sequence of the Human Immunoglobulin Heavy Chain Variable Region Locus, J. Exp. Med., 188(11): 2151-2162 (1998).
Nelson, A.L. et al., Development trends for human monoclonal antibody therapeutics, Nat. Rev. Drug. Discov., 9(10):767-74 (2010).
Nemazee, D., Receptor editing in B cells, Adv. Immunol., 74:89-126 (2000).
Nissim et al., Antibody fragments from a 'single pot' phage display library as immunochemical reagents, EMBO J., 13(3): 692-698 (1994).
Notice of opposition to a European patent for EP 2314629, *Merus B.V.* v. *Regeneron Pharmaceuticals, Inc.*, 38 pages (Jul. 15, 2014).
Opposition dated Jan. 15, 2016, in JP Patent No. 5749161 and English translation, 188 pages.
Peeters, K. et al., Production of antibodies and antibody fragments in plants, Vaccine, 19(17-19):2756-61 (2001).
Pollock, D.P. et al., Transgenic milk as a method for the production of recombinant antibodies, J. Immunol. Methods., 231(1-2):147-57 (1999).
Radic, M.Z. et al., Ig H and L chain contributions to autoimmune specificities, J. Immunol., 146(1):176-82 (1991).
Schnieke, A.E. et al., Human factor IX transgenic sheep produced by transfer of nuclei from transfected fetal fibroblasts, Science, 278(5346):2130-3 (1997).
Segal, D. et al., Introduction: bispecific antibodies, Journal of Immunological Methods, 248(12):1-6 (2001).
Sirac, C. et al., Light chain inclusion permits terminal B cell differentiation and does not necessarily result in autoreactivity, Proc. Natl. Acad. Sci, U S A, 103(20):7747-52 (2006), and Supplemental information, 4 pages, retrieved Jul. 7, 2016: <http://www.pnas.org/content/103/20/7747.long?tab=ds#F6>.
Smith, E.J. et al., A novel, native-format bispecific antibody triggering T-cell killing of B-cells is robustly active in mouse tumor models and cynomolgus monkeys, Sci. Rep., 5:17943 (2015).
Su, Q. et al., A DNA transposon-based approach to validate oncogenic mutations in the mouse, Proc. Natl. Acad. Sci. USA, 105(50):19904-9 (2008).
Summons to attend oral proceedings dated Jan. 19, 2016, in EP Application 09075279.1, 20 pages.
Taki, S. et al., Targeted insertion of a variable region gene into the immunoglobulin heavy chain locus, Science, 262(5137):1268-71 (1993).
Waterfield, M.D. et al., Restricted Structural Heterogeneity in Antibodies: Might Different Heavy Chains have a Common Light Chain? Nature New Biology, vol. 240:215-217 (1972).
Wilmut, I. and Clark, A.J., Basic techniques for transgenesis, J. Reprod. Fertil. Suppl., 43:265-75 (1991).
Wilmut, I. et al., Viable offspring derived from fetal and adult mammalian cells, Nature, 385(6619):810-3 (1997).
Zou, Y.R. et al., Cre-loxP-mediated gene replacement: a mouse strain producing humanized antibodies, Curr. Biol., 4(12):1099-103 (1994).
Notice of Opposition for EP 2501817, 28 pages (May 25, 2016).
Collins, A. et al., The reported germline repertoire of human immunoglobulin kappa chain genes is relatively complete and accurate, Immunogenetics, 60:669-676 (2008).
Corrected Claims in JP5749161 (English and Japanese), 6 pages.
Cover Letter—Applicant Post—Hearing Submissions in AU2009263082, 1 page (Oct. 19, 2016).
Declaration for Robert Brink in AU 2009263082, 19 pages (Oct. 19, 2016).
Declaration of Dr. Joel Martin in EP2314629, 13 pages (May 18, 2016).

(56) References Cited

OTHER PUBLICATIONS

Declaration of Dr. Ton Logtenberg filed in U.S. Appl. No. 13/750,753, 10 pages (Dec. 18, 2015).
Declaration of Dr. Ton Logtenberg filed in U.S. Appl. No. 13/750,753, 4 pages (Sep. 15, 2015).
Declaration of Professor Ton Logtenberg for EP2314629, 7 pages (May 4, 2016).
Engel, P. et al., Abnormal B Lymphocyte Development, Activation, and Differentiation in Mice that Lack or Overexpress the CD19 Signal Transduction Molecule, Immunity, 3:39-50 (1995).
Final Post-Hearing Submission—DeFranco Declaration Annexure in AU2009263082, 10 pages (Oct. 18, 2016).
Final Post—Hearing Submission—Opponent in AU2009263082, 4 pages (Oct. 19, 2016).
Final Response to Opposition in EP2501817, 27 pages (Dec. 23, 2016).
Fussenegger, M. et al., Genetic optimization of recombinant glycoprotein production by mammalian cells, Tibtech, 17:35-42 (1999).
Initial Determination in EP Application No. 10186063.3, 11 pages (Nov. 19, 2015).
JP Opposition Decision in JP5749161 (English and Japanese), 54 pages (Sep. 7, 2016).
Notice of Opposition in EP2701499, 27 pages (Nov. 10, 2016).
Notice of Opposition in JP5749161 (English and Japanese), 188 pages (Jan. 15, 2016).
Notice of Reasons for Revocation in JP5749161, (English and Japanese), 18 pages (Mar. 17, 2016).
Notice of Receipt of Correction Request in JP5749161 (English and Japanese), 2 pages (Jul. 1, 2016).
Opposition's rebuttal to Proprietor's submissions in Opposition No. 700031/2016 (English and Japanese), 64 pages (Aug. 22, 2016).
Patent Owner Final Submissions in response to the Summons to attend Oral Proceedings dated Nov. 19, 2015 and in preparation of the Hearing of Jun. 22, 2016 for EP2314629, 16 pages (May 20, 2016).
Patentee's Exhibit 1 submitted with Argument against Opposition No. 700031/2016 on Jun. 21, 2016, "Really Essential Medical Immunology", Blackwell Science Ltd. Cover, colophon, Contents and Chapter 3 (pp. 23-25) (English and Japanese), 17 pages (2000).
Patentee's Exhibit 2 submitted with Argument against Opposition No. 700031/2016 on Jun. 21, 2016, Communication to the EPO submitted by the Opponent in connection with prosecution of EP2505654 (English and Japanese), 7 pages (Sep. 29, 2014).
Patentee's Exhibit 3 submitted with Argument against Opposition No. 700031/2016 on Jun. 21, 2016, Declaration of Peter Hudson (English and Japanese), 15 pages (Jun. 17, 2016).
Patentee's Arguments against Opposition No. 700031/2016 (English and Japanese), 29 pages (Jun. 21, 2016).
Phelps, J. et al., Expression and Characterization of a Chimeric Bifunctional Antibody with Therapeutic Applications, The Journal of Immunology, 145:1200-1204 (1990).
Request for Correction in JP5749161 (English and Japanese), 29 pages (Jun. 21, 2016).
Response Post-Hearing Submissions by Applicant in AU2009263082, 15 pages (Oct. 19, 2016).
Response to Notice of Opposition dated Aug. 22, 2014 for EP2314629, 20 pages (Feb. 24, 2015).
Rickert, R. et al., Impairment of T-cell-dependent B-cell responses and B-1 cell development in CD19-deficient mice, Nature, 376(6538):352-5 (1995).
Tada, H. et al., Expression and characterization of a chimeric bispecific antibody against fibrin and against urokinase-type plasminogen activator, Journal of Biotechnology, 33:157-174 (1994).
Verma, R. et al., Antibody engineering: Comparison of bacterial, yeast, insect and mammalian expression systems, Journal of Immunological Methods, 216:165-181 (1998).
Applicant's Written Submissions for AU2009263082, 49 pages (Sep. 6, 2016).

Declaration of Brink dated Sep. 27, 2016, as filed against EP Patent No. 2,147,594 B1 (European patent application No. 09075279.1), 33 pages.
Final Written Submissions Oral Proceedings Scheduled for Oct. 28, 2016 in EP2147594, 40 pages.
Initial Post-Hearing Submissions (Applicant) Brink Declaration Annex for Australian patent application No. 2009263082, 36 pages (Oct. 4, 2016).
Letter Accompanying Initial Post-Hearing Submissions (Applicant) for Australian patent application No. 2009263082, 1 page (Oct. 5, 2016).
Initial Post-Hearing Submissions (Applicant) for Australian patent application No. 2009263082, 5 pages (Oct. 5, 2016).
Initial Post-Hearing Submissions (Opponents Initial Supplementary Submissions) for Australian patent application No. 2009263082, 7 pages (Oct. 5, 2016).
Initial Post-Hearing Submissions—DeFranco Declaration Annexure for Australian patent application No. 2009263082, 41 pages (Oct. 4, 2016).
Initial Post-Hearing Submissions—Goodnow Declaration Annexure for Australian patent application No. 2009263082, 13 pages (Oct. 4, 2016).
International Search Report for PCT/US2011/023971 (dated Apr. 11, 2011).
International Search Report for PCT/US2013/044257 dated Sep. 4, 2014 (4 pages).
Lam, K. et al., In Vivo Ablation of Surface Immunoglobulin on Mature B Cells by Inducible Gene Targeting Results in Rapid Cell Death, Cell, 90:1073-1083 (1997).
Letter in Reply to Merus Response in EP2147594, 9 pages (Aug. 20, 2015).
Merus Final Written Submissions as filed in EP2147594 / 09075279.1-1405, 32 pages (Aug. 26, 2016).
Merus Response to REGN Opposition in EP2147594, 35 pages (Apr. 2, 2015).
Preliminary Opinion of the Opposition Division in EP2147594, 11 pages (Jan. 19, 2016).
Reply to Communication in EP12173456.0, 12 pages (dated Apr. 12, 2013).
Response to Opponents Submission dated Aug. 26, 2016 and in Preparation of the Hearing scheduled for Oct. 28, 2016 in EP2147594, 14 pages (Sep. 28, 2016).
Statement of Facts and Arguments in Support of Opposition for EP2147594, 57 pages (Aug. 11, 2014).
Summary of Opponent's Submissions for AU2009263082, 35 pages (Aug. 30, 2016).
Jendeberg, L. et al., Engineering of Fc1 and Fc3 from human immunoglobulin G to analyse subclass specificity for staphylococcal protein A1, Journal of Immunological Methods, 201:25-34 (1997).
Lantto, J. et al., Capturing the natural diversity of the human antibody response against vaccinia virus, J Virol, 85(4)1 820-33 (2011).
Apr. 17, 2017 Statement of Relatedness, Common Light Chain Patents.
Fishwild, D. et al., High-avidity human IgGk monoclonal antibodies from a novel strain of minilocus transgenic mice, Nature Biotechnology, 14:845-851 (1996).
Declaration of Professor Dr. Roland Kontermann, Ph.D. for EP2505654 B1, 4 pages (May 19, 2017).
Declaration of Professor Michel Cogne, 26 pages (Jul. 17, 2017).
Lee, E.G. et al., Complete humanization of the mouse immunoglobulin loci enables efficient therapeutic antibody discovery, Nat. Biotechnol., 32(4):356-63 (2014).
Longo, N. et al., Characterization of immunoglobulin gene somatic hypermutation in the absence of activation-induced cytidine deaminase, J. Immunol., 181(2):1299-1306 (2008).
Notice of Opposition in EP2505654, 39 pages (May 24, 21017).
Opponent Reply to Patentee Submissions in EP2501817, 5 pages (Mar. 17, 2017).
Patent Oppositions—Decision in for AU2009263082, 53 pages (May 5, 2017).

(56) References Cited

OTHER PUBLICATIONS

Response to Opposition in EP2701499, 22 pages (Apr. 28, 2017).
Statement of Grounds of Appeal for U.S. Pat. No. 2147594, 82 pages (2017).
Summons to Opposition in EP2501817, 12 pages (May 17, 2017).

* cited by examiner

SEQUENCE LISTING

```
<160> NUMBER OF SEQ ID NOS: 18

<210> SEQ ID NO 1
<211> LENGTH: 3155
<212> TYPE: DNA
<213> ORGANISM: Artificial Sequence
<220> FEATURE:
<223> OTHER INFORMATION: Synthetic
<400> SEQUENCE: 1
ggcgcgccgt agctttgaat tttaaacatc tatttgacaa gaaatgcata gttccttctc      60
tttaaaataa tgtaatgttt ctttcaagaa taagcttggt ttgatgcctc tctccccaac     120
atgatagaag tgtagcataa atctatgaaa aattccattt ccctgtgcct acaacaacta     180
cctgggattg aaaacttctt cccttgctct agtcctttct tctacaccta cttccacatc     240
atctgtgact caaaacaata cttgtcagga aagatcccgg aaagagcaaa aaagacttcc     300
ttagaggtgt cagagattcc tatgccacta tctgtcatct ctagaagggg ttgtgagtat     360
gaggaagagc agagcttgta aattttctac ttgctttgac ttccactgta tttcctaaca     420
acaacaacca cagcaacacc cataacatca caggacaaac ttctagtact tccaaggctt     480
tagtctcagt aaatcttctc tacctccatc acagcagcta gaaggtttga tactcataca     540
```

```
aatagtactg tagctttctg ttcataattg gaaaaataga caagacccaa tgtaatacag    600
gctttccttc agccagttag cgttcagttt ttggatcacc attgcacaca tatacccagc    660
atatgtctaa tatatatgta gaaatccgtg aagcaagagt tataatagct tgtgttttct    720
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga agaaggaca   1020 gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagttttca cttttaact    1560 caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tgacatccag atgacccagt ctccatcctc cctgtctgca   2400
tctgtaggag acagagtcac catcacttgc cgggcaagtc agagcattag cagctattta   2460
aattggtatc agcagaaacc agggaaagcc cctaagctcc tgatctatgc tgcatccagt   2520
ttgcaaagtg gggtcccatc aaggttcagt ggcagtggat ctgggacaga tttcactctc   2580
accatcagca gtctgcaacc tgaagatttt gcaacttact actgtcaaca gagttacagt   2640
acccctccga tcaccttcgg ccaagggaca cgactggaga ttaaacgtaa gtaattttc    2700 actattgtct tctgaaattt gggtctgatg ccagtattg acttttagag gcttaaatag    2760
gagtttggta aagattggta aatgagggca tttaagattt gccatgggtt gcaaagtta   2820 aactcagctt caaaaatgga tttggagaaa aaaagattaa attgctctaa actgaatgac   2880
```

| | |
|---|---|
| acaaagtaaa aaaaaaaagt gtaactaaaa aggaacccct gtatttctaa ggagcaaaag | 2940 |
| taaatttatt tttgttcact cttgccaaat attgtattgg ttgttgctga ttatgcatga | 3000 |
| tacagaaaag tggaaaaata catttttag tctttctccc ttttgtttga taaattattt | 3060 |
| tgtcagacaa caataaaaat caatagcacg ccctaagatc tagatgcatg ctcgagtgcc | 3120 |
| atttcattac ctctttctcc gcacccgaca tagat | 3155 |

```
<210> SEQ ID NO 2
<211> LENGTH: 28
<212> TYPE: DNA
<213> ORGANISM: Artificial Sequence
<220> FEATURE:
<223> OTHER INFORMATION: Synthetic

<400> SEQUENCE: 2
```

| | |
|---|---|
| aggtgagggt acagataagt gttatgag | 28 |

```
<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
```

| | |
|---|---|
| tgacaaatgc cctaattata gtgatca | 27 |

```
<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
```

| | |
|---|---|
| gggcaagtca gagcattagc a | 21 |

```
<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
```

| | |
|---|---|
| tgcaaactgg atgcagcata g | 21 |

```
<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
```

| | |
|---|---|
| ggtggagagg ctattcggc | 19 |

```
<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7
```

| gaacacggcg gcatcag | 17 |

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8

| tgggcacaac agacaatcgg ctg | 23 |

<210> SEQ ID NO 9
<211> LENGTH: 29
<212> TYPE: DNA
<213> ORGANISM: Artificial Sequence
<220> FEATURE:
<223> OTHER INFORMATION: Synthetic

<400> SEQUENCE: 9

| ccattatgat gctccatgcc tctctgttc | 29 |

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10

| atcagcagaa accagggaaa gcccct | 26 |

<210> SEQ ID NO 11
<211> LENGTH: 3166
<212> TYPE: DNA
<213> ORGANISM: Artificial Sequence
<220> FEATURE:
<223> OTHER INFORMATION: Synthetic

<400> SEQUENCE: 11

| ggcgcgccgt agctttgaat tttaaacatc tatttgacaa gaaatgcata gttccttctc | 60 |
| tttaaaataa tgtaatgttt cttccaagaa taagcttggt ttgatgcctc tctccccaac | 120 |
| atgatagaag tgtagcataa atctatgaaa aattccattt ccctgtgcct acaacaacta | 180 |
| cctgggattg aaaacttctt cccttgctct agtcctttct tctacaccta cttccacatc | 240 |
| atctgtgact caaacaata cttgtcagga agatcccgg aaagagcaaa aaagacttcc | 300 |
| ttagaggtgt cagagattcc tatgccacta tctgtcatct ctagaagggg ttgtgagtat | 360 |
| gaggaagagc agagcttgta aattttctac ttgctttgac ttccactgta tttcctaaca | 420 |
| acaacaacca cagcaacacc cataacatca caggacaaac ttctagtact tccaaggctt | 480 |
| tagtctcagt aaatcttctc tacctccatc acagcagcta gaaggtttga tactcataca | 540 |
| aatagtactg tagctttctg ttcataattg gaaaaataga caagacccaa tgtaatacag | 600 |
| gctttccttc agccagttag cgttcagttt ttggatcacc attgcacaca tatacccagc | 660 |
| atatgtctaa tatatatgta gaaatccgtg aagcaagagt tataatagct tgtgttttct | 720 |
| attgtattgt attttcctct tatatcatct tcttcttcgt tcattaaaaa aaaccgttc | 780 |
| aagtaggtct aaattaatta ttggatcata agtagataaa atattttatt tcataacaca | 840 |
| ttgacccgat gaatatgttt ctttgccaga catagtcctc atttccaagg taacaagcct | 900 |

-continued

```
gaaaaaatta tactggagca agtcaacagg taatgatggt agcttttcct tattgtcctg    960
gggcaagaat aagacaaaag ataacagggt agaataaaga ttgtgtaaga aagaaggaca   1020
gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagttttttca cttttttaact   1560
caaagagggt atgtggctgg gttaatgaaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag actttctgg cctgacaacc agggcggcgc aggatgctca   1920
gtgcagagag gaagaagcag gtggtctttg cagctgaaag ctcagctgat tgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tataccaccg gagaaattgt gttgacgcag tctccaggca   2400
ccctgtcttt gtctccaggg gaaagagcca ccctctcctg cagggccagt cagagtgtta   2460
gcagcagcta cttagcctgg taccagcaga aacctggcca ggctcccagg ctcctcatct   2520
atggtgcatc cagcagggcc actggcatcc cagacaggtt cagtggcagt gggtctggga   2580
cagacttcac tctcaccatc agcagactgg agcctgaaga ttttgcagtg tattactgtc   2640
agcagtatgg tagctcacct tggacgttcg gccaagggac caaggtggaa atcaaacgta   2700
agtaattttt cactattgtc ttctgaaatt tgggtctgat ggccagtatt gacttttaga   2760
ggcttaaata ggagtttggt aaagattggt aaatgagggc atttaagatt tgccatgggt   2820
tgcaaaagtt aaactcagct tcaaaaatgg atttggagaa aaaagatta aattgctcta   2880
aactgaatga cacaaagtaa aaaaaaaaag tgtaactaaa aaggaaccct tgtatttcta   2940
aggagcaaaa gtaaatttat ttttgttcac tcttgccaaa tattgtattg ttgttgctg   3000
attatgcatg atacagaaaa gtggaaaaat acatttttta gtctttctcc cttttgtttg   3060
ataaattatt ttgtcagaca acaataaaaa tcaatagcac gccctaagat ctagatgcat   3120
gctcgagtgc catttcatta cctctttctc cgcacccgac atagat             3166
```

<210> SEQ ID NO 12
<211> LENGTH: 19

```
<212> TYPE: DNA
<213> ORGANISM: Artificial Sequence
<220> FEATURE:
<223> OTHER INFORMATION: Synthetic

<400> SEQUENCE: 12
tccaggcacc ctgtctttg                                                    19

<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
aagtagctgc tgctaacact ctgact                                            26

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
aaagagccac cctctcctgc aggg                                              24

<210> SEQ ID NO 15
<211> LENGTH: 3187
<212> TYPE: DNA
<213> ORGANISM: Artificial Sequence
<220> FEATURE:
<223> OTHER INFORMATION: Synthetic

<400> SEQUENCE: 15
ggcgcgccgt agctttgaat tttaaacatc tatttgacaa gaaatgcata gttccttctc        60
tttaaaataa tgtaatgttt cttcaagaa taagcttggt ttgatgcctc tctccccaac       120
atgatagaag tgtagcataa atctatgaaa aattccattt ccctgtgcct acaacaacta       180
cctgggattg aaaacttctt cccttgctct agtccttct tctacaccta cttccacatc       240
atctgtgact caaaacaata cttgtcagga aagatcccgg aaagagcaaa aaagacttcc       300
ttagaggtgt cagagattcc tatgccacta tctgtcatct ctagaagggg ttgtgagtat       360
gaggaagagc agagcttgta aattttctac ttgctttgac ttccactgta tttcctaaca       420
acaacaacca cagcaacacc cataacatca caggacaaac ttctagtact tccaaggctt       480
tagtctcagt aaatcttctc tacctccatc acagcagcta aaggtttga tactcataca       540 aatagtactg tagctttctg ttcataattg gaaaaataga caagacccaa tgtaatacag       600
gctttccttc agccagttag cgttcagttt ttggatcacc attgcacaca tacccagc        660 atatgtctaa tatatatgta gaaatccgtg aagcaagagt tataatagct tgtgttttct       720
attgtattgt attttcctct tatatcatct tcttcttcgt tcattaaaaa aaaaccgttc       780
aagtaggtct aaattaatta ttggatcata agtagataaa atattttatt tcataacaca       840
ttgacccgat gaatatgttt ctttgccaga catagtcctc atttccaagg taacaagcct       900
gaaaaaatta tactggagca agtcaacagg taatgatggt agcttttcct tattgtcctg       960
gggcaagaat aagacaaaag ataacagggg agaataaaga ttgtgtaaga aagaaggaca      1020
gcaacaggac atgggaacct tttatagagt aacatttga taatgatga tgagaattaa       1080
```

| | |
|---|---|
| tgagttagac agggatgggt gggaatgatt gaaggtgtga gtactttagc acagattaag | 1140 |
| accaaatcat taggatttaa agagttgtgt agagttagtg aaggaaaagc cttagaatta | 1200 |
| aatttggctg cggataaaac attcttggat tagactgaag actcttttct gtgctaagta | 1260 |
| agtatattta tgataatgat gatgactgta gtgctgaata tttaataaat aaaaacaaaa | 1320 |
| ttaattgccg catacataat gtcctgaata ctattgtaaa tgttttatct tatttccttt | 1380 |
| aaactgtcta cagcactata agtaggtac cagtattgtc acagttacac agatatggaa | 1440 |
| accgagacac agggaagtta agttacttga tcaatttcaa gcaatcggca agccatggag | 1500 |
| catctatgtc agggctgcca ggacatgtga ctgtaaacag aagttttca cttttaact | 1560 |
| caaagagggt atgtggctgg gttaatggaa agcttcagga ccctcagaaa acattactaa | 1620 |
| caagcaaatg aaaggtgtat ctggaagatt aagttttaac agactcttca tttccatcga | 1680 |
| tccaataatg cacttaggga gatgactggg catattgagg ataggaagag agaagtgaaa | 1740 |
| acacagcttt ttatattgtt cttaacaggc ttgtgccaaa catcttctgg gtggatttag | 1800 |
| gtgattgagg agaagaaaga cacaggagcg aaattctctg agcacaaggg aggagttcta | 1860 |
| cactcagact gagccaacag acttttctgg cctgacaacc agggcggcgc aggatgctca | 1920 |
| gtgcagagag gaagaagcag gtggtctttg cagctgaaag ctcagctgat ttgcatatgg | 1980 |
| agtcattata caacatccca gaattcttta agggcagctg ccaggaagct aagaagcatc | 2040 |
| ctctcttcta gctctcagag atggagacag acacactcct gctatgggtg ctgctgctct | 2100 |
| gggttccagg tgagggtaca gataagtgtt atgagcaacc tctgtggcca ttatgatgct | 2160 |
| ccatgcctct ctgttcttga tcactataat tagggcattt gtcactggtt ttaagtttcc | 2220 |
| ccagtcccct gaattttcca ttttctcaga gtgatgtcca aaattattct taaaaattta | 2280 |
| aatgaaaagg tcctctgctg tgaaggcttt taaagatata taaaaataat ctttgtgttt | 2340 |
| atcattccag gtgccagatg tgttgtggtc ctcagccggt gctgcatcag ccgccggcca | 2400 |
| tgtcctcggc ccttggaacc acaatccgcc tcacctgcac cctgaggaac gaccatgaca | 2460 |
| tcggtgtgta cagcgtctac tggtaccagc agaggccggg ccacctccc aggttcctgc | 2520 |
| tgagatattc tcacaatca gacaagagcc agggccccca ggtccccct cgcttctctg | 2580 |
| gatccaaaga tgtggccagg aacaggggt atttgagcat ctctgagctg cagcctgagg | 2640 |
| acgaggctat gtattactgt gctatgcata actcagtgac gcatgtgttt ggcagcggga | 2700 |
| cccagctcac cgttttaagt aagtaatttt tcactattgt cttctgaaat ttgggtctga | 2760 |
| tggccagtat tgacttttag aggcttaaat aggagtttgg taaagattgg taaatgaggg | 2820 |
| catttaagat ttgccatggg ttgcaaaagt taaactcagc ttcaaaaatg gatttggaga | 2880 |
| aaaaagatt aaattgctct aaactgaatg acacaaagta aaaaaaaaaa gtgtaactaa | 2940 |
| aaaggaaccc ttgtatttct aaggagcaaa agtaaattta ttttgttca ctcttgccaa | 3000 |
| atattgtatt ggttgttgct gattatgcat gatacagaaa agtggaaaaa tacattttt | 3060 |
| agtctttctc ccttttgttt gataaattat tttgtcagac aacaataaaa atcaatagca | 3120 |
| cgccctaaga tctagatgca tgctcgagtg ccatttcatt acctctttct ccgcacccga | 3180 |
| catagat | 3187 |

<210> SEQ ID NO 16
<211> LENGTH: 17
<212> TYPE: DNA
<213> ORGANISM: Artificial Sequence
<220> FEATURE:
<223> OTHER INFORMATION: Synthetic

```
<400> SEQUENCE: 16
tgtcctcggc ccttgga                                                      17

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ccgatgtcat ggtcgttcct                                                   20

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
acaatccgcc tcacctgcac cct                                               23
```

COMMON LIGHT CHAIN MOUSE

CROSS-REFERENCE TO RELATED APPLICATIONS

This application claims the benefit under 35 USC § 119(e) of U.S. Provisional Application Ser. No. 61/302,282, filed 8 Feb. 2010, which application is hereby incorporated by reference.

FIELD OF INVENTION

A genetically modified mouse is provided that expresses antibodies having a common human variable/mouse constant light chain associated with diverse human variable/mouse constant heavy chains. A method for making a human bispecific antibody from human variable region gene sequences of B cells of the mouse is provided.

BACKGROUND

Antibodies typically comprise a homodimeric heavy chain component, wherein each heavy chain monomer is associated with an identical light chain. Antibodies having a heterodimeric heavy chain component (e.g., bispecific antibodies) are desirable as therapeutic antibodies. But making bispecific antibodies having a suitable light chain component that can satisfactorily associate with each of the heavy chains of a bispecific antibody has proved problematic.

In one approach, a light chain might be selected by surveying usage statistics for all light chain variable domains, identifying the most frequently employed light chain in human antibodies, and pairing that light chain in vitro with the two heavy chains of differing specificity.

In another approach, a light chain might be selected by observing light chain sequences in a phage display library (e.g., a phage display library comprising human light chain variable region sequences, e.g., a human ScFv library) and selecting the most commonly used light chain variable region from the library. The light chain can then be tested on the two different heavy chains of interest.

In another approach, a light chain might be selected by assaying a phage display library of light chain variable sequences using the heavy chain variable sequences of both heavy chains of interest as probes. A light chain that associates with both heavy chain variable sequences might be selected as a light chain for the heavy chains.

In another approach, a candidate light chain might be aligned with the heavy chains' cognate light chains, and modifications are made in the light chain to more closely match sequence characteristics common to the cognate light chains of both heavy chains. If the chances of immunogenicity need to be minimized, the modifications preferably result in sequences that are present in known human light chain sequences, such that proteolytic processing is unlikely to generate a T cell epitope based on parameters and methods known in the art for assessing the likelihood of immunogenicity (i.e., in silico as well as wet assays).

All of the above approaches rely on in vitro methods that subsume a number of a priori restraints, e.g., sequence identity, ability to associate with specific pre-selected heavy chains, etc. There is a need in the art for compositions and methods that do not rely on manipulating in vitro conditions, but that instead employ more biologically sensible approaches to making human epitope-binding proteins that include a common light chain.

SUMMARY

Figure 1:
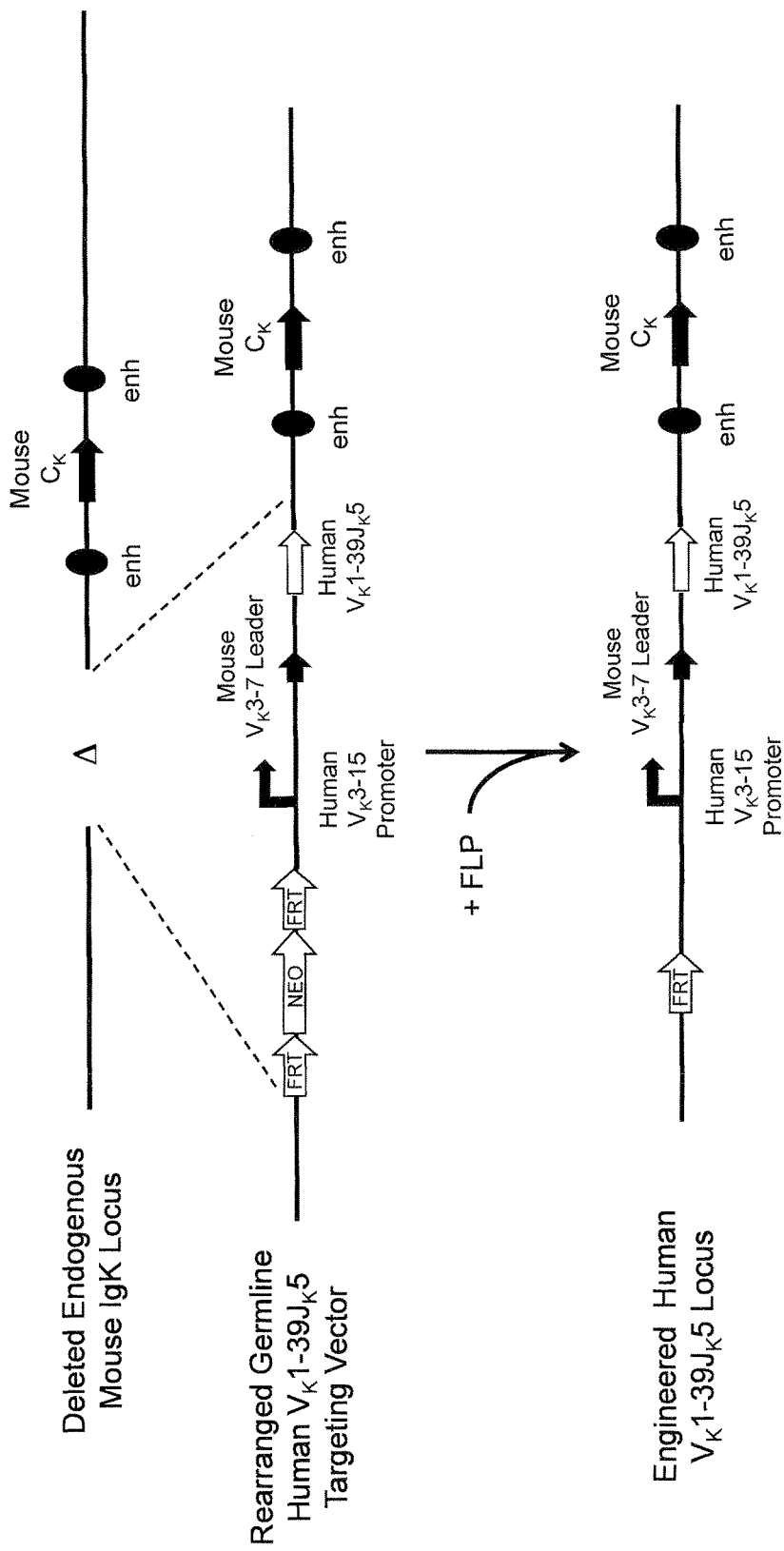
FIG. 1 illustrates a targeting strategy for replacing endogenous mouse immunoglobulin light chain variable region gene segments with a human Vκ1-39Jκ5 gene region.

Genetically modified mice that express human immunoglobulin heavy and light chain variable domains, wherein the mice have a limited light chain variable repertoire, are provided. A biological system for generating a human light chain variable domain that associates and expresses with a diverse repertoire of affinity-matured human heavy chain variable domains is provided. Methods for making binding proteins comprising immunoglobulin variable domains are provided, comprising immunizing mice that have a limited immunoglobulin light chain repertoire with an antigen of interest, and employing an immunoglobulin variable region gene sequence of the mouse in a binding protein that specifically binds the antigen of interest. Methods include methods for making human immunoglobulin heavy chain variable domains suitable for use in making multi-specific antigen-binding proteins.

Genetically engineered mice are provided that select suitable affinity-matured human immunoglobulin heavy chain variable domains derived from a repertoire of unrearranged human heavy chain variable region gene segments, wherein the affinity-matured human heavy chain variable domains associate and express with a single human light chain variable domain derived from one human light chain variable region gene segment. Genetically engineered mice that present a choice of two human light chain variable region gene segments are also provided.

Genetically engineered mice are provided that express a limited repertoire of human light chain variable domains, or a single human light chain variable domain, from a limited repertoire of human light chain variable region gene segments. The mice are genetically engineered to include a single unrearranged human light chain variable region gene segment (or two human light chain variable region gene segments) that rearranges to form a rearranged human light chain variable region gene (or two rearranged light chain variable region genes) that express a single light chain (or that express either or both of two light chains). The rearranged human light chain variable domains are capable of pairing with a plurality of affinity-matured human heavy chains selected by the mice, wherein the heavy chain variable regions specifically bind different epitopes.

In one aspect, a genetically modified mouse is provided that comprises a single human immunoglobulin light chain variable (VL) region gene segment that is capable of rearranging and encoding a human VL domain of an immunoglobulin light chain. In another aspect, the mouse comprises no more than two human VL gene segments that are capable of rearranging and encoding a human VL domain of an immunoglobulin light chain.

In one aspect, a genetically modified mouse is provided that comprises a single rearranged (V/J) human immunoglobulin light chain variable (VL) region segment (i.e., a V/J segment) that encodes a human VL domain of an immunoglobulin light chain. In another aspect, the mouse comprises no more than two rearranged human VL gene segments that are capable of encoding a human VL domain of an immunoglobulin light chain.

In one embodiment, the VL gene segment is a human Vκ1-Jκ5 gene segment or a human Vκ3-20Jκ1 gene segment. In one embodiment, the mouse has both a human Vκ1-39Jκ5 gene segment and a human Vκ3-20Jκ1 gene segment.

In one embodiment, the human VL gene segment is operably linked to a human or mouse leader sequence. In one embodiment, the leader sequence is a mouse leader sequence. In a specific embodiment, the mouse leader sequence is a mouse Vκ3-7 leader sequence.

In one embodiment, the VL gene segment is operably linked to an immunoglobulin promoter sequence. In one embodiment, the promoter sequence is a human promoter sequence. In a specific embodiment, the human immunoglobulin promoter is a Vκ3-15 promoter.

In one embodiment, the genetically modified mouse comprises a VL locus that does not comprise an endogenous mouse VL gene segment that is capable of rearranging to form an immunoglobulin light chain gene, wherein the VL locus comprises a single human VL gene segment that is capable of rearranging to encode a VL region of a light chain gene. In a specific embodiment, the human VL gene segment is a human Vκ1-39Jκ5 gene segment or a human Vκ3-20Jκ1 gene segment.

In one embodiment, the VL locus comprises a leader sequence flanked 5' (with respect to transcriptional direction of the VL gene segment) with a human immunoglobulin promoter and flanked 3' with a human VL gene segment that rearranges and encodes VL domain of a reverse chimeric light chain comprising an endogenous mouse light chain constant region (CL). In a specific embodiment, the VL gene segment is at the mouse kappa (κ) VL locus, and the mouse CL is a mouse κ CL.

In one embodiment, the mouse comprises a nonfunctional lambda (λ) immunoglobulin light chain locus. In a specific embodiment, the λ locus comprises a deletion of one or more sequences of the locus, wherein the one or more deletions renders the λ locus incapable of rearranging to form a light chain gene. In another embodiment all or substantially all of the VL gene segments of the λ locus are deleted.

In one embodiment, the VL locus of the modified mouse is a κ locus, and the κ locus comprises a mouse κ intronic enhancer, a mouse κ 3' enhancer, or both an intronic enhancer and a 3' enhancer.

In one embodiment, mouse makes a light chain that comprises a somatically mutated VL domain derived from a human VL gene segment. In one embodiment, the light chain comprises a somatically mutated VL domain derived from a human VL gene segment, and a mouse κ CL region. In one embodiment, the mouse does not express a λ light chain.

In one embodiment, the genetically modified mouse is capable of somatically hypermutating the human VL region sequence. In a specific embodiment, the mouse comprises a cell that comprises a rearranged immunoglobulin light chain gene derived from the human VL gene segment that is capable of rearranging and encoding a VL domain, and the rearranged immunoglobulin light chain gene comprises a somatically mutated VL domain.

In one embodiment, the mouse comprises a cell that expresses a light chain comprising a somatically mutated human VL domain linked to a mouse κ CL, wherein the light chain associates with a heavy chain comprising a somatically mutated VH domain derived from a human VH gene segment and wherein the heavy chain comprises a mouse heavy chain constant region (CH).

In one embodiment, the mouse comprises a replacement of endogenous mouse VH gene segments with one or more human VH gene segments, wherein the human VH gene segments are operably linked to a mouse CH region gene, such that the mouse rearranges the human VH gene segments and expresses a reverse chimeric immunoglobulin heavy chain that comprises a human VH domain and a mouse CH. In one embodiment, 90-100% of unrearranged mouse VH gene segments are replaced with at least one unrearranged human VH gene segment. In a specific embodiment, all or substantially all of the endogenous mouse VH gene segments are replaced with at least one unrearranged human VH gene segment. In one embodiment, the replacement is with at least 19, at least 39, or at least 80 or 81 unrearranged human VH gene segments. In one embodiment, the replacement is with at least 12 functional unrearranged human VH gene segments, at least 25 functional unrearranged human VH gene segments, or at least 43 functional unrearranged human VH gene segments. In one embodiment, the mouse comprises a replacement of all mouse D and J segments with at least one unrearranged human D segment and at least one unrearranged human J segment. In one embodiment, the at least one unrearranged human D segment is selected from D1-7, D1-26, D3-3, D3-10, D3-16, D3-22, D5-5, D5-12, D6-6, D6-13, D7-27, and a combination thereof. In one embodiment, the at least one unrearranged human J segment is selected from J1, J3, J4, J5, J6, and a combination thereof. In a specific embodiment, the one or more human VH gene segment is selected from a 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, a 6-1 human VH gene segment, and a combination thereof.

In one embodiment, the mouse comprises a B cell that expresses a binding protein that specifically binds an antigen of interest, wherein the binding protein comprises a light chain derived from a human Vκ1-39/Jκ5 rearrangement or a human Vκ3-20/Jκ1 rearrangement, and wherein the cell comprises a rearranged immunoglobulin heavy chain gene derived from a rearrangement of human gene segments selected from a VH2-5, VH3-23, VH3-30, VH 4-39, VH4-59, and VH5-51 gene segment. In one embodiment, the one or more human VH gene segments are rearranged with a human heavy chain J gene segment selected from J1, J3, J4, J5, and J6. In one embodiment, the one or more human VH and J gene segments are rearranged with a human D gene segment selected from D1-7, D1-26, D3-3, D3-10, D3-16, D3-22, D5-5, D5-12, D6-6, D6-13, and D7-27. In a specific embodiment, the light chain gene has 1, 2, 3, 4, or 5 or more somatic hypermutations.

In one embodiment, the mouse comprises a B cell that comprises a rearranged immunoglobulin heavy chain variable region gene sequence comprising a VH, JH, and DH gene segment selected from VH 2-5+JH1+D6-6, VH3-23+JH4+D3, VH3-23+JH4+D3-10, VH3-30+JH1+D6-6, VH3-30+JH3+D6-6, VH3-30+JH4+D1-7, VH3-30+JH4+D5-12, VH3-30+JH4+D6-13, VH3-30+JH4+D6-6, VH3-30+JH4+D7-27, VH3-30+JH5+D3-22, VH3-30+JH5+D6-6, VH3-30+JH5+D7-27, VH4-39+JH3+D1-26, VH4-59+JH3+D3-16, VH4-59+JH3+D3-22, VH4-59+JH4+D3-16, VH5-51+JH3+D5-5, VH5-51+JH5+D6-13, and VH5-51+JH6+D3-16. In a specific embodiment, the B cell expresses a binding protein comprising a human immunoglobulin heavy chain variable region fused with a mouse heavy chain constant region, and a human immunoglobulin light chain variable region fused with a mouse light chain constant region.

In one embodiment, the human VL gene segment is a human Vκ1-39Jκ5 gene segment, and the mouse expresses a reverse chimeric light chain comprising (i) a VL domain derived from the human VL gene segment and (ii) a mouse CL; wherein the light chain is associated with a reverse chimeric heavy chain comprising (i) a mouse CH and (ii) a somatically mutated human VH domain derived from a human VH gene segment selected from a 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, and 6-1 human VH gene segment, and a combination thereof. In one embodiment, the mouse expresses a light chain that is somatically mutated. In one embodiment the CL is a mouse κ CL.

In one embodiment, the human VL gene segment is a human Vκ3-20Jκ1 gene segment, and the mouse expresses a reverse chimeric light chain comprising (i) a VL domain derived from the human VL gene segment, and (ii) a mouse CL; wherein the light chain is associated with a reverse chimeric heavy chain comprising (i) a mouse CH, and (ii) a somatically mutated human VH derived from a human VH gene segment selected from a 1-2, 2-5, 3-7, 3-9, 3-11, 3-20, 3-23, 3-30, 3-33, 4-59, and 5-51 human VH gene segment, and a combination thereof. In one embodiment, the mouse expresses a light chain that is somatically mutated. In one embodiment the CL is a mouse κ CL.

In one embodiment, the mouse comprises both a human Vκ1-39Jκ5 gene segment and a human Vκ3-20Jκ1 gene segment, and the mouse expresses a reverse chimeric light chain comprising (i) a VL domain derived from a human Vκ1-39Jκ5 gene segment or a human Vκ3-20Jκ1 gene segment, and (ii) a mouse CL; wherein the light chain is associated with a reverse chimeric heavy chain comprising (i) a mouse CH, and (ii) a somatically mutated human VH derived from a human VH gene segment selected from a 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, a 6-1 human VH gene segment, and a combination thereof. In one embodiment, the mouse expresses a light chain that is somatically mutated. In one embodiment the CL is a mouse κ CL.

In one embodiment, 90-100% of the endogenous unrearranged mouse VH gene segments are replaced with at least one unrearranged human VH gene segment. In a specific embodiment, all or substantially all of the endogenous unrearranged mouse VH gene segments are replaced with at least one unrearranged human VH gene segment. In one embodiment, the replacement is with at least 18, at least 39, at least 80, or 81 unrearranged human VH gene segments. In one embodiment, the replacement is with at least 12 functional unrearranged human VH gene segments, at least 25 functional unrearranged human VH gene segments, or at least 43 unrearranged human VH gene segments.

In one embodiment, the genetically modified mouse is a C57BL strain, in a specific embodiment selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola. In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain.

In one embodiment, the mouse expresses a reverse chimeric antibody comprising a light chain that comprises a mouse κ CL and a somatically mutated human VL domain derived from a human Vκ1-39Jκ5 gene segment or a human Vκ3-20Jκ1 gene segment, and a heavy chain that comprises a mouse CH and a somatically mutated human VH domain derived from a human VH gene segment selected from a 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, and a 6-1 human VH gene segment, wherein the mouse does not express a fully mouse antibody and does not express a fully human antibody. In one embodiment the mouse comprises a κ light chain locus that comprises a replacement of endogenous mouse κ VL gene segments with the human Vκ1-39Jκ5 gene segment or the human Vκ3-20Jκ1 gene segment, and comprises a replacement of all or substantially all endogenous mouse VH gene segments with a complete or substantially complete repertoire of human VH gene segments.

In one aspect, a mouse cell is provided that is isolated from a mouse as described herein. In one embodiment, the cell is an ES cell. In one embodiment, the cell is a lymphocyte. In one embodiment, the lymphocyte is a B cell. In one embodiment, the B cell expresses a chimeric heavy chain comprising a variable domain derived from a human gene segment; and a light chain derived from a rearranged human Vκ1-39/J segment, rearranged human Vκ3-20/J segment, or a combination thereof; wherein the heavy chain variable domain is fused to a mouse constant region and the light chain variable domain is fused to a mouse or a human constant region.

In one aspect, a hybridoma is provided, wherein the hybridoma is made with a B cell of a mouse as described herein. In a specific embodiment, the B cell is from a mouse as described herein that has been immunized with an immunogen comprising an epitope of interest, and the B cell expresses a binding protein that binds the epitope of interest, the binding protein has a somatically mutated human VH domain and a mouse CH, and has a human VL domain derived from a human Vκ1-39Jκ5 or a human Vκ3-20Jκ1 gene segment and a mouse CL.

In one aspect, a mouse embryo is provided, wherein the embryo comprises a donor ES cell that is derived from a mouse as described herein.

In one aspect, a targeting vector is provided, comprising, from 5' to 3' in transcriptional direction with reference to the sequences of the 5' and 3' mouse homology arms of the vector, a 5' mouse homology arm, a human or mouse immunoglobulin promoter, a human or mouse leader sequence, and a human LCVR gene segment selected from a human Vκ1-39Jκ5 or a human Vκ3-20Jκ1 gene segment, and a 3' mouse homology arm. In one embodiment, the 5' and 3' homology arms target the vector to a sequence 5' with respect to an enhancer sequence that is present 5' and proximal to the mouse κ constant region gene. In one embodiment, the promoter is a human immunoglobulin variable region gene segment promoter. In a specific embodiment, the promoter is a human Vκ3-15 promoter. In one embodiment, the leader sequence is a mouse leader sequence. In a specific embodiment, the mouse leader sequence is a mouse Vκ3-7 leader sequence.

In one aspect, a targeting vector is provided as described above, but in place of the 5' mouse homology arm the human or mouse promoter is flanked 5' with a site-specific recombinase recognition site (SRRS), and in place of the 3' mouse homology arm the human LCVR gene segment is flanked 3' with an SRRS.

In one aspect, a reverse chimeric antibody made by a mouse as described herein, wherein the reverse chimeric antibody comprises a light chain comprising a mouse CL and a human VL, and a heavy chain comprising a human VH and a mouse CH.

In one aspect, a method for making an antibody is provided, comprising expressing in a single cell (a) a first VH gene sequence of an immunized mouse as described herein fused with a human CH gene sequence; (b) a VL gene sequence of an immunized mouse as described herein fused with a human CL gene sequence; and, (c) maintaining the cell under conditions sufficient to express a fully human antibody, and isolating the antibody. In one embodiment, the cell comprises a second VH gene sequence of a second immunized mouse as described herein fused with a human CH gene sequence, the first VH gene sequence encodes a VH domain that recognizes a first epitope, and the second VH gene sequence encodes a VH domain that recognizes a second epitope, wherein the first epitope and the second epitope are not identical.

In one aspect, a method for making an epitope-binding protein is provided, comprising exposing a mouse as described herein with an immunogen that comprises an epitope of interest, maintaining the mouse under conditions sufficient for the mouse to generate an immunoglobulin molecule that specifically binds the epitope of interest, and isolating the immunoglobulin molecule that specifically binds the epitope of interest; wherein the epitope-binding protein comprises a heavy chain that comprises a somatically mutated human VH and a mouse CH, associated with a light chain comprising a mouse CL and a human VL derived from a human Vκ1-39 Jκ5 or a human Vκ3-20 Jκ1 gene segment.

In one aspect, a cell that expresses an epitope-binding protein is provided, wherein the cell comprises: (a) a human VL nucleotide sequence encoding a human VL domain derived from a human Vκ1-39Jκ5 or a human Vκ3-20Jκ1 gene segment, wherein the human VL nucleotide sequence is fused (directly or through a linker) to a human immunoglobulin light chain constant domain cDNA sequence (e.g., a human κ constant domain DNA sequence); and, (b) a first human VH nucleotide sequence encoding a human VH domain derived from a first human VH nucleotide sequence, wherein the first human VH nucleotide sequence is fused (directly or through a linker) to a human immunoglobulin heavy chain constant domain cDNA sequence; wherein the epitope-binding protein recognizes a first epitope. In one embodiment, the epitope-binding protein binds the first epitope with a dissociation constant of lower than $10^{-6}$ M, lower than $10^{-8}$ M, lower than $10^{-9}$ M, lower than $10^{-10}$ M, lower than $10^{-11}$ M, or lower than $10^{-12}$ M.

In one embodiment, the cell comprises a second human VH nucleotide sequence encoding a second human VH domain, wherein the second human VH sequence is fused (directly or through a linker) to a human immunoglobulin heavy chain constant domain cDNA sequence, and wherein the second human VH domain does not specifically recognize the first epitope (e.g., displays a dissociation constant of, e.g., $10^{-6}$ M, $10^{-5}$ M, $10^{-4}$ M, or higher), and wherein the epitope-binding protein recognizes the first epitope and the second epitope, and wherein the first and the second immunoglobulin heavy chains each associate with an identical light chain of (a).

In one embodiment, the second VH domain binds the second epitope with a dissociation constant that is lower than $10^{-6}$ M, lower than $10^{-7}$ M, lower than $10^{-8}$ M, lower than $10^{-9}$ M, lower than $10^{-10}$ M, lower than $10^{-11}$ M, or lower than $10^{-12}$ M.

In one embodiment, the epitope-binding protein comprises a first immunoglobulin heavy chain and a second immunoglobulin heavy chain, each associated with an identical light chain derived from a human VL gene segment selected from a human Vκ1-39Jκ5 or a human Vκ3-20Jκ1 gene segment, wherein the first immunoglobulin heavy chain binds a first epitope with a dissociation constant in the nanomolar to picomolar range, the second immunoglobulin heavy chain binds a second epitope with a dissociation constant in the nanomolar to picomolar range, the first epitope and the second epitope are not identical, the first immunoglobulin heavy chain does not bind the second epitope or binds the second epitope with a dissociation constant weaker than the micromolar range (e.g., the millimolar range), the second immunoglobulin heavy chain does not bind the first epitope or binds the first epitope with a dissociation constant weaker than the micromolar range (e.g., the millimolar range), and one or more of the VL, the VH of the first immunoglobulin heavy chain, and the VH of the second immunoglobulin heavy chain, are somatically mutated.

In one embodiment, the first immunoglobulin heavy chain comprises a protein A-binding residue, and the second immunoglobulin heavy chain lacks the protein A-binding residue.

In one embodiment, the cell is selected from CHO, COS, 293, HeLa, and a retinal cell expressing a viral nucleic acid sequence (e.g., a PERC.6™ cell).

In one aspect, a reverse chimeric antibody is provided, comprising a human VH and a mouse heavy chain constant domain, a human VL and a mouse light chain constant domain, wherein the antibody is made by a process that comprises immunizing a mouse as described herein with an immunogen comprising an epitope, and the antibody specifically binds the epitope of the immunogen with which the mouse was immunized. In one embodiment, the VL domain is somatically mutated. In one embodiment the VH domain is somatically mutated. In one embodiment, both the VL domain and the VH domain are somatically mutated. In one embodiment, the VL is linked to a mouse κ constant domain.

In one aspect, a mouse is provided, comprising human heavy chain variable gene segments replacing all or substantially all mouse heavy chain variable gene segments at the endogenous mouse locus; no more than one or two human light chain variable gene segments selected from a rearranged Vκ1-39/J and a rearranged Vκ3-20/J segment or a combination thereof, replacing all mouse light chain variable gene segments; wherein the human heavy chain variable gene segments are linked to a mouse constant gene, and the human light chain variable gene segment(s) is linked to a human or mouse constant gene.

In one aspect, a mouse ES cell comprising a replacement of all or substantially all mouse heavy chain variable gene segments with human heavy chain variable gene segments, and no more than one or two rearranged human light chain V/J segments, wherein the human heavy chain variable gene segments are linked to a mouse immunoglobulin heavy chain constant gene, and the human light chain V/J segments are linked to a mouse or human immunoglobulin light chain constant gene. In a specific embodiment, the light chain constant gene is a mouse constant gene.

In one aspect, an antigen-binding protein made by a mouse as described herein is provided. In a specific embodiment, the antigen-binding protein comprises a human immunoglobulin heavy chain variable region fused with a mouse constant region, and a human immunoglobulin light chain variable region derived from a Vκ1-39 gene segment or a Vκ3-20 gene segment, wherein the light chain constant region is a mouse constant region.

In one aspect, a fully human antigen-binding protein made from an immunoglobulin variable region gene sequence from a mouse as described herein is provided, wherein the antigen-binding protein comprises a fully human heavy chain comprising a human variable region derived from a sequence of a mouse as described herein, and a fully human light chain comprising a Vκ1-39 or a Vκ3-20 variable region. In one embodiment, the light chain variable region comprises one to five somatic mutations. In one embodiment, the light chain variable region is a cognate light chain variable region that is paired in a B cell of the mouse with the heavy chain variable region.

In one embodiment, the fully human antigen-binding protein comprises a first heavy chain and a second heavy chain, wherein the first heavy chain and the second heavy chain comprise non-identical variable regions independently derived from a mouse as described herein, and wherein each of the first and second heavy chains express from a host cell associated with a human light chain derived from a Vκ1-39 gene segment or a Vκ3-20 gene segment. In one embodiment, the first heavy chain comprises a first heavy chain variable region that specifically binds a first epitope of a first antigen, and the second heavy chain comprises a second heavy chain variable region that specifically binds a second epitope of a second antigen. In a specific embodiment, the first antigen and the second antigen are different. In a specific embodiment, the first antigen and the second antigen are the same, and the first epitope and the second epitope are not identical; in a specific embodiment, binding of the first epitope by a first molecule of the binding protein does not block binding of the second epitope by a second molecule of the binding protein.

In one aspect, a fully human binding protein derived from a human immunoglobulin sequence of a mouse as described herein comprises a first immunoglobulin heavy chain and a second immunoglobulin heavy chain, wherein the first immunoglobulin heavy chain comprises a first variable region that is not identical to a variable region of the second immunoglobulin heavy chain, and wherein the first immunoglobulin heavy chain comprises a wild-type protein A binding determinant, and the second heavy chain lacks a wild-type protein A binding determinant. In one embodiment, the first immunoglobulin heavy chain binds protein A under isolation conditions, and the second immunoglobulin heavy chain does not bind protein A or binds protein A at least 10-fold, a hundred-fold, or a thousand-fold weaker than the first immunoglobulin heavy chain binds protein A under isolation conditions. In a specific embodiment, the first and the second heavy chains are IgG1 isotypes, wherein the second heavy chain comprises a modification selected from 95R (EU 435R), 96F (EU 436F), and a combination thereof, and wherein the first heavy chain lacks such modification.

In one aspect, a method for making a bispecific antigen-binding protein is provided, comprising exposing a first mouse as described herein to a first antigen of interest that comprises a first epitope, exposing a second mouse as described herein to a second antigen of interest that comprises a second epitope, allowing the first and the second mouse to each mount immune responses to the antigens of interest, identifying in the first mouse a first human heavy chain variable region that binds the first epitope of the first antigen of interest, identifying in the second mouse a second human heavy chain variable region that binds the second epitope of the second antigen of interest, making a first fully human heavy chain gene that encodes a first heavy chain that binds the first epitope of the first antigen of interest, making a second fully human heavy chain gene that encodes a second heavy chain that binds the second epitope of the second antigen of interest, expressing the first heavy chain and the second heavy chain in a cell that expresses a single fully human light chain derived from a human Vκ1-39 or a human Vκ3-20 gene segment to form a bispecific antigen-binding protein, and isolating the bispecific antigen-binding protein.

In one embodiment, the first antigen and the second antigen are not identical.

In one embodiment, the first antigen and the second antigen are identical, and the first epitope and the second epitope are not identical. In one embodiment, binding of the first heavy chain variable region to the first epitope does not block binding of the second heavy chain variable region to the second epitope.

In one embodiment, the first antigen is selected from a soluble antigen and a cell surface antigen (e.g., a tumor antigen), and the second antigen comprises a cell surface receptor. In a specific embodiment, the cell surface receptor is an immunoglobulin receptor. In a specific embodiment, the immunoglobulin receptor is an Fc receptor. In one embodiment, the first antigen and the second antigen are the same cell surface receptor, and binding of the first heavy chain to the first epitope does not block binding of the second heavy chain to the second epitope.

In one embodiment, the light chain variable domain of the light chain comprises 2 to 5 somatic mutations. In one embodiment, the light chain variable domain is a somatically mutated cognate light chain expressed in a B cell of the first or the second immunized mouse with either the first or the second heavy chain variable domain.

In one embodiment, the first fully human heavy chain bears an amino acid modification that reduces its affinity to protein A, and he second fully human heavy chain does not comprise a modification that reduces its affinity to protein A.

In one aspect, an antibody or a bispecific antibody comprising a human heavy chain variable domain made in accordance with the invention is provided. In another aspect, use of a mouse as described herein to make a fully human antibody or a fully human bispecific antibody is provided.

Any of the embodiments and aspects described herein can be used in conjunction with one another, unless otherwise indicated or apparent from the context. Other embodiments will become apparent to those skilled in the art from a review of the ensuing description.

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The term "antibody", as used herein, includes immunoglobulin molecules comprising four polypeptide chains, two heavy (H) chains and two light (L) chains inter-connected by disulfide bonds. Each heavy chain comprises a heavy chain variable (VH) region and a heavy chain constant region (CH). The heavy chain constant region comprises three domains, CH1, CH2 and CH3. Each light chain comprises a light chain variable (VL) region and a light chain constant region (CL). The VH and VL regions can be further subdivided into regions of hypervariability, termed complementarity determining regions (CDR), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to an antibody that has a $K_D$ with respect to its target epitope about of $10^{-9}$ M or lower (e.g., about $1 \times 10^{-9}$ M, $1 \times 10^{-10}$ M, $1 \times 10^{-11}$ M, or about $1 \times 10^{-12}$ M). In one embodiment, $K_D$ is measured by surface plasmon resonance, e.g., BIACORE™; in another embodiment, $K_D$ is measured by ELISA.

The phrase "bispecific antibody" includes an antibody capable of selectively binding two or more epitopes. Bispecific antibodies generally comprise two nonidentical heavy chains, with each heavy chain specifically binding a different epitope—either on two different molecules (e.g., different epitopes on two different immunogens) or on the same molecule (e.g., different epitopes on the same immunogen). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding or one or both of the heavy chains to one or both epitopes.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The phrase "epitope-binding protein" includes a protein having at least one CDR and that is capable of selectively recognizing an epitope, e.g., is capable of binding an epitope with a $K_D$ that is at about one micromolar or lower (e.g., a $K_D$ that is about $1\times10^{-6}$ M, $1\times10^{-7}$ M, $1\times10^{-9}$ M, $1\times10^{-9}$ M, $1\times10^{-10}$ M, $1\times10^{-11}$ M, or about $1\times10^{-12}$ M). Therapeutic epitope-binding proteins (e.g., therapeutic antibodies) frequently require a $K_D$ that is in the nanomolar or the picomolar range.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germline" includes reference to an immunoglobulin nucleic acid sequence in a non-somatically mutated cell, e.g., a non-somatically mutated B cell or pre-B cell or hematopoietic cell.

The phrase "heavy chain," or "immunoglobulin heavy chain" includes an immunoglobulin heavy chain constant region sequence from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR.

The term "identity" when used in connection with sequence, includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences, but in the case of a light chain constant domain, the length should contain sequence of sufficient length to fold into a light chain constant domain that is capable of self-association to form a canonical light chain constant domain, e.g., capable of forming two beta sheets comprising beta strands and capable of interacting with at least one CH1 domain of a human or a mouse. In the case of a CH1 domain, the length of sequence should contain sequence of sufficient length to fold into a CH1 domain that is capable of forming two beta sheets comprising beta strands and capable of interacting with at least one light chain constant domain of a mouse or a human.

The phrase "immunoglobulin molecule" includes two immunoglobulin heavy chains and two immunoglobulin light chains. The heavy chains may be identical or different, and the light chains may be identical or different.

The phrase "light chain" includes an immunoglobulin light chain sequence from any organism, and unless otherwise specified includes human κ and λ light chains and a VpreB, as well as surrogate light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear. Common light chains are those derived from a human Vκ1-39Jκ5 gene segment or a human Vκ3-20Jκ1 gene segment, and include somatically mutated (e.g., affinity matured) versions of the same.

The phrase "micromolar range" is intended to mean 1-999 micromolar; the phrase "nanomolar range" is intended to mean 1-999 nanomolar; the phrase "picomolar range" is intended to mean 1-999 picomolar.

The phrase "somatically mutated" includes reference to a nucleic acid sequence from a B cell that has undergone class-switching, wherein the nucleic acid sequence of an immunoglobulin variable region (e.g., a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" refers to sequences from antibodies that have been generated in an animal, e.g., a mouse having human immunoglobulin variable region nucleic acid sequences, in response to an immunogen challenge, and that result from the selection processes inherently operative in such an animal.

The term "unrearranged," with reference to a nucleic acid sequence, includes nucleic acid sequences that exist in the germline of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

Common Light Chain

Prior efforts to make useful multispecific epitope-binding proteins, e.g., bispecific antibodies, have been hindered by variety of problems that frequently share a common paradigm: in vitro selection or manipulation of sequences to rationally engineer, or to engineer through trial-and-error, a suitable format for pairing a heterodimeric bispecific human immunoglobulin. Unfortunately, most if not all of the in vitro engineering approaches provide largely ad hoc fixes that are suitable, if at all, for individual molecules. On the other hand, in vivo methods for employing complex organisms to select appropriate pairings that are capable of leading to human therapeutics have not been realized.

Generally, native mouse sequences are frequently not a good source for human therapeutic sequences. For at least that reason, generating mouse heavy chain immunoglobulin variable regions that pair with a common human light chain is of limited practical utility. More in vitro engineering efforts would be expended in a trial-and-error process to try to humanize the mouse heavy chain variable sequences while hoping to retain epitope specificity and affinity while maintaining the ability to couple with the common human light chain, with uncertain outcome. At the end of such a process, the final product may maintain some of the specificity and affinity, and associate with the common light chain, but ultimately immunogenicity in a human would likely remain a profound risk.

Therefore, a suitable mouse for making human therapeutics would include a suitably large repertoire of human heavy chain variable region gene segments in place of endogenous mouse heavy chain variable region gene segments. The human heavy chain variable region gene segments should be able to rearrange and recombine with an endogenous mouse heavy chain constant domain to form a reverse chimeric heavy chain (i.e., a heavy chain comprising a human variable domain and a mouse constant region). The heavy chain should be capable of class switching and somatic hypermutation so that a suitably large repertoire of heavy chain variable domains are available for the mouse to select one that can associate with the limited repertoire of human light chain variable regions.

A mouse that selects a common light chain for a plurality of heavy chains has a practical utility. In various embodiments, antibodies that express in a mouse that can only express a common light chain will have heavy chains that can associate and express with an identical or substantially identical light chain. This is particularly useful in making bispecific antibodies. For example, such a mouse can be immunized with a first immunogen to generate a B cell that expresses an antibody that specifically binds a first epitope. The mouse (or a mouse genetically the same) can be immunized with a second immunogen to generate a B cell that expresses an antibody that specifically binds the second epitope. Variable heavy regions can be cloned from the B cells and expresses with the same heavy chain constant region, and the same light chain, and expressed in a cell to make a bispecific antibody, wherein the light chain component of the bispecific antibody has been selected by a mouse to associate and express with the light chain component.

The inventors have engineered a mouse for generating immunoglobulin light chains that will suitably pair with a rather diverse family of heavy chains, including heavy chains whose variable regions depart from germline sequences, e.g., affinity matured or somatically mutated variable regions. In various embodiments, the mouse is devised to pair human light chain variable domains with human heavy chain variable domains that comprise somatic mutations, thus enabling a route to high affinity binding proteins suitable for use as human therapeutics.

The genetically engineered mouse, through the long and complex process of antibody selection within an organism, makes biologically appropriate choices in pairing a diverse collection of human heavy chain variable domains with a limited number of human light chain options. In order to achieve this, the mouse is engineered to present a limited number of human light chain variable domain options in conjunction with a wide diversity of human heavy chain variable domain options. Upon challenge with an immunogen, the mouse maximizes the number of solutions in its repertoire to develop an antibody to the immunogen, limited largely or solely by the number or light chain options in its repertoire. In various embodiments, this includes allowing the mouse to achieve suitable and compatible somatic mutations of the light chain variable domain that will nonetheless be compatible with a relatively large variety of human heavy chain variable domains, including in particular somatically mutated human heavy chain variable domains.

To achieve a limited repertoire of light chain options, the mouse is engineered to render nonfunctional or substantially nonfunctional its ability to make, or rearrange, a native mouse light chain variable domain. This can be achieved, e.g., by deleting the mouse's light chain variable region gene segments. The endogenous mouse locus can then be modified by an exogenous suitable human light chain variable region gene segment of choice, operably linked to the endogenous mouse light chain constant domain, in a manner such that the exogenous human variable region gene segments can rearrange and recombine with the endogenous mouse light chain constant region gene and form a rearranged reverse chimeric light chain gene (human variable, mouse constant). In various embodiments, the light chain variable region is capable of being somatically mutated. In various embodiments, to maximize ability of the light chain variable region to acquire somatic mutations, the appropriate enhancer(s) is retained in the mouse. For example, in modifying a mouse κ locus to replace endogenous mouse κ variable region gene segments with human κ variable region gene segments, the mouse κ intronic enhancer and mouse κ 3' enhancer are functionally maintained, or undisrupted.

A genetically engineered mouse is provided that expresses a limited repertoire of reverse chimeric (human variable, mouse constant) light chains associated with a diversity of reverse chimeric (human variable, mouse constant) heavy chains. In various embodiments, the endogenous mouse κ light chain variable region gene segments are deleted and replaced with a single (or two) human light chain variable region gene segments, operably linked to the endogenous mouse κ constant region gene. In embodiments for maximizing somatic hypermutation of the human light chain variable region gene segments, the mouse κ intronic enhancer and the mouse κ 3' enhancer are maintained. In various embodiments, the mouse also comprises a nonfunctional λ light chain locus, or a deletion thereof or a deletion that renders the locus unable to make λ light chain.

A genetically engineered mouse is provided that, in various embodiments, comprises a light chain variable region locus lacking an endogenous mouse light chain variable gene segment and comprising a human variable gene segment, in one embodiment a rearranged human V/J sequence, operably linked to a mouse constant region, wherein the locus is capable of undergoing somatic hypermutation, and wherein the locus expresses a light chain comprising the human V/J sequence linked to a mouse constant region. Thus, in various embodiments, the locus comprises a mouse κ 3' enhancer, which is correlated with a normal, or wild-type, level of somatic hypermutation.

The genetically engineered mouse in various embodiments when immunized with an antigen of interest generates B cells that exhibit a diversity of rearrangements of human immunoglobulin heavy chain variable regions that express and function with one or with two rearranged light chains, including embodiments where the one or two light chains comprise human light chain variable regions that comprise, e.g., 1 to 5 somatic mutations. In various embodiments, the human light chains so expressed are capable of associating and expressing with any human immunoglobulin heavy chain variable region expressed in the mouse.

Epitope-Binding Proteins Binding More Than One Epitope

The compositions and methods of described herein can be used to make binding proteins that bind more than one epitope with high affinity, e.g., bispecific antibodies. Advantages of the invention include the ability to select suitably high binding (e.g., affinity matured) heavy chain immunoglobulin chains each of which will associate with a single light chain.

Synthesis and expression of bispecific binding proteins has been problematic, in part due to issues associated with identifying a suitable light chain that can associate and express with two different heavy chains, and in part due to isolation issues. The methods and compositions described herein allow for a genetically modified mouse to select, through otherwise natural processes, a suitable light chain that can associate and express with more than one heavy chain, including heavy chains that are somatically mutated (e.g., affinity matured). Human VL and VH sequences from suitable B cells of immunized mice as described herein that express affinity matured antibodies having reverse chimeric heavy chains (i.e., human variable and mouse constant) can be identified and cloned in frame in an expression vector with a suitable human constant region gene sequence (e.g., a human IgG1). Two such constructs can be prepared, wherein each construct encodes a human heavy chain variable domain that binds a different epitope. One of the human VLs (e.g., human Vκ1-39Jκ5 or human Vκ3-20Jκ1), in germline sequence or from a B cell wherein the sequence has been somatically mutated, can be fused in frame to a suitable human constant region gene (e.g., a human κ constant gene). These three fully-human heavy and light constructs can be placed in a suitable cell for expression. The cell will express two major species: a homodimeric heavy chain with the identical light chain, and a heterodimeric heavy chain with the identical light chain. To allow for a facile separation of these major species, one of the heavy chains is modified to omit a Protein A-binding determinant, resulting in a differential affinity of a homodimeric binding protein from a heterodimeric binding protein. Compositions and methods that address this issue are described in U.S. Ser. No. 12/832,838, filed 25 Jun. 20010, entitled "Readily Isolated Bispecific Antibodies with Native Immunoglobulin Format," published as US 2010/0331527A1, hereby incorporated by reference.

In one aspect, an epitope-binding protein as described herein is provided, wherein human VL and VH sequences are derived from mice described herein that have been immunized with an antigen comprising an epitope of interest.

In one embodiment, an epitope-binding protein is provided that comprises a first and a second polypeptide, the first polypeptide comprising, from N-terminal to C-terminal, a first epitope-binding region that selectively binds a first epitope, followed by a constant region that comprises a first CH3 region of a human IgG selected from IgG1, IgG2, IgG4, and a combination thereof; and, a second polypeptide comprising, from N-terminal to C-terminal, a second epitope-binding region that selectively binds a second epitope, followed by a constant region that comprises a second CH3 region of a human IgG selected from IgG1, IgG2, IgG4, and a combination thereof, wherein the second CH3 region comprises a modification that reduces or eliminates binding of the second CH3 domain to protein A.

In one embodiment, the second CH3 region comprises an H95R modification (by IMGT exon numbering; H435R by EU numbering). In another embodiment, the second CH3 region further comprises a Y96F modification (IMGT; Y436F by EU).

In one embodiment, the second CH3 region is from a modified human IgG1, and further comprises a modification selected from the group consisting of D16E, L18M, N44S, K52N, V57M, and V82I (IMGT; D356E, L358M, N384S, K392N, V397M, and V422I by EU).

In one embodiment, the second CH3 region is from a modified human IgG2, and further comprises a modification selected from the group consisting of N44S, K52N, and V82I (IMGT; N384S, K392N, and V422I by EU).

In one embodiment, the second CH3 region is from a modified human IgG4, and further comprises a modification selected from the group consisting of Q15R, N44S, K52N, V57M, R69K, E79Q, and V82I (IMGT; Q355R, N384S, K392N, V397M, R409K, E419Q, and V422I by EU).

One method for making an epitope-binding protein that binds more than one epitope is to immunize a first mouse in accordance with the invention with an antigen that comprises a first epitope of interest, wherein the mouse comprises an endogenous immunoglobulin light chain variable region locus that does not contain an endogenous mouse VL that is capable of rearranging and forming a light chain, wherein at the endogenous mouse immunglobulin light chain variable region locus is a single human VL gene segment operably linked to the mouse endogenous light chain constant region gene, and the human VL gene segment is selected from a human Vκ1-39Jκ5 and a human Vκ3-20JκK1, and the endogenous mouse VH gene segments have been replaced in whole or in part with human VH gene segments, such that immunoglobulin heavy chains made by the mouse are solely or substantially heavy chains that comprise human variable domains and mouse constant domains. When immunized, such a mouse will make a reverse chimeric antibody, comprising only one of two human light chain variable domains (e.g., one of human VκK1-39Jκ5 or human Vκ3-20Jκ1). Once a B cell is identified that encodes a VH that binds the epitope of interest, the nucleotide sequence of the VH (and, optionally, the VL) can be retrieved (e.g., by PCR) and cloned into an expression construct in frame with a suitable human immunoglobulin constant domain. This process can be repeated to identify a second VH domain that binds a second epitope, and a second VH gene sequence can be retrieved and cloned into an expression vector in frame to a second suitable immunoglobulin constant domain. The first and the second immunoglobulin constant domains can the same or different isotype, and one of the immunoglobulin constant domains (but not the other) can be modified as described herein or in US 2010/0331527A1, and epitope-binding protein can be expressed in a suitable cell and isolated based on its differential affinity for Protein A as compared to a homodimeric epitope-binding protein, e.g., as described in US 2010/0331527A1.

In one embodiment, a method for making a bispecific epitope-binding protein is provided, comprising identifying a first affinity-matured (e.g., comprising one or more somatic hypermutations) human VH nucleotide sequence (VH1) from a mouse as described herein, identifying a second affinity-matured (e.g., comprising one or more somatic hypermutations) human VH nucleotide sequence (VH2) from a mouse as described herein, cloning VH1 in frame with a human heavy chain lacking a Protein A-determinant modification as described in US 2010/0331527A1 for form heavy chain 1 (HC1), cloning VH2 in frame with a human heavy chain comprising a Protein A-determinant as described in US 2010/0331527A1 to form heavy chain 2 (HC2), introducing an expression vector comprising HC1 and the same or a different expression vector comprising HC2 into a cell, wherein the cell also expresses a human immunoglobulin light chain that comprises a human Vκ1-39/human Jκ5 or a human Vκ3-20/human Jκ1 fused to a human light chain constant domain, allowing the cell to express a bispecific epitope-binding protein comprising a VH domain encoded by VH1 and a VH domain encoded by VH2, and isolating the bispecific epitope-binding protein based on its differential ability to bind Protein A as compared with a monospecific homodimeric epitope-binding protein. In a specific embodiment, HC1 is an IgG1, and HC2 is an IgG1 that comprises the modification H95R (IMGT; H435R by EU) and further comprises the modification Y96F (IMGT; Y436F by EU). In one embodiment, the VH domain encoded by VH1, the VH domain encoded by VH2, or both, are somatically mutated.

Human VH Genes That Express with a Common Human VL

A variety of human variable regions from affinity-matured antibodies raised against four different antigens were expressed with either their cognate light chain, or at least one of a human light chain selected from human Vκ1-39Jκ5, human Vκ3-20Jκ1, or human VpreBJλ5 (see Example 1). For antibodies to each of the antigens, somatically mutated high affinity heavy chains from different gene families paired successfully with rearranged human germline Vκ1-39Jκ5 and Vκ3-20Jκ1 regions and were secreted from cells expressing the heavy and light chains. For Vκ1-39Jκ5 and Vκ3-20Jκ1, VH domains derived from the following human VH families expressed favorably: 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, and 6-1. Thus, a mouse that is engineered to express a limited repertoire of human VL domains from one or both of Vκ1-39Jκ5 and Vκ3-20Jκ1 will generate a diverse population of somatically mutated human VH domains from a VH locus modified to replace mouse VH gene segments with human VH gene segments.

Mice genetically engineered to express reverse chimeric (human variable, mouse constant) immunoglobulin heavy chains associated with a single rearranged light chain (e.g., a Vκ1-39/J or a Vκ3-20/J), when immunized with an antigen of interest, generated B cells that comprised a diversity of human V segment rearrangements and expressed a diversity of high-affinity antigen-specific antibodies with diverse properties with respect to their ability to block binding of the antigen to its ligand, and with respect to their ability to bind variants of the antigen (see Examples 5 through 10).

Thus, the mice and methods described herein are useful in making and selecting human immunoglobulin heavy chain variable domains, including somatically mutated human heavy chain variable domains, that result from a diversity of rearrangements, that exhibit a wide variety of affinities (including exhibiting a $K_D$ of about a nanomolar or less), a wide variety of specificities (including binding to different epitopes of the same antigen), and that associate and express with the same or substantially the same human immunoglobulin light chain variable region.

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is indicated in Celsius, and pressure is at or near atmospheric.

EXAMPLES

Example 1. Identification of Human Heavy Chain Variable Regions that Associate with Selected Human Light Chain Variable Regions An in vitro expression system was constructed to determine if a single rearranged human germline light chain could be co-expressed with human heavy chains from antigen specific human antibodies.

Methods for generating human antibodies in genetically modified mice are known (see e.g., U.S. Pat. No. 6,596,541, Regeneron Pharmaceuticals, VELOCIMMUNE®). The VELOCIMMUNE® technology involves generation of a genetically modified mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibodies produced from a VELOCIMMUNE® mouse are fully human. Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate a fully human antibody containing a non-IgM isotype, for example, wild-type or modified IgG1, IgG2, IgG3 or IgG4. While the constant region selected may vary according to specific use, high affinity antigen-binding and target specificity characteristics reside in the variable region.

A VELOCIMMUNE® mouse was immunized with a growth factor that promotes angiogenesis (Antigen C) and antigen-specific human antibodies were isolated and sequenced for V gene usage using standard techniques recognized in the art. Selected antibodies were cloned onto human heavy and light chain constant regions and 69 heavy chains were selected for pairing with one of three human light chains: (1) the cognate κ light chain linked to a human κ constant region, (2) a rearranged human germline Vκ1-39Jκ5 linked to a human κ constant region, or (3) a rearranged human germline Vκ3-20Jκ1 linked to a human κ constant region. Each heavy chain and light chain pair were co-transfected in CHO-K1 cells using standard techniques. Presence of antibody in the supernatant was detected by anti-human IgG in an ELISA assay. Antibody titer (ng/ml) was determined for each heavy chain/light chain pair and titers with the different rearranged germline light chains were compared to the titers obtained with the parental antibody molecule (i.e., heavy chain paired with cognate light chain) and percent of native titer was calculated (Table 1). $V_H$: Heavy chain variable gene. ND: no expression detected under current experimental conditions.

TABLE 1

| $V_H$ | Antibody Titer (ng/ml) Cognate LC | Vκ1-39Jκ5 | Vκ3-20Jκ1 | Percent of Native Titer Vκ1-39Jκ5 | Vκ3-20Jκ1 |
|---|---|---|---|---|---|
| 3-15 | 63 | 23 | 11 | 36.2 | 17.5 |
| 1-2 | 103 | 53 | ND | 51.1 | — |
| 3-23 | 83 | 60 | 23 | 72.0 | 27.5 |
| 3-33 | 15 | 77 | ND | 499.4 | — |
| 4-31 | 22 | 69 | 17 | 309.4 | 76.7 |
| 3-7 | 53 | 35 | 28 | 65.2 | 53.1 |
| — | 22 | 32 | 19 | 148.8 | 89.3 |
| 1-24 | 3 | 13 | ND | 455.2 | — |
| 3-33 | 1 | 47 | ND | 5266.7 | — |
| 3-33 | 58 | 37 | ND | 63.1 | — |
| — | 110 | 67 | 18 | 60.6 | 16.5 |
| 3-23 | 127 | 123 | 21 | 96.5 | 16.3 |
| 3-33 | 28 | 16 | 2 | 57.7 | 7.1 |
| 3-23 | 32 | 50 | 38 | 157.1 | 119.4 |
| — | 18 | 45 | 18 | 254.3 | 101.7 |
| 3-9 | 1 | 30 | 23 | 2508.3 | 1900.0 |
| 3-11 | 12 | 26 | 6 | 225.9 | 48.3 |
| 1-8 | 16 | ND | 13 | — | 81.8 |
| 3-33 | 54 | 81 | 10 | 150.7 | 19.1 |
| — | 34 | 9 | ND | 25.9 | — |
| 3-20 | 7 | 14 | 54 | 203.0 | 809.0 |
| 3-33 | 19 | 38 | ND | 200.5 | — |
| 3-11 | 48 | ND | 203 | — | 423.6 |
| — | 11 | 23 | 8 | 212.7 | 74.5 |
| 3-33 | 168 | 138 | 182 | 82.0 | 108.2 |
| 3-20 | 117 | 67 | 100 | 57.5 | 86.1 |
| 3-23 | 86 | 61 | 132 | 70.7 | 154.1 |
| 3-33 | 20 | 12 | 33 | 60.9 | 165.3 |
| 4-31 | 69 | 92 | 52 | 133.8 | 75.0 |
| 3-23 | 87 | 78 | 62 | 89.5 | 71.2 |
| 1-2 | 31 | 82 | 51 | 263.0 | 164.6 |
| 3-23 | 53 | 93 | 151 | 175.4 | 285.4 |
| — | 11 | 8 | 17 | 75.7 | 151.4 |
| 3-33 | 114 | 36 | 27 | 31.6 | 23.4 |
| 3-15 | 73 | 39 | 44 | 53.7 | 59.6 |
| 3-33 | 1 | 34 | 16 | 5600.0 | 2683.3 |
| 3-9 | 58 | 112 | 57 | 192.9 | 97.6 |
| 3-33 | 67 | 20 | 105 | 30.1 | 157.0 |
| 3-33 | 34 | 21 | 24 | 62.7 | 70.4 |
| 3-20 | 10 | 49 | 91 | 478.4 | 888.2 |
| 3-33 | 66 | 32 | 25 | 48.6 | 38.2 |
| 3-23 | 17 | 59 | 56 | 342.7 | 329.8 |
| — | 58 | 108 | 19 | 184.4 | 32.9 |
| — | 68 | 54 | 20 | 79.4 | 29.9 |
| 3-33 | 42 | 35 | 32 | 83.3 | 75.4 |
| — | 29 | 19 | 13 | 67.1 | 43.9 |
| 3-9 | 24 | 34 | 29 | 137.3 | 118.4 |
| 3-30/33 | 17 | 33 | 7 | 195.2 | 43.1 |
| 3-7 | 25 | 70 | 74 | 284.6 | 301.6 |
| 3-33 | 87 | 127 | ND | 145.1 | — |
| 6-1 | 28 | 56 | ND | 201.8 | — |
| 3-33 | 56 | 39 | 20 | 69.9 | 36.1 |
| 3-33 | 10 | 53 | 1 | 520.6 | 6.9 |
| 3-33 | 20 | 67 | 10 | 337.2 | 52.3 |
| 3-33 | 11 | 36 | 18 | 316.8 | 158.4 |
| 3-23 | 12 | 42 | 32 | 356.8 | 272.9 |
| 3-33 | 66 | 95 | 15 | 143.6 | 22.5 |
| 3-15 | 55 | 68 | ND | 123.1 | — |
| — | 32 | 68 | 3 | 210.9 | 10.6 |
| 1-8 | 28 | 48 | ND | 170.9 | — |
| 3-33 | 124 | 192 | 21 | 154.3 | 17.0 |
| 3-33 | 0 | 113 | ND | 56550.0 | — |
| 3-33 | 10 | 157 | 1 | 1505.8 | 12.5 |
| 3-33 | 6 | 86 | 15 | 1385.5 | 243.5 |
| 3-23 | 70 | 115 | 22 | 163.5 | 31.0 |
| 3-7 | 71 | 117 | 21 | 164.6 | 29.6 |
| 3-33 | 82 | 100 | 47 | 122.7 | 57.1 |
| 3-7 | 124 | 161 | 41 | 130.0 | 33.5 |

In a similar experiment, VELOCIMMUNE® mice were immunized with several different antigens and selected heavy chains of antigen specific human antibodies were tested for their ability to pair with different rearranged human germline light chains (as described above). The antigens used in this experiment included an enzyme involved in cholesterol homeostasis (Antigen A), a serum hormone involved in regulating glucose homeostasis (Antigen B), a growth factor that promotes angiogenesis (Antigen C) and a cell-surface receptor (Antigen D). Antigen specific antibodies were isolated from mice of each immunization group and the heavy chain and light chain variable regions were cloned and sequenced. From the sequence of the heavy and light chains, V gene usage was determined and selected heavy chains were paired with either their cognate light chain or a rearranged human germline Vκ1-39Jκ5 region. Each heavy/light chain pair was co-transfected in CHO-K1 cells and the presence of antibody in the supernatant was detected by anti-human IgG in an ELISA assay. Antibody titer (μg/ml) was determined for each heavy chain/light chain pairing and titers with the different rearranged human germline light chains were compared to the titers obtained with the parental antibody molecule (i.e., heavy chain paired with cognate light chain) and percent of native titer was calculated (Table 2). $V_H$: Heavy chain variable gene. Vκ: κ light chain variable gene. ND: no expression detected under current experimental conditions.

TABLE 2

| Antigen | Antibody | $V_H$ | Vκ | Titer (μg/ml) $V_H$ Alone | $V_H$ + Vκ | $V_H$ + Vκ1-39Jκ5 | Percent of Native Titer |
|---|---|---|---|---|---|---|---|
| A | 320 | 1-18 | 2-30 | 0.3 | 3.1 | 2.0 | 66 |
|  | 321 | 2-5 | 2-28 | 0.4 | 0.4 | 1.9 | 448 |
|  | 334 | 2-5 | 2-28 | 0.4 | 2.7 | 2.0 | 73 |
|  | 313 | 3-13 | 3-15 | 0.5 | 0.7 | 4.5 | 670 |
|  | 316 | 3-23 | 4-1 | 0.3 | 0.2 | 4.1 | 2174 |
|  | 315 | 3-30 | 4-1 | 0.3 | 0.2 | 3.2 | 1327 |
|  | 318 | 4-59 | 1-17 | 0.3 | 4.6 | 4.0 | 86 |
| B | 257 | 3-13 | 1-5 | 0.4 | 3.1 | 3.2 | 104 |
|  | 283 | 3-13 | 1-5 | 0.4 | 5.4 | 3.7 | 69 |
|  | 637 | 3-13 | 1-5 | 0.4 | 4.3 | 3.0 | 70 |
|  | 638 | 3-13 | 1-5 | 0.4 | 4.1 | 3.3 | 82 |
|  | 624 | 3-23 | 1-17 | 0.3 | 5.0 | 3.9 | 79 |
|  | 284 | 3-30 | 1-17 | 0.3 | 4.6 | 3.4 | 75 |
|  | 653 | 3-33 | 1-17 | 0.3 | 4.3 | 0.3 | 7 |

TABLE 2-continued

| Antigen | Antibody | $V_H$ | Vκ | $V_H$ Alone | $V_H$ + Vκ | $V_H$ + Vκ1-39Jκ5 | Percent of Native Titer |
|---|---|---|---|---|---|---|---|
| | 268 | 4-34 | 1-27 | 0.3 | 5.5 | 3.8 | 69 |
| | 633 | 4-34 | 1-27 | 0.6 | 6.9 | 3.0 | 44 |
| C | 730 | 3-7 | 1-5 | 0.3 | 1.1 | 2.8 | 249 |
| | 728 | 3-7 | 1-5 | 0.3 | 2.0 | 3.2 | 157 |
| | 691 | 3-9 | 3-20 | 0.3 | 2.8 | 3.1 | 109 |
| | 749 | 3-33 | 3-15 | 0.3 | 3.8 | 2.3 | 62 |
| | 750 | 3-33 | 1-16 | 0.3 | 3.0 | 2.8 | 92 |
| | 724 | 3-33 | 1-17 | 0.3 | 2.3 | 3.4 | 151 |
| | 706 | 3-33 | 1-16 | 0.3 | 3.6 | 3.0 | 84 |
| | 744 | 1-18 | 1-12 | 0.4 | 5.1 | 3.0 | 59 |
| | 696 | 3-11 | 1-16 | 0.4 | 3.0 | 2.9 | 97 |
| | 685 | 3-13 | 3-20 | 0.3 | 0.5 | 3.4 | 734 |
| | 732 | 3-15 | 1-17 | 0.3 | 4.5 | 3.2 | 72 |
| | 694 | 3-15 | 1-5 | 0.4 | 5.2 | 2.9 | 55 |
| | 743 | 3-23 | 1-12 | 0.3 | 3.2 | 0.3 | 10 |
| | 742 | 3-23 | 2-28 | 0.4 | 4.2 | 3.1 | 74 |
| | 693 | 3-23 | 1-12 | 0.5 | 4.2 | 4.0 | 94 |
| D | 136 | 3-23 | 2-28 | 0.4 | 5.0 | 2.7 | 55 |
| | 155 | 3-30 | 1-16 | 0.4 | 1.0 | 2.2 | 221 |
| | 163 | 3-30 | 1-16 | 0.3 | 0.6 | 3.0 | 506 |
| | 171 | 3-30 | 1-16 | 0.3 | 1.0 | 2.8 | 295 |
| | 145 | 3-43 | 1-5 | 0.4 | 4.4 | 2.9 | 65 |
| | 49 | 3-48 | 3-11 | 0.3 | 1.7 | 2.6 | 155 |
| | 51 | 3-48 | 1-39 | 0.1 | 1.9 | 0.1 | 4 |
| | 159 | 3-7 | 6-21 | 0.4 | 3.9 | 3.6 | 92 |
| | 169 | 3-7 | 6-21 | 0.3 | 1.3 | 3.1 | 235 |
| | 134 | 3-9 | 1-5 | 0.4 | 5.0 | 2.9 | 58 |
| | 141 | 4-31 | 1-33 | 2.4 | 4.2 | 2.6 | 63 |
| | 142 | 4-31 | 1-33 | 0.4 | 4.2 | 2.8 | 67 |

The results obtained from these experiments demonstrate that somatically mutated, high affinity heavy chains from different gene families are able to pair with rearranged human germline Vκ1-39Jκ5 and Vκ3-20Jκ1 regions and be secreted from the cell as a normal antibody molecule. As shown in Table 1, antibody titer was increased for about 61% (42 of 69) heavy chains when paired with the rearranged human Vκ1-39Jκ5 light chain and about 29% (20 of 69) heavy chains when paired with the rearranged human Vκ3-20Jκ1 light chain as compared to the cognate light chain of the parental antibody. For about 20% (14 of 69) of the heavy chains, both rearranged human germline light chains conferred an increase in expression as compared to the cognate light chain of the parental antibody. As shown in Table 2, the rearranged human germline Vκ1-39Jκ5 region conferred an increase in expression of several heavy chains specific for a range of different classes of antigens as compared to the cognate light chain for the parental antibodies. Antibody titer was increased by more than two-fold for about 35% (15/43) of the heavy chains as compared to the cognate light chain of the parental antibodies. For two heavy chains (315 and 316), the increase was greater than ten-fold as compared to the parental antibody. Within all the heavy chains that showed increase expression relative to the cognate light chain of the parental antibody, family three ($V_H$3) heavy chains are over represented in comparison to other heavy chain variable region gene families. This demonstrates a favorable relationship of human $V_H$3 heavy chains to pair with rearranged human germline Vκ1-39Jκ5 and Vκ3-20Jκ1 light chains.

Example 2. Generation of a Rearranged Human Germline Light Chain Locus

Various rearranged human germline light chain targeting vectors were made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659) to modify mouse genomic Bacterial Artificial Chromosome (BAC) clones 302g12 and 254m04 (Invitrogen). Using these two BAC clones, genomic constructs were engineered to contain a single rearranged human germline light chain region and inserted into an endogenous κ light chain locus that was previously modified to delete the endogenous κ variable and joining gene segments.

A. Construction of Rearranged Human Germline Light Chain Targeting Vectors

Three different rearranged human germline light chain regions were made using standard molecular biology techniques recognized in the art. The human variable gene segments used for constructing these three regions included rearranged human Vκ1-39Jκ5 sequence, a rearranged human Vκ3-20Jδ1 sequence and a rearranged human VpreBJλ5 sequence.

A DNA segment containing exon 1 (encoding the leader peptide) and intron 1 of the mouse Vκ3-7 gene was made by de novo DNA synthesis (Integrated DNA Technologies). Part of the 5' untranslated region up to a naturally occurring BlpI restriction enzyme site was included. Exons of human Vκ1-39 and Vκ3-20 genes were PCR amplified from human genomic BAC libraries. The forward primers had a 5' extension containing the splice acceptor site of intron 1 of the mouse Vκ3-7 gene. The reverse primer used for PCR of the human Vκ1-39 sequence included an extension encoding human Jκ5, whereas the reverse primer used for PCR of the human Vκ3-20 sequence included an extension encoding human Jκ1. The human VpreBJλ5 sequence was made by de novo DNA synthesis (Integrated DNA Technologies). A portion of the human Jκ-Cκ intron including the splice donor site was PCR amplified from plasmid pBS-296-HA18-PISceI. The forward PCR primer included an extension encoding part of either a human Jκ5, Jκ1, or Jκ5 sequence. The reverse primer included a PI-SceI site, which was previously engineered into the intron.

The mouse Vκ3-7 exon1/intron 1, human variable light chain exons, and human Jκ-Cκ intron fragments were sewn together by overlap extension PCR, digested with BlpI and PI-SceI, and ligated into plasmid pBS-296-HA18-PISceI, which contained the promoter from the human Vκ3-15 variable gene segment. A loxed hygromycin cassette within plasmid pBS-296-HA18-PISceI was replaced with a FRTed hygromycin cassette flanked by NotI and AscI sites. The NotI/PI-SceI fragment of this plasmid was ligated into modified mouse BAC 254m04, which contained part of the mouse Jκ-Cκ intron, the mouse Cκ exon, and about 75 kb of genomic sequence downstream of the mouse κ locus which provided a 3' homology arm for homologous recombination in mouse ES cells. The NotI/AscI fragment of this BAC was then ligated into modified mouse BAC 302g12, which contained a FRTed neomycin cassette and about 23 kb of genomic sequence upstream of the endogenous κ locus for homologous recombination in mouse ES cells.

B. Rearranged Human Germline Vκ1-39Jκ5 Targeting Vector (FIG. 1)

Restriction enzyme sites were introduced at the 5' and 3' ends of an engineered light chain insert for cloning into a targeting vector: an AscI site at the 5' end and a PI-SceI site at the 3' end. Within the 5' AscI site and the 3' PI-SceI site the targeting construct from 5' to 3' included a 5' homology arm containing sequence 5' to the endogenous mouse κ light chain locus obtained from mouse BAC clone 302g12, a FRTed neomycin resistance gene, an genomic sequence including the human Vκ3-15 promoter, a leader sequence of the mouse Vκ3-7 variable gene segment, a intron sequence of the mouse Vκ3-7 variable gene segment, an open reading frame of a rearranged human germline Vκ1-39Jκ5 region, a genomic sequence containing a portion of the human Jκ-Cκ intron, and a 3' homology arm containing sequence 3' of the endogenous mouse Jκ5 gene segment obtained from mouse BAC clone 254m04 (FIG. 1, middle). Genes and/or sequences upstream of the endogenous mouse κ light chain locus and downstream of the most 3' Jκ gene segment (e.g., the endogenous 3' enhancer) were unmodified by the targeting construct (see FIG. 1). The sequence of the engineered human Vκ1-39Jκ5 locus is shown in SEQ ID NO:1.

Targeted insertion of the rearranged human germline Vκ1-39Jκ5 region into BAC DNA was confirmed by polymerase chain reaction (PCR) using primers located at sequences within the rearranged human germline light chain region. Briefly, the intron sequence 3' to the mouse Vκ3-7 leader sequence was confirmed with primers ULC-m1F (AGGTGAGGGT ACAGATAAGT GTTATGAG; SEQ ID NO:2) and ULC-m1R (TGACAAATGC CCTAATTATA GTGATCA; SEQ ID NO:3). The open reading frame of the rearranged human germline Vκ1-39Jκ5 region was confirmed with primers 1633-h2F (GGGCAAGTCA GAGCATTAGC A; SEQ ID NO:4) and 1633-h2R (TGCAAACTGG ATGCAGCATA G; SEQ ID NO:5). The neomycin cassette was confirmed with primers neoF (GGTGGAGAGG CTATTCGGC; SEQ ID NO:6) and neoR (GAACACGGCG GCATCAG; SEQ ID NO:7). Targeted BAC DNA was then used to electroporate mouse ES cells to created modified ES cells for generating chimeric mice that express a rearranged human germline Vκ1-39Jκ5 region.

Positive ES cell clones were confirmed by TAQMAN™ screening and karyotyping using probes specific for the engineered Vκ1-39Jκ5 light chain region inserted into the endogenous locus. Briefly, probe neoP (TGGGCACAAC AGACAATCGG CTG; SEQ ID NO:8) which binds within the neomycin marker gene, probe ULC-m1P (CCATTAT-GAT GCTCCATGCC TCTCTGTTC; SEQ ID NO:9) which binds within the intron sequence 3' to the mouse Vκ3-7 leader sequence, and probe 1633h2P (ATCAGCAGAA ACCAGGGAAA GCCCCT; SEQ ID NO:10) which binds within the rearranged human germline Vκ1-39Jκ5 open reading frame. Positive ES cell clones were then used to implant female mice to give rise to a litter of pups expressing the germline Vκ1-39Jκ5 light chain region.

Alternatively, ES cells bearing the rearranged human germline Vκ1-39Jκ5 light chain region are transfected with a construct that expresses FLP in order to remove the FRTed neomycin cassette introduced by the targeting construct. Optionally, the neomycin cassette is removed by breeding to mice that express FLP recombinase (e.g., U.S. Pat. No. 6,774,279). Optionally, the neomycin cassette is retained in the mice C. Rearranged Human Germline Vκ3-20Jκ1 Targeting Vector (FIG. 2)

Figure 2:
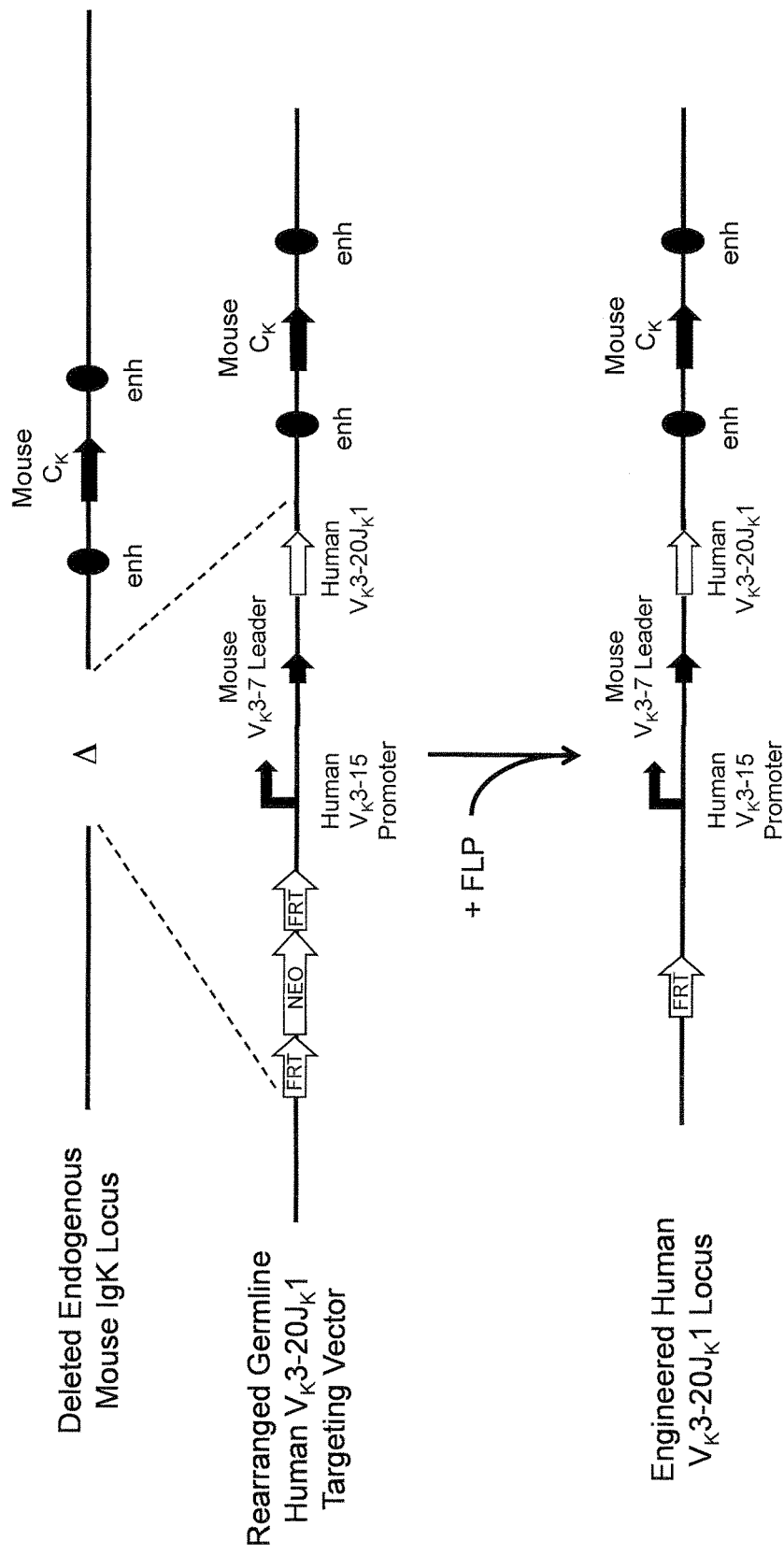
FIG. 2 illustrates a targeting strategy for replacing endogenous mouse immunoglobulin light chain variable region gene segments with a human Vκ3-20Jκ1 gene region.

In a similar fashion, an engineered light chain locus expressing a rearranged human germline Vκ3-20Jκ1 region was made using a targeting construct including, from 5' to 3', a 5' homology arm containing sequence 5' to the endogenous mouse κ light chain locus obtained from mouse BAC clone 302g12, a FRTed neomycin resistance gene, a genomic sequence including the human Vκ3-15 promoter, a leader sequence of the mouse Vκ3-7 variable gene segment, an intron sequence of the mouse Vκ3-7 variable gene segment, an open reading frame of a rearranged human germline Vκ3-20Jκ1 region, a genomic sequence containing a portion of the human Jκ-Cκ intron, and a 3' homology arm containing sequence 3' of the endogenous mouse Jκ5 gene segment obtained from mouse BAC clone 254m04 (FIG. 2, middle). The sequence of the engineered human Vκ3-20Jκ1 locus is shown in SEQ ID NO:11.

Targeted insertion of the rearranged human germline Vκ3-20Jκ1 region into BAC DNA was confirmed by polymerase chain reaction (PCR) using primers located at sequences within the rearranged human germline Vκ3-20Jκ1 light chain region. Briefly, the intron sequence 3' to the mouse Vκ3-7 leader sequence was confirmed with primers ULC-m1F (SEQ ID NO:2) and ULC-m1R (SEQ ID NO:3). The open reading frame of the rearranged human germline Vκ3-20Jκ1 region was confirmed with primers 1635-h2F (TCCAGGCACC CTGTCTTTG; SEQ ID NO:12) and 1635-h2R (AAGTAGCTGC TGCTAACACT CTGACT; SEQ ID NO:13). The neomycin cassette was confirmed with primers neoF (SEQ ID NO:6) and neoR (SEQ ID NO:7). Targeted BAC DNA was then used to electroporate mouse ES cells to created modified ES cells for generating chimeric mice that express the rearranged human germline Vκ3-20Jκ1 light chain.

Positive ES cell clones were confirmed by Taqman™ screening and karyotyping using probes specific for the engineered Vκ3-20Jκ1 light chain region inserted into the endogenous κ light chain locus. Briefly, probe neoP (SEQ ID NO:8) which binds within the neomycin marker gene, probe ULC-m1P (SEQ ID NO:9) which binds within the mouse Vκ3-7 leader sequence, and probe 1635h2P (AAAGAGC-CAC CCTCTCCTGC AGGG; SEQ ID NO:14) which binds within the human V κ3-20Jκ1 open reading frame. Positive ES cell clones were then used to implant female mice. A litter of pups expressing the human germline Vκ3-20Jκ1 light chain region.

Alternatively, ES cells bearing human germline Vκ3-20Jκ1 light chain region can be transfected with a constuct that expresses FLP in oder to remove the FRTed neomycin cassette introduced by the targeting consruct. Optionally, the neomycin cassette may be removed by breeding to mice that express FLP recombinase (e.g., U.S. Pat. No. 6,774,279). Optionally, the neomycin cassette is retained in the mice.

D. Rearranged Human Germline VpreBJλ5 Targeting Vector (FIG. 3)

Figure 3:
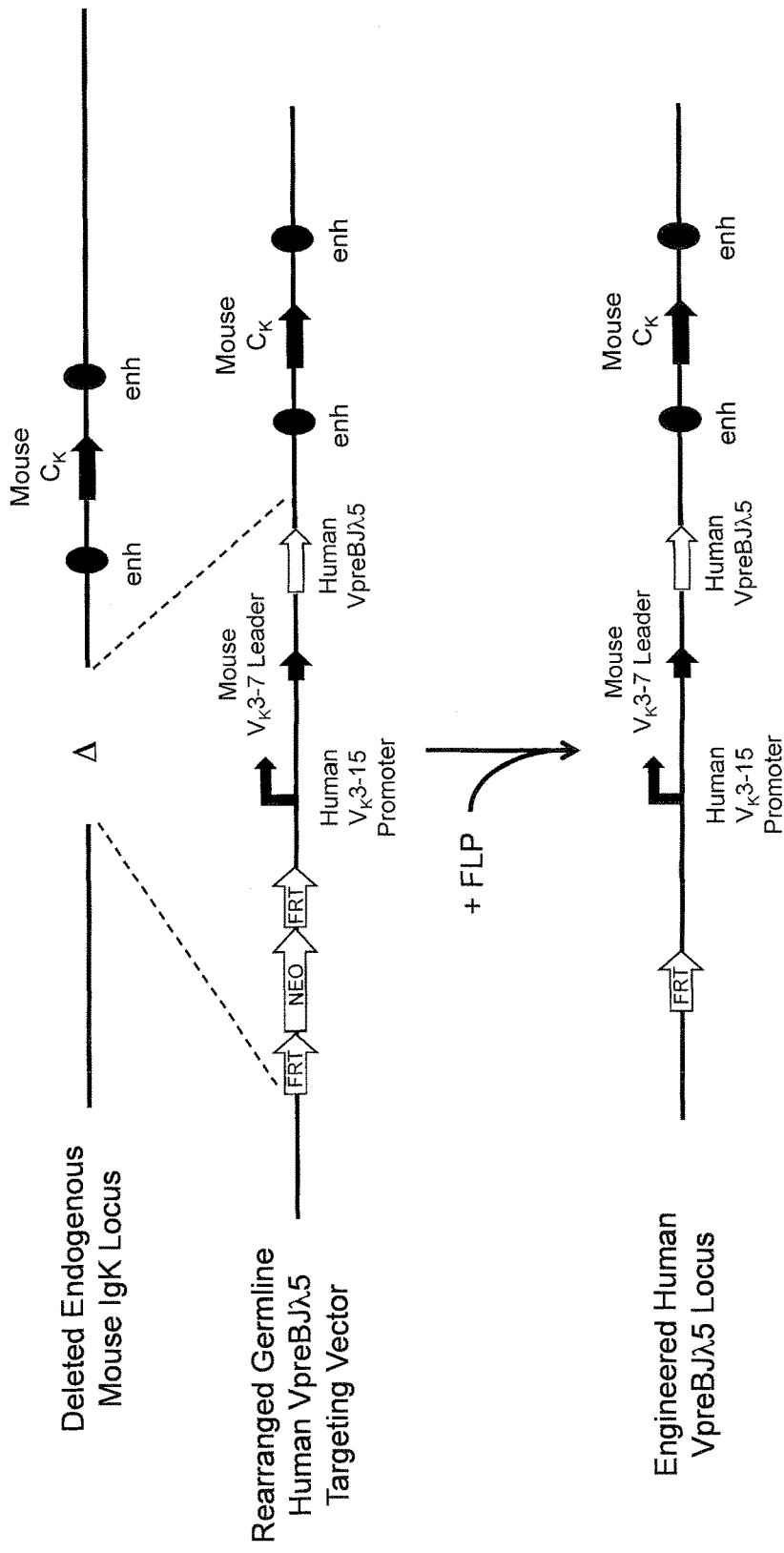
FIG. 3 illustrates a targeting strategy for replacing endogenous mouse immunoglobulin light chain variable region gene segments with a human VpreB/Jλ5 gene region.

In a similar fashion, an engineered light chain locus expressing a rearranged human germline VpreBJλ5 region was made using a targeting construct including, from 5' to 3', a 5' homology arm containing sequence 5' to the endogenous mouse κ light chain locus obtained from mouse BAC clone 302g12, a FRTed neomycin resistance gene, an genomic sequence including the human Vκ3-15 promoter, a leader sequence of the mouse Vκ3-7 variable gene segment, an intron sequence of the mouse Vκ3-7 variable gene segment, an open reading frame of a rearranged human germline VpreBJλ5 region, a genomic sequence containing a portion of the human Jκ-Cκ intron, and a 3' homology arm containing sequence 3' of the endogenous mouse Jκ5 gene segment obtained from mouse BAC clone 254m04 (FIG. 3, middle). The sequence of the engineered human VpreBJλ5 locus is shown in SEQ ID NO:15.

Targeted insertion of the rearranged human germline VpreBJλ5 region into BAC DNA was confirmed by polymerase chain reaction (PCR) using primers located at sequences within the rearranged human germline VpreBJλ5 region light chain region. Briefly, the intron sequence 3' to the mouse Vκ3-7 leader sequence was confirmed with primers ULC-m1F (SEQ ID NO:2) and ULC-m1R (SEQ ID NO:3). The open reading frame of the rearranged human germline VpreBJλ5 region was confirmed with primers 1616-h1F (TGTCCTCGGC CCTTGGA; SEQ ID NO:16) and 1616-h1R (CCGATGTCAT GGTCGTTCCT; SEQ ID NO:17). The neomycin cassette was confirmed with primers neoF (SEQ ID NO:6) and neoR (SEQ ID NO:7). Targeted BAC DNA was then used to electroporate mouse ES cells to created modified ES cells for generating chimeric mice that express the rearranged human germline VpreBJλ5 light chain.

Positive ES cell clones are confirmed by TAQMAN™ screening and karyotyping using probes specific for the engineered VpreBJλ5 light chain region inserted into the endogenous κ light chain locus. Briefly, probe neoP (SEQ ID NO:8) which binds within the neomycin marker gene, probe ULC-m1P (SEQ ID NO:9) which binds within the mouse IgVκ3-7 leader sequence, and probe 1616h1P (ACAATC-CGCC TCACCTGCAC CCT; SEQ ID NO:18) which binds within the human VpreBJλ5 open reading frame. Positive ES cell clones are then used to implant female mice to give rise to a litter of pups expressing a germline light chain region.

Alternatively, ES cells bearing the rearranged human germline VpreBJλ5 light chain region are transfected with a construct that expresses FLP in order to remove the FRTed neomycin cassette introduced by the targeting consruct. Optionally, the neomycin cassette is removed by breeding to mice that express FLP recombinase (e.g., U.S. Pat. No. 6,774,279). Optionally, the neomycin cassette is retained in the mice.

Example 3. Generation of Mice Expressing a Single Rearranged Hyuman Germline Light Chain Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® independently bearing an engineered human germline Vκ1-39Jκ5 light chain region, a Vκ3-20Jκ1 light chain region or a VpreBJλ5 light chain region are identified by genotyping using a modification of allele assay (Valenzuela et al., supra) that detects the presence of the unique rearranged human germline light chain region.

Pups are genotyped and a pup heterozygous for the unique rearranged human germline light chain region are selected for characterizing expression of the rearranged human germline light chain region.

Example 4. Breeding of Mice Expressing a Single Rearranged Human Germline Light Chain A. Endogenous 10, Knockout (KO).

To optimize the usage of the engineered light chain locus, mice bearing one of the rearranged human germline light chain regions are bred to another mouse containing a deletion in the endogenous λ light chain locus. In this manner, the progeny obtained will express, as their only light chain, the rearranged human germline light chain region as described in Example 2. Breeding is performed by standard techniques recognized in the art and, alternatively, by a commercial breeder (e.g., The Jackson Laboratory). Mouse strains bearing an engineered light chain locus and a deletion of the endogenous λ light chain locus are screened for presence of the unique light chain region and absence of endogenous mouse λ light chains.

B. Humanized Endogenous Heavy Chain Locus.

Mice bearing an engineered human germline light chain locus are bred with mice that contain a replacement of the endogenous mouse heavy chain variable gene locus with the human heavy chain variable gene locus (see U.S. Pat. No. 6,596,541; the VELOCIMMUNE® mouse, Regeneron Pharmaceuticals, Inc.). The VELOCIMMUNE® mouse comprises a genome comprising human heavy chain variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies is isolated and operably linked to DNA encoding the human heavy chain constant regions. The DNA is then expressed in a cell capable of expressing the fully human heavy chain of the antibody.

Mice bearing a replacement of the endogenous mouse VH locus with the human VH locus and a single rearranged human germline VL region at the endogenous κ light chain locus are obtained. Reverse chimeric antibodies containing somatically mutated heavy chains (human VH and mouse CH) with a single human light chain (human VL and mouse CL) are obtained upon immunization with an antigen of interest. VH and VL nucleotide sequences of B cells expressing the antibodies are identified and fully human antibodies are made by fusion the VH and VL nucleotide sequences to human CH and CL nucleotide sequences in a suitable expression system.

Example 5. Generation of Antibodies from Mice Expressing Human Heavy Chains and a Rearranged Human Germline Light Chain Region After breeding mice that contain the engineered human light chain region to various desired strains containing modifications and deletions of other endogenous Ig loci (as described in Example 4), selected mice can be immunized with an antigen of interest.

Generally, a VELOCIMMUNE® mouse containing one of the single rearranged human germline light chain regions is challenged with an antigen, and lymphatic cells (such as B-cells) are recovered from serum of the animals. The lymphatic cells are fused with a myeloma cell line to prepare immortal hybridoma cell lines, and such hybridoma cell lines are screened and selected to identify hybridoma cell lines that produce antibodies containing human heavy chain variables and a rearranged human germline light chains which are specific to the antigen used for immunization. DNA encoding the variable regions of the heavy chains and the light chain are isolated and linked to desirable isotypic constant regions of the heavy chain and light chain. Due to the presence of the endogenous mouse sequences and any additional cis-acting elements present in the endogenous locus, the single light chain of each antibody may be somatically mutated. This adds additional diversity to the antigen-specific repertoire comprising a single light chain and diverse heavy chain sequences. The resulting cloned antibody sequences are subsequently expressed in a cell, such as a CHO cell. Alternatively, DNA encoding the antigen-specific chimeric antibodies or the variable domains of the light and heavy chains are identified directly from antigen-specific lymphocytes.

Initially, high affinity chimeric antibodies are isolated having a human variable region and a mouse constant region. As described above, the antibodies are characterized and selected for desirable characteristics, including affinity, selectivity, epitope, etc. The mouse constant regions are replaced with a desired human constant region to generate the fully human antibody containing a somatically mutated human heavy chain and a single light chain derived from a rearranged human germline light chain region of the invention. Suitable human constant regions include, for example wild-type or modified IgG1 or IgG4.

Separate cohorts of VELOCIMMUNE® mice containing a replacement of the endogenous mouse heavy chain locus with human V, D, and J gene segments and a replacement of the endogenous mouse κ light chain locus with either the engineered germline Vκ1-39Jκ5 human light chain region or the engineered germline Vκ3-20Jκ1 human light chain region (described above) were immunized with a human cell-surface receptor protein (Antigen E). Antigen E is administered directly onto the hind footpad of mice with six consecutive injections every 3-4 days. Two to three micrograms of Antigen E are mixed with 10 μg of CpG oligonucleotide (Cat #tlrl-modn—ODN1826 oligonucleotide; InVivogen, San Diego, Calif.) and 25 μg of Adju-Phos (Aluminum phosphate gel adjuvant, Cat #H-71639-250; Brenntag Biosector, Frederikssund, Denmark) prior to injection. A total of six injections are given prior to the final antigen recall, which is given 3-5 days prior to sacrifice. Bleeds after the 4th and 6th injection are collected and the antibody immune response is monitored by a standard antigen-specific immunoassay.

When a desired immune response is achieved splenocytes are harvested and fused with mouse myeloma cells to preserve their viability and form hybridoma cell lines. The hybridoma cell lines are screened and selected to identify cell lines that produce Antigen E-specific common light chain antibodies. Using this technique several anti-Antigen E-specific common light chain antibodies (i.e., antibodies possessing human heavy chain variable domains, the same human light chain variable domain, and mouse constant domains) are obtained.

Alternatively, anti-Antigen E common light chain antibodies are isolated directly from antigen-positive B cells without fusion to myeloma cells, as described in U.S. 200710280945A1, herein specifically incorporated by reference in its entirety. Using this method, several fully human anti-Antigen E common light chain antibodies (i.e., antibodies possessing human heavy chain variable domains, either an engineered human Vκ1-39Jκ5 light chain or an engineered human Vκ3-20Jκ1 light chain region, and human constant domains) were obtained.

The biological properties of the exemplary anti-Antigen E common light chain antibodies generated in accordance with the methods of this Example are described in detail in the sections set forth below.

Example 6. Heavy Chain Gene Segment Usage in Antigen-Specific Common Light Chain Antibodies To analyze the structure of the human anti-Antigen E common light chain antibodies produced, nucleic acids encoding heavy chain antibody variable regions were cloned and sequenced. From the nucleic acid sequences and predicted amino acid sequences of the antibodies, gene usage was identified for the heavy chain variable region (HCVR) of selected common light chain antibodies obtained from immunized VELOCIMMUNE® mice containing either the engineered human Vκ1-39Jκ5 light chain or engineered human Vκ3-20Jκ1 light chain region. Results are shown in Tables 3 and 4, which demonstrate that mice according to the invention generate antigen-specific common light chain antibodies from a variety of human heavy chain gene segments, due to a variety of rearrangements, when employing either a mouse that expresses a light chain from only a human Vκ1-39- or a human Vκ3-20-derived light chain. Human $V_H$ gene segments of the 2, 3, 4, and 5 families rearranged with a variety of human $D_H$ segments and human $J_H$ segments to yield antigen-specific antibodies.

TABLE 3

Vκ1-39Jκ5
Common Light Chain Antibodies

| | HCVR | | |
|---|---|---|---|
| Antibody | $V_H$ | $D_H$ | $J_H$ |
| 2952 | 2-5 | 6-6 | 1 |
| 3022 | 3-23 | 3-10 | 4 |
| 3028 | 3-23 | 3-3 | 4 |
| 2955 | 3-30 | 6-6 | 1 |
| 3043 | 3-30 | 6-6 | 3 |
| 3014 | 3-30 | 1-7 | 4 |
| 3015 | 3-30 | 1-7 | 4 |
| 3023 | 3-30 | 1-7 | 4 |
| 3024 | 3-30 | 1-7 | 4 |
| 3032 | 3-30 | 1-7 | 4 |
| 3013 | 3-30 | 5-12 | 4 |
| 3042 | 3-30 | 5-12 | 4 |
| 2985 | 3-30 | 6-13 | 4 |
| 2997 | 3-30 | 6-13 | 4 |
| 3011 | 3-30 | 6-13 | 4 |
| 3047 | 3-30 | 6-13 | 4 |
| 3018 | 3-30 | 6-6 | 4 |
| 2948 | 3-30 | 7-27 | 4 |
| 2987 | 3-30 | 7-27 | 4 |
| 2996 | 3-30 | 7-27 | 4 |
| 3005 | 3-30 | 7-27 | 4 |
| 3012 | 3-30 | 7-27 | 4 |

TABLE 3-continued

Vκ1-39Jκ5
Common Light Chain Antibodies

| Antibody | HCVR | | |
|---|---|---|---|
| | $V_H$ | $D_H$ | $J_H$ |
| 3020 | 3-30 | 7-27 | 4 |
| 3021 | 3-30 | 7-27 | 4 |
| 3025 | 3-30 | 7-27 | 4 |
| 3030 | 3-30 | 7-27 | 4 |
| 3036 | 3-30 | 7-27 | 4 |
| 2982 | 3-30 | 3-22 | 5 |
| 2949 | 3-30 | 6-6 | 5 |
| 2950 | 3-30 | 6-6 | 5 |
| 2954 | 3-30 | 6-6 | 5 |
| 2978 | 3-30 | 6-6 | 5 |
| 3016 | 3-30 | 6-6 | 5 |
| 3017 | 3-30 | 6-6 | 5 |
| 3033 | 3-30 | 6-6 | 5 |
| 3041 | 3-30 | 6-6 | 5 |
| 3004 | 3-30 | 7-27 | 5 |
| 3010 | 4-59 | 3-16 | 3 |
| 3019 | 4-59 | 3-16 | 3 |
| 2964 | 4-59 | 3-22 | 3 |
| 3027 | 4-59 | 3-16 | 4 |
| 3046 | 5-51 | 5-5 | 3 |

TABLE 4

Vκ3-20Jκ1
Common Light Chain Antibodies

| Antibody | HCVR | | |
|---|---|---|---|
| | $V_H$ | $D_H$ | $J_H$ |
| 2968 | 4-39 | 1-26 | 3 |
| 2975 | 5-51 | 6-13 | 5 |
| 2972 | 5-51 | 3-16 | 6 |

Example 7. Determination of Blocking Ability of Antigen-Specific Common Light Chain Antibodies by Luminex™ Assay Ninety-eight human common light chain antibodies raised against Antigen E were tested for their ability to block binding of Antigen E's natural ligand (Ligand Y) to Antigen E in a bead-based assay.

The extracellular domain (ECD) of Antigen E was conjugated to two myc epitope tags and a 6× histidine tag (Antigen E-mmH) and amine-coupled to carboxylated microspheres at a concentration of 20 μg/mL in MES buffer. The mixture was incubated for two hours at room temperature followed by bead deactivation with 1M Tris pH 8.0 followed by washing in PBS with 0.05% (v/v) Tween-20. The beads were then blocked with PBS (Irvine Scientific, Santa Ana, Calif.) containing 2% (w/v) BSA (Sigma-Aldrich Corp., St. Louis, Mo.). In a 96-well filter plate, supernatants containing Antigen E-specific common light chain antibodies, were diluted 1:15 in buffer. A negative control containing a mock supernatant with the same media components as for the antibody supernatant was prepared. Antigen E-labeled beads were added to the supernatants and incubated overnight at 4° C. Biotinylated-Ligand Y protein was added to a final concentration of 0.06 nM and incubated for two hours at room temperature. Detection of biotinylated-Ligand Y bound to Antigen E-myc-myc-6His labeled beads was determined with R-Phycoerythrin conjugated to Streptavidin (Moss Inc, Pasadena, Md.) followed by measurement in a Luminex™ flow cytometry-based analyzer. Background Mean Fluorescence Intensity (MFI) of a sample without Ligand Y was subtracted from all samples. Percent blocking was calculated by division of the background-subtracted MFI of each sample by the adjusted negative control value, multiplying by 100 and subtracting the resulting value from 100.

In a similar experiment, the same 98 human common light chain antibodies raised against Antigen E were tested for their ability to block binding of Antigen E to Ligand Y-labeled beads.

Briefly, Ligand Y was amine-coupled to carboxylated microspheres at a concentration of 20 μg/mL diluted in MES buffer. The mixture and incubated two hours at room temperature followed by deactivation of beads with 1M Tris pH 8 then washing in PBS with 0.05% (v/v) Tween-20. The beads were then blocked with PBS (Irvine Scientific, Santa Ana, Calif.) containing 2% (w/v) BSA (Sigma-Aldrich Corp., St. Louis, Mo.). In a 96-well filter plate, supernatants containing Antigen E-specific common light chain antibodies were diluted 1:15 in buffer. A negative control containing a mock supernatant with the same media components as for the antibody supernatant was prepared. A biotinylated-Antigen E-mmH was added to a final concentration of 0.42 nM and incubated overnight at 4° C. Ligand Y-labeled beads were then added to the antibody/Antigen E mixture and incubated for two hours at room temperature. Detection of biotinylated-Antigen E-mmH bound to Ligand Y-beads was determined with R-Phycoerythrin conjugated to Streptavidin (Moss Inc, Pasadena, Md.) followed by measurement in a Luminex™ flow cytometry-based analyzer. Background Mean Fluorescence Intensity (MFI) of a sample without Antigen E was subtracted from all samples. Percent blocking was calculated by division of the background-subtracted MFI of each sample by the adjusted negative control value, multiplying by 100 and subtracting the resulting value from 100.

Tables 5 and 6 show the percent blocking for all 98 anti-Antigen E common light chain antibodies tested in both Luminex™ assays. ND: not determined under current experimental conditions.

In the first Luminex™ experiment described above, 80 common light chain antibodies containing the Vκ1-39Jκ5 engineered light chain were tested for their ability to block Ligand Y binding to Antigen E-labeled beads. Of these 80 common light chain antibodies, 68 demonstrated >50% blocking, while 12 demonstrated <50% blocking (6 at 25-50% blocking and 6 at <25% blocking). For the 18 common light chain antibodies containing the Vκ3-20Jκ1 engineered light chain, 12 demonstrated >50% blocking, while 6 demonstrated <50% blocking (3 at 25-50% blocking and 3 at <25% blocking) of Ligand Y binding to Antigen E-labeled beads.

In the second Luminex™ experiment described above, the same 80 common light chain antibodies containing the Vκ1-39Jκ5 engineered light chain were tested for their ability to block binding of Antigen E to Ligand Y-labeled beads. Of these 80 common light chain antibodies, 36 demonstrated >50% blocking, while 44 demonstrated <50% blocking (27 at 25-50% blocking and 17 at <25% blocking). For the 18 common light chain antibodies containing the Vκ3-20Jκ1 engineered light chain, 1 demonstrated >50% blocking, while 17 demonstrated <50% blocking (5 at 25-50% blocking and 12 at <25% blocking) of Antigen E binding to Ligand Y-labeled beads.

The data of Tables 5 and 6 establish that the rearrangements described in Tables 3 and 4 generated anti-Antigen E-specific common light chain antibodies that blocked blocking of Ligand Y to its cognate receptor Antigen E with varying degrees of efficacy, which is consistent with the anti-Antigen E common light chain antibodies of Tables 3 and 4 comprising antibodies with overlapping and non-overlapping epitope specificity with respect to Antigen E.

TABLE 5

| Vκ1-39Jκ5 Common Light Chain Antibodies | | |
|---|---|---|
| Antibody | % Blocking of Antigen E-Labeled Beads | % Blocking of Antigen E In Solution |
| 2948 | 81.1 | 47.8 |
| 2948G | 38.6 | ND |
| 2949 | 97.6 | 78.8 |
| 2949G | 97.1 | 73.7 |
| 2950 | 96.2 | 81.9 |
| 2950G | 89.8 | 31.4 |
| 2952 | 96.1 | 74.3 |
| 2952G | 93.5 | 39.9 |
| 2954 | 93.7 | 70.1 |
| 2954G | 91.7 | 30.1 |
| 2955 | 75.8 | 30.0 |
| 2955G | 71.8 | ND |
| 2964 | 92.1 | 31.4 |
| 2964G | 94.6 | 43.0 |
| 2978 | 98.0 | 95.1 |
| 2978G | 13.9 | 94.1 |
| 2982 | 92.8 | 78.5 |
| 2982G | 41.9 | 52.4 |
| 2985 | 39.5 | 31.2 |
| 2985G | 2.0 | 5.0 |
| 2987 | 81.7 | 67.8 |
| 2987G | 26.6 | 29.3 |
| 2996 | 87.3 | 55.3 |
| 2996G | 95.9 | 38.4 |
| 2997 | 93.4 | 70.6 |
| 2997G | 9.7 | 7.5 |
| 3004 | 79.0 | 48.4 |
| 3004G | 60.3 | 40.7 |
| 3005 | 97.4 | 93.5 |
| 3005G | 77.5 | 75.6 |
| 3010 | 98.0 | 82.6 |
| 3010G | 97.9 | 81.0 |
| 3011 | 87.4 | 42.8 |
| 3011G | 83.5 | 41.7 |
| 3012 | 91.0 | 60.8 |
| 3012G | 52.4 | 16.8 |
| 3013 | 80.3 | 65.8 |
| 3013G | 17.5 | 15.4 |
| 3014 | 63.4 | 20.7 |
| 3014G | 74.4 | 28.5 |
| 3015 | 89.1 | 55.7 |
| 3015G | 58.8 | 17.3 |
| 3016 | 97.1 | 81.6 |
| 3016G | 93.1 | 66.4 |
| 3017 | 94.8 | 70.2 |
| 3017G | 87.9 | 40.8 |
| 3018 | 85.4 | 54.0 |
| 3018G | 26.1 | 12.7 |
| 3019 | 99.3 | 92.4 |
| 3019G | 99.3 | 88.1 |
| 3020 | 96.7 | 90.3 |
| 3020G | 85.2 | 41.5 |
| 3021 | 74.5 | 26.1 |
| 3021G | 81.1 | 27.4 |
| 3022 | 65.2 | 17.6 |
| 3022G | 67.2 | 9.1 |
| 3023 | 71.4 | 28.5 |
| 3023G | 73.8 | 29.7 |
| 3024 | 73.9 | 32.6 |
| 3024G | 89.0 | 10.0 |
| 3025 | 70.7 | 15.6 |
| 3025G | 76.7 | 24.3 |
| 3027 | 96.2 | 61.6 |
| 3027G | 98.6 | 75.3 |
| 3028 | 92.4 | 29.0 |

TABLE 5-continued

| Vκ1-39Jκ5 Common Light Chain Antibodies | | |
|---|---|---|
| Antibody | % Blocking of Antigen E-Labeled Beads | % Blocking of Antigen E In Solution |
| 3028G | 87.3 | 28.8 |
| 3030 | 6.0 | 10.6 |
| 3030G | 41.3 | 14.2 |
| 3032 | 76.5 | 31.4 |
| 3032G | 17.7 | 11.0 |
| 3033 | 98.2 | 86.1 |
| 3033G | 93.6 | 64.0 |
| 3036 | 74.7 | 32.7 |
| 3036G | 90.1 | 51.2 |
| 3041 | 95.3 | 75.9 |
| 3041G | 92.4 | 51.6 |
| 3042 | 88.1 | 73.3 |
| 3042G | 60.9 | 25.2 |
| 3043 | 90.8 | 65.8 |
| 3043G | 92.8 | 60.3 |

TABLE 6

| Vκ3-20Jκ1 Common Light Chain Antibodies | | |
|---|---|---|
| Antibody | % Blocking of Antigen E-Labeled Beads | % Blocking of Antigen E In Solution |
| 2968 | 97.1 | 73.3 |
| 2968G | 67.1 | 14.6 |
| 2969 | 51.7 | 20.3 |
| 2969G | 37.2 | 16.5 |
| 2970 | 92.2 | 34.2 |
| 2970G | 92.7 | 27.2 |
| 2971 | 23.4 | 11.6 |
| 2971G | 18.8 | 18.9 |
| 2972 | 67.1 | 38.8 |
| 2972G | 64.5 | 39.2 |
| 2973 | 77.7 | 27.0 |
| 2973G | 51.1 | 20.7 |
| 2974 | 57.8 | 12.4 |
| 2974G | 69.9 | 17.6 |
| 2975 | 49.4 | 18.2 |
| 2975G | 32.0 | 19.5 |
| 2976 | 1.0 | 1.0 |
| 2976G | 50.4 | 20.4 |

Example 8. Determination of Blocking Ability of Antigen-Specific Common Light Chain Antibodies by ELISA Human common light chain antibodies raised against Antigen E were tested for their ability to block Antigen E binding to a Ligand Y-coated surface in an ELISA assay.

Ligand Y was coated onto 96-well plates at a concentration of 2 μg/mL diluted in PBS and incubated overnight followed by washing four times in PBS with 0.05% Tween-20. The plate was then blocked with PBS (Irvine Scientific, Santa Ana, Calif.) containing 0.5% (w/v) BSA (Sigma-Aldrich Corp., St. Louis, Mo.) for one hour at room temperature. In a separate plate, supernatants containing anti-Antigen E common light chain antibodies were diluted 1:10 in buffer. A mock supernatant with the same components of the antibodies was used as a negative control. Antigen E-mmH (described above) was added to a final concentration of 0.150 nM and incubated for one hour at room temperature. The antibody/Antigen E-mmH mixture was then added to the plate containing Ligand Y and incubated for one hour at room temperature. Detection of Antigen E-mmH bound to Ligand Y was determined with Horse-Radish Peroxidase (HRP) conjugated to anti-Penta-His antibody (Qiagen, Valencia, Calif.) and developed by standard colorimetric response using tetramethylbenzidine (TMB) substrate (BD Biosciences, San Jose, Calif.) neutralized by sulfuric acid. Absorbance was read at OD450 for 0.1 sec. Background absorbance of a sample without Antigen E was subtracted from all samples. Percent blocking was calculated by division of the background-subtracted MFI of each sample by the adjusted negative control value, multiplying by 100 and subtracting the resulting value from 100.

Tables 7 and 8 show the percent blocking for all 98 anti-Antigen E common light chain antibodies tested in the ELISA assay. ND: not determined under current experimental conditions.

As described in this Example, of the 80 common light chain antibodies containing the Vκ1-39Jκ5 engineered light chain tested for their ability to block Antigen E binding to a Ligand Y-coated surface, 22 demonstrated >50% blocking, while 58 demonstrated <50% blocking (20 at 25-50% blocking and 38 at <25% blocking). For the 18 common light chain antibodies containing the Vκ3-20Jκ1 engineered light chain, 1 demonstrated >50% blocking, while 17 demonstrated <50% blocking (5 at 25-50% blocking and 12 at <25% blocking) of Antigen E binding to a Ligand Y-coated surface.

These results are also consistent with the Antigen E-specific common light chain antibody pool comprising antibodies with overlapping and non-overlapping epitope specificity with respect to Antigen E.

TABLE 7

| Vκ1-39Jκ5 Common Light Chain Antibodies | |
|---|---|
| Antibody | % Blocking of Antigen E In Solution |
| 2948 | 21.8 |
| 2948G | 22.9 |
| 2949 | 79.5 |
| 2949G | 71.5 |
| 2950 | 80.4 |
| 2950G | 30.9 |
| 2952 | 66.9 |
| 2952G | 47.3 |
| 2954 | 55.9 |
| 2954G | 44.7 |
| 2955 | 12.1 |
| 2955G | 25.6 |
| 2964 | 34.8 |
| 2964G | 47.7 |
| 2978 | 90.0 |
| 2978G | 90.2 |
| 2982 | 59.0 |
| 2982G | 20.4 |
| 2985 | 10.5 |
| 2985G | ND |
| 2987 | 31.4 |
| 2987G | ND |
| 2996 | 29.3 |
| 2996G | ND |
| 2997 | 48.7 |
| 2997G | ND |
| 3004 | 16.7 |
| 3004G | 3.5 |
| 3005 | 87.2 |
| 3005G | 54.3 |
| 3010 | 74.5 |
| 3010G | 84.6 |
| 3011 | 19.4 |
| 3011G | ND |
| 3012 | 45.0 |

TABLE 7-continued

| Vκ1-39Jκ5 Common Light Chain Antibodies | |
|---|---|
| Antibody | % Blocking of Antigen E In Solution |
| 3012G | 12.6 |
| 3013 | 39.0 |
| 3013G | 9.6 |
| 3014 | 5.2 |
| 3014G | 17.1 |
| 3015 | 23.7 |
| 3015G | 10.2 |
| 3016 | 78.1 |
| 3016G | 37.4 |
| 3017 | 61.6 |
| 3017G | 25.2 |
| 3018 | 40.6 |
| 3018G | 14.5 |
| 3019 | 94.6 |
| 3019G | 92.3 |
| 3020 | 80.8 |
| 3020G | ND |
| 3021 | 7.6 |
| 3021G | 20.7 |
| 3022 | 2.4 |
| 3022G | 15.0 |
| 3023 | 9.1 |
| 3023G | 19.2 |
| 3024 | 7.5 |
| 3024G | 15.2 |
| 3025 | ND |
| 3025G | 13.9 |
| 3027 | 61.4 |
| 3027G | 82.7 |
| 3028 | 40.3 |
| 3028G | 12.3 |
| 3030 | ND |
| 3030G | 9.5 |
| 3032 | ND |
| 3032G | 13.1 |
| 3033 | 77.1 |
| 3033G | 32.9 |
| 3036 | 17.6 |
| 3036G | 24.6 |
| 3041 | 59.3 |
| 3041G | 30.7 |
| 3042 | 39.9 |
| 3042G | 16.1 |
| 3043 | 57.4 |
| 3043G | 46.1 |

TABLE 8

| Vκ3-20Jκ1 Common Light Chain Antibodies | |
|---|---|
| Antibody | % Blocking of Antigen E In Solution |
| 2968 | 68.9 |
| 2968G | 15.2 |
| 2969 | 10.1 |
| 2969G | 23.6 |
| 2970 | 34.3 |
| 2970G | 41.3 |
| 2971 | 6.3 |
| 2971G | 27.1 |
| 2972 | 9.6 |
| 2972G | 35.7 |
| 2973 | 20.7 |
| 2973G | 23.1 |
| 2974 | ND |
| 2974G | 22.0 |
| 2975 | 8.7 |
| 2975G | 19.2 |

TABLE 8-continued

Vκ3-20Jκ1
Common Light Chain Antibodies

| Antibody | % Blocking of Antigen E In Solution |
|---|---|
| 2976 | 4.6 |
| 2976G | 26.7 |

Example 9. BIAcore™ Affinity Determination for Antigen-Specific Common Light Chain Antibodies Equilibrium dissociation constants ($K_D$) for selected antibody supernatants were determined by SPR (Surface Plasmon Resonance) using a BIAcore™ T100 instrument (GE Healthcare). All data was obtained using HBS-EP (10 mM Hepes, 150 mM NaCl, 0.3 mM EDTA, 0.05% Surfactant P20, pH 7.4) as both the running and sample buffers, at 25° C. Antibodies were captured from crude supernatant samples on a CM5 sensor chip surface previously derivatized with a high density of anti-human Fc antibodies using standard amine coupling chemistry. During the capture step, supernatants were injected across the anti-human Fc surface at a flow rate of 3 μL/min, for a total of 3 minutes. The capture step was followed by an injection of either running buffer or analyte at a concentration of 100 nM for 2 minutes at a flow rate of 35 μL/min. Dissociation of antigen from the captured antibody was monitored for 6 minutes. The captured antibody was removed by a brief injection of 10 mM glycine, pH 1.5. All sensorgrams were double referenced by subtracting sensorgrams from buffer injections from the analyte sensorgrams, thereby removing artifacts caused by dissociation of the antibody from the capture surface. Binding data for each antibody was fit to a 1:1 binding model with mass transport using BIAcore T100 Evaluation software v2.1. Results are shown in Tables 9 and 10.

The binding affinities of common light chain antibodies comprising the rearrangements shown in Tables 3 and 4 vary, with nearly all exhibiting a $K_D$ in the nanomolar range. The affinity data is consistent with the common light chain antibodies resulting from the combinatorial association of rearranged variable domains described in Tables 3 and 4 being high-affinity, clonally selected, and somatically mutated. Coupled with data previously shown, the common light chain antibodies described in Tables 3 and 4 comprise a collection of diverse, high-affinity antibodies that exhibit specificity for one or more epitopes on Antigen E.

TABLE 9

Vκ1-39Jκ5
Common Light Chain Antibodies

| Antibody | 100 nM Antigen E | |
|---|---|---|
|  | $K_D$ (nM) | $T_{1/2}$ (min) |
| 2948 | 8.83 | 28 |
| 2948G | 95.0 | 1 |
| 2949 | 3.57 | 18 |
| 2949G | 6.37 | 9 |
| 2950 | 4.91 | 17 |
| 2950G | 13.6 | 5 |
| 2952 | 6.25 | 7 |
| 2952G | 7.16 | 4 |
| 2954 | 2.37 | 24 |
| 2954G | 5.30 | 9 |
| 2955 | 14.4 | 6 |
| 2955G | 12.0 | 4 |
| 2964 | 14.8 | 6 |
| 2964G | 13.0 | 9 |
| 2978 | 1.91 | 49 |
| 2978G | 1.80 | 58 |
| 2982 | 6.41 | 19 |
| 2982G | 16.3 | 9 |
| 2985 | 64.4 | 9 |
| 2985G | 2.44 | 8 |
| 2987 | 21.0 | 11 |
| 2987G | 37.6 | 4 |
| 2996 | 10.8 | 9 |
| 2996G | 24.0 | 2 |
| 2997 | 7.75 | 19 |
| 2997G | 151 | 1 |
| 3004 | 46.5 | 14 |
| 3004G | 1.93 | 91 |
| 3005 | 2.35 | 108 |
| 3005G | 6.96 | 27 |
| 3010 | 4.13 | 26 |
| 3010G | 2.10 | 49 |
| 3011 | 59.1 | 5 |
| 3011G | 41.7 | 5 |
| 3012 | 9.71 | 20 |
| 3012G | 89.9 | 2 |
| 3013 | 20.2 | 20 |
| 3013G | 13.2 | 4 |
| 3014 | 213 | 4 |
| 3014G | 36.8 | 3 |
| 3015 | 29.1 | 11 |
| 3015G | 65.9 | 0 |
| 3016 | 4.99 | 17 |
| 3016G | 18.9 | 4 |
| 3017 | 9.83 | 8 |
| 3017G | 55.4 | 2 |
| 3018 | 11.3 | 36 |
| 3018G | 32.5 | 3 |
| 3019 | 1.54 | 59 |
| 3019G | 2.29 | 42 |
| 3020 | 5.41 | 39 |
| 3020G | 41.9 | 6 |
| 3021 | 50.1 | 6 |
| 3021G | 26.8 | 4 |
| 3022 | 25.7 | 17 |
| 3022G | 20.8 | 12 |
| 3023 | 263 | 9 |
| 3023G | 103 | 5 |
| 3024 | 58.8 | 7 |
| 3024G | 7.09 | 10 |
| 3025 | 35.2 | 6 |
| 3025G | 42.5 | 8 |
| 3027 | 7.15 | 6 |
| 3027G | 4.24 | 18 |
| 3028 | 6.89 | 37 |
| 3028G | 7.23 | 22 |
| 3030 | 46.2 | 7 |
| 3030G | 128 | 3 |
| 3032 | 53.2 | 9 |
| 3032G | 13.0 | 1 |
| 3033 | 4.61 | 17 |
| 3033G | 12.0 | 5 |
| 3036 | 284 | 12 |
| 3036G | 18.2 | 10 |
| 3041 | 6.90 | 12 |
| 3041G | 22.9 | 2 |
| 3042 | 9.46 | 34 |
| 3042G | 85.5 | 3 |
| 3043 | 9.26 | 29 |
| 3043G | 13.1 | 22 |

TABLE 10

Vκ3-20Jκ1 Common Light Chain Antibodies

| Antibody | 100 nM Antigen E | |
|---|---|---|
| | $K_D$ (nM) | $T_{1/2}$ (min) |
| 2968 | 5.50 | 8 |
| 2968G | 305 | 0 |
| 2969 | 34.9 | 2 |
| 2969G | 181 | 1 |
| 2970G | 12.3 | 3 |
| 2971G | 32.8 | 22 |
| 2972 | 6.02 | 13 |
| 2972G | 74.6 | 26 |
| 2973 | 5.35 | 39 |
| 2973G | 11.0 | 44 |
| 2974 | 256 | 0 |
| 2974G | 138 | 0 |
| 2975 | 38.0 | 2 |
| 2975G | 134 | 1 |
| 2976 | 6.73 | 10 |
| 2976G | 656 | 8 |

Example 10. Determination of Binding Specificities of Antigen-Specific Common Light Chain Antibodies by Luminex™ Assay Selected anti-Antigen E common light chain antibodies were tested for their ability to bind to the ECD of Antigen E and Antigen E ECD variants, including the cynomolgus monkey ortholog (Mf Antigen E), which differs from the human protein in approximately 10% of its amino acid residues; a deletion mutant of Antigen E lacking the last 10 amino acids from the C-terminal end of the ECD (Antigen E-ΔCT); and two mutants containing an alanine substitution at suspected locations of interaction with Ligand Y (Antigen E-Ala1 and AntigenE-Ala2). The Antigen E proteins were produced in CHO cells and each contained a myc-myc-His C-terminal tag.

For the binding studies, Antigen E ECD protein or variant protein (described above) from 1 mL of culture medium was captured by incubation for 2 hr at room temperature with $1 \times 10^6$ microsphere (Luminex™) beads covalently coated with an anti-myc monoclonal antibody (MAb 9E10, hybridoma cell line CRL-1729™; ATCC, Manassas, Va.). The beads were then washed with PBS before use. Supernatants containing anti-Antigen E common light chain antibodies were diluted 1:4 in buffer and added to 96-well filter plates. A mock supernatant with no antibody was used as negative control. The beads containing the captured Antigen E proteins were then added to the antibody samples (3000 beads per well) and incubated overnight at 4° C. The following day, the sample beads were washed and the bound common light chain antibody was detected with a R-phycoerythrin-conjugated anti-human IgG antibody. The fluorescence intensity of the beads (approximately 100 beads counted for each antibody sample binding to each Antigen E protein) was measured with a Luminex™ flow cytometry-based analyzer, and the median fluorescence intensity (MFI) for at least 100 counted beads per bead/antibody interaction was recorded. Results are shown in Tables 11 and 12.

TABLE 11

Vκ1-39Jκ5 Common Light Chain Antibodies

| | Mean Fluorescence Intensity (MFI) | | | | |
|---|---|---|---|---|---|
| Antibody | Antigen E-ECD | Antigen E-ΔCT | Antigen E-Ala1 | Antigen E-Ala2 | Mf Antigen E |
| 2948 | 1503 | 2746 | 4953 | 3579 | 1648 |
| 2948G | 537 | 662 | 2581 | 2150 | 863 |
| 2949 | 3706 | 4345 | 8169 | 5678 | 5142 |
| 2949G | 3403 | 3318 | 7918 | 5826 | 5514 |
| 2950 | 3296 | 4292 | 7756 | 5171 | 4749 |
| 2950G | 2521 | 2408 | 7532 | 5079 | 3455 |
| 2952 | 3384 | 1619 | 1269 | 168 | 911 |
| 2952G | 3358 | 1001 | 108 | 55 | 244 |
| 2954 | 2808 | 3815 | 7114 | 5039 | 3396 |
| 2954G | 2643 | 2711 | 7620 | 5406 | 3499 |
| 2955 | 1310 | 2472 | 4738 | 3765 | 1637 |
| 2955G | 1324 | 1802 | 4910 | 3755 | 1623 |
| 2964 | 5108 | 1125 | 4185 | 346 | 44 |
| 2964G | 4999 | 729 | 4646 | 534 | 91 |
| 2978 | 6986 | 2800 | 14542 | 10674 | 8049 |
| 2978G | 5464 | 3295 | 11652 | 8026 | 6452 |
| 2982 | 4955 | 2388 | 13200 | 9490 | 6772 |
| 2982G | 3222 | 2013 | 8672 | 6509 | 4949 |
| 2985 | 1358 | 832 | 4986 | 3892 | 1669 |
| 2985G | 43 | 43 | 128 | 244 | 116 |
| 2987 | 3117 | 1674 | 7646 | 5944 | 2546 |
| 2987G | 3068 | 1537 | 9202 | 6004 | 4744 |
| 2996 | 4666 | 1917 | 12875 | 9046 | 6459 |
| 2996G | 2752 | 1736 | 8742 | 6150 | 4873 |
| 2997 | 5164 | 2159 | 12167 | 8361 | 5922 |
| 2997G | 658 | 356 | 3392 | 2325 | 1020 |
| 3004 | 2794 | 1397 | 8542 | 6268 | 3083 |
| 3004G | 2753 | 1508 | 8267 | 5808 | 4345 |
| 3005 | 5683 | 2221 | 12900 | 9864 | 5868 |
| 3005G | 4344 | 2732 | 10669 | 7125 | 5880 |
| 3010 | 4829 | 1617 | 2642 | 3887 | 44 |
| 3010G | 3685 | 1097 | 2540 | 3022 | 51 |
| 3011 | 2859 | 2015 | 7855 | 5513 | 3863 |
| 3011G | 2005 | 1072 | 6194 | 4041 | 3181 |
| 3012 | 3233 | 2221 | 8543 | 5637 | 3307 |
| 3012G | 968 | 378 | 3115 | 2261 | 1198 |
| 3013 | 2343 | 1791 | 6715 | 4810 | 2528 |
| 3013G | 327 | 144 | 1333 | 1225 | 370 |
| 3014 | 1225 | 1089 | 5436 | 3621 | 1718 |
| 3014G | 1585 | 851 | 5178 | 3705 | 2411 |
| 3015 | 3202 | 2068 | 8262 | 5554 | 3796 |
| 3015G | 1243 | 531 | 4246 | 2643 | 1611 |
| 3016 | 4220 | 2543 | 8920 | 5999 | 5666 |
| 3016G | 2519 | 1277 | 6344 | 4288 | 4091 |
| 3017 | 3545 | 2553 | 8700 | 5547 | 5098 |
| 3017G | 1972 | 1081 | 5763 | 3825 | 3038 |
| 3018 | 2339 | 1971 | 6140 | 4515 | 2293 |
| 3018G | 254 | 118 | 978 | 1020 | 345 |
| 3019 | 5235 | 1882 | 7108 | 4249 | 54 |
| 3019G | 4090 | 1270 | 4769 | 3474 | 214 |
| 3020 | 3883 | 3107 | 8591 | 6602 | 4420 |
| 3020G | 2165 | 1209 | 6489 | 4295 | 2912 |
| 3021 | 1961 | 1472 | 6872 | 4641 | 2742 |
| 3021G | 2091 | 1005 | 6430 | 3988 | 2935 |
| 3022 | 2418 | 793 | 7523 | 2679 | 36 |
| 3022G | 2189 | 831 | 6182 | 3051 | 132 |
| 3023 | 1692 | 1411 | 5788 | 3898 | 2054 |
| 3023G | 1770 | 825 | 5702 | 3677 | 2648 |
| 3024 | 1819 | 1467 | 6179 | 4557 | 2450 |
| 3024G | 100 | 87 | 268 | 433 | 131 |
| 3025 | 1853 | 1233 | 6413 | 4337 | 2581 |
| 3025G | 1782 | 791 | 5773 | 3871 | 2717 |
| 3027 | 4131 | 1018 | 582 | 2510 | 22 |
| 3027G | 3492 | 814 | 1933 | 2596 | 42 |
| 3028 | 4361 | 2545 | 9884 | 5639 | 975 |
| 3028G | 2835 | 1398 | 7124 | 3885 | 597 |
| 3030 | 463 | 277 | 1266 | 1130 | 391 |
| 3030G | 943 | 302 | 3420 | 2570 | 1186 |
| 3032 | 2083 | 1496 | 6594 | 4402 | 2405 |
| 3032G | 295 | 106 | 814 | 902 | 292 |
| 3033 | 4409 | 2774 | 8971 | 6331 | 5825 |
| 3033G | 2499 | 1234 | 6745 | 4174 | 4210 |
| 3036 | 1755 | 1362 | 6137 | 4041 | 1987 |

TABLE 11-continued

Vκ1-39Jκ5 Common Light Chain Antibodies

| | Mean Fluorescence Intensity (MFI) | | | | |
|---|---|---|---|---|---|
| Antibody | Antigen E-ECD | Antigen E-ΔCT | Antigen E-Ala1 | Antigen E-Ala2 | Mf Antigen E |
| 3036G | 2313 | 1073 | 6387 | 4243 | 3173 |
| 3041 | 3674 | 2655 | 8629 | 5837 | 4082 |
| 3041G | 2519 | 1265 | 6468 | 4274 | 3320 |
| 3042 | 2653 | 2137 | 7277 | 5124 | 3325 |
| 3042G | 1117 | 463 | 4205 | 2762 | 1519 |
| 3043 | 3036 | 2128 | 7607 | 5532 | 3366 |
| 3043G | 2293 | 1319 | 6573 | 4403 | 3228 |

TABLE 12

Vκ3-20Jκ1 Common Light Chain Antibodies

| | Mean Fluorescence Intensity (MFI) | | | | |
|---|---|---|---|---|---|
| Antibody | Antigen E-ECD | Antigen E-ΔCT | Antigen E-Ala1 | Antigen E-Ala2 | Mf Antigen E |
| 2968 | 6559 | 3454 | 14662 | 3388 | 29 |
| 2968G | 2149 | 375 | 9109 | 129 | 22 |
| 2969 | 2014 | 1857 | 7509 | 5671 | 3021 |
| 2969G | 1347 | 610 | 6133 | 4942 | 2513 |
| 2970 | 5518 | 1324 | 14214 | 607 | 32 |
| 2970G | 4683 | 599 | 12321 | 506 | 31 |
| 2971 | 501 | 490 | 2506 | 2017 | 754 |
| 2971G | 578 | 265 | 2457 | 2062 | 724 |
| 2972 | 2164 | 2158 | 8408 | 6409 | 3166 |
| 2972G | 1730 | 992 | 6364 | 4602 | 2146 |
| 2973 | 3527 | 1148 | 3967 | 44 | 84 |
| 2973G | 1294 | 276 | 1603 | 28 | 44 |
| 2974 | 1766 | 722 | 8821 | 241 | 19 |
| 2974G | 2036 | 228 | 8172 | 135 | 26 |
| 2975 | 1990 | 1476 | 8669 | 6134 | 2468 |
| 2975G | 890 | 315 | 4194 | 3987 | 1376 |
| 2976 | 147 | 140 | 996 | 1079 | 181 |
| 2976G | 1365 | 460 | 6024 | 3929 | 1625 |

The anti-Antigen E common light chain antibody supernatants exhibited high specific binding to the beads linked to Antigen E-ECD. For these beads, the negative control mock supernatant resulted in negligible signal (<10 MFI) when combined with the Antigen E-ECD bead sample, whereas the supernatants containing anti-Antigen E common light chain antibodies exhibited strong binding signal (average MFI of 2627 for 98 antibody supernatants; MFI>500 for 91/98 antibody samples).

As a measure of the ability of the selected anti-Antigen E common light chain antibodies to identify different epitopes on the ECD of Antigen E, the relative binding of the antibodies to the variants were determined. All four Antigen E variants were captured to the anti-myc Luminex™ beads as described above for the native Antigen E-ECD binding studies, and the relative binding ratios ($MFI_{variant}/MFI_{Antigen\ E\text{-}ECD}$) were determined. For 98 tested common light chain antibody supernatants shown in Tables 11 and 12, the average ratios ($MFI_{variant}/MFI_{Antigen\ E\text{-}ECD}$) differed for each variant, likely reflecting different capture amounts of proteins on the beads (average ratios of 0.61, 2.9, 2.0, and 1.0 for Antigen E-ΔCT, Antigen E-Ala1, Antigen E-Ala2, and Mf Antigen E, respectively). For each protein variant, the binding for a subset of the 98 tested common light chain antibodies showed greatly reduced binding, indicating sensitivity to the mutation that characterized a given variant. For example, 19 of the common light chain antibody samples bound to the Mf Antigen E with $MFI_{variant}/MFI_{Antigen\ E\text{-}ECD}$ of <8%. Since many in this group include high or moderately high affinity antibodies (5 with $K_D<5$ nM, 15 with $K_D<50$ nM), it is likely that the lower signal for this group results from sensitivity to the sequence (epitope) differences between native Antigen E-ECD and a given variant rather than from lower affinities.

These data establish that the common light chain antibodies described in Tables 3 and 4 indeed represent a diverse group of Antigen-E-specific common light chain antibodies that specifically recognize more than one epitope on Antigen E.

What is claimed is:

1. A mouse that is heterozygous or homozygous in its germline for:
   (a) an insertion at an endogenous mouse κ immunoglobulin light chain variable region locus, wherein the insertion includes a rearranged Vκ/Jκ sequence encoding a κ immunoglobulin light chain variable domain, wherein the rearranged Vκ/Jκ sequence consists of:
      a human Vκ1-39 gene segment joined to a human Jκ5 gene segment as set forth in nucleotides 2362 through 2686 of SEQ ID NO: 1, or
      a human Vκ3-20 gene segment joined to a human Jκ1 gene segment as set forth in nucleotides 2373 through 2697 of SEQ ID NO: 11;
   wherein the rearranged Vκ/Jκ sequence is operably linked to the endogenous mouse κ constant region; and
   (b) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

2. The mouse of claim 1, wherein the mouse lacks an endogenous mouse κ immunoglobulin light chain variable region locus that is capable of rearranging and forming a mouse κ variable region sequence that encodes a mouse κ variable domain.

3. The mouse of claim 1, further comprising a mouse κ intronic enhancer upstream of the endogenous mouse κ constant region.

4. The mouse of claim 1, further comprising a mouse κ 3' enhancer downstream of the endogenous mouse κ constant region.

5. The mouse of claim 1, wherein the plurality of human immunoglobulin heavy chain variable region gene segments comprises at least one gene segment selected from the group consisting of $V_H1-2$, $V_H1-8$, $V_H1-24$, $V_H2-5$, $V_H3-7$, $V_H3-9$, $V_H3-11$, $V_H3-13$, $V_H3-15$, $V_H3-20$, $V_H3-23$, $V_H3-30$, $V_H3-33$, $V_H3-43$, $V_H3-48$, $V_H4-31$, $V_H4-39$, $V_H4-59$, $V_H5-51$ and $V_H6-1$.

6. The mouse of claim 1, wherein the mouse comprises a population of B cells that together express a plurality of immunoglobulin heavy chains comprising human heavy chain variable domains expressed from rearranged human heavy chain variable region sequences comprising a $V_H1-2$, $V_H1-8$, $V_H1-24$, $V_H2-5$, $V_H3-7$, $V_H3-9$, $V_H3-11$, $V_H3-13$, $V_H3-15$, $V_H3-20$, $V_H3-23$, $V_H3-30$, $V_H3-33$, $V_H3-43$, $V_H3-48$, $V_H4-31$, $V_H4-39$, $V_H4-59$, $V_H5-51$, $V_H6-1$, or a somatically hypermutated variant thereof.

7. A method for selecting a human immunoglobulin heavy chain variable region sequence for making an antibody, comprising:
   (a) immunizing a genetically modified mouse with an antigen of interest, wherein the mouse is heterozygous or homozygous in its germline for:
      (i) an insertion at an endogenous mouse κ immunoglobulin light chain variable region locus, wherein the insertion includes a rearranged Vκ/Jκ sequence encoding a κ immunoglobulin light chain variable domain, wherein the rearranged Vκ/Jκ sequence consists of:
         a human Vκ1-39 gene segment joined to a human Jκ5 gene segment as set forth in nucleotides 2362 through 2686 of SEQ ID NO: 1, or
         a human Vκ3-20 gene segment joined to a human Jκ1 gene segment as set forth in nucleotides 2373 through 2697 of SEQ ID NO: 11;
      wherein the rearranged human Vκ/Jκ sequence is operably linked to the endogenous mouse κ constant region; and
      (ii) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region segments are capable of rearranging and forming a rearranged human/mouse chimeric immunoglobulin heavy chain gene;
(b) allowing the mouse to develop an immune response to the antigen of interest; and
(c) identifying a lymphocyte of the mouse that expresses an antibody that specifically binds the antigen of interest, and obtaining a human immunoglobulin heavy chain variable region sequence that encodes a human immunoglobulin heavy chain variable domain of said antibody.

8. The method of claim 7, wherein the mouse lacks an endogenous mouse κ immunoglobulin light chain variable region locus that is capable of rearranging and forming a mouse κ variable region sequence that encodes a mouse κ variable domain.

9. The method of claim 7, wherein the mouse further comprises a mouse κ intronic enhancer upstream of the endogenous mouse κ constant region.

10. The method of claim 7, wherein the mouse further comprises a mouse κ 3' enhancer downstream of the endogenous mouse κ constant region.

11. The method of claim 7, wherein the plurality of human immunoglobulin heavy chain variable region gene segments comprises at least one gene segment selected from the group consisting of VH1-2, VH1-8, VH1-24, VH2-5, VH3-7, VH3-9, VH3-11, VH3-13, VH3-15, VH3-20, VH3-23, VH3-30, VH3-33, VH3-43, VH3-48, VH4-31, VH4-39, VH4-59, VH5-51 and VH6-1.

12. The method of claim 7, wherein the mouse comprises a population of B cells that together express a plurality of immunoglobulin heavy chains comprising human heavy chain variable domains expressed from rearranged human heavy chain variable region sequences comprising a $V_H$1-2, $V_H$1-8, $V_H$1-24, $V_H$2-5, $V_H$3-7, $V_H$3-9, $V_H$3-11, $V_H$3-13, $V_H$3-15, $V_H$3-20, $V_H$3-23, $V_H$3-30, $V_H$3-33, $V_H$3-43, $V_H$3-48, $V_H$4-31, $V_H$4-39, $V_H$4-59, $V_H$5-51, $V_H$6-1, or a somatically hypermutated variant thereof.

13. The method of claim 7, wherein steps (a) through (c) are performed a first time for a first antigen of interest to generate a first human immunoglobulin heavy chain variable region sequence, and steps (a) through (c) are performed a second time for a second antigen of interest to generate a second human immunoglobulin heavy chain variable region sequence, and wherein the first human immunoglobulin heavy chain variable region sequence is expressed fused with a first human immunoglobulin heavy chain constant region to form a first human immunoglobulin heavy chain gene that encodes a first human immunoglobulin heavy chain, the second human immunoglobulin heavy chain variable region sequence is expressed fused with a second human immunoglobulin heavy chain constant region to form a second human immunoglobulin heavy chain gene that encodes a second human immunoglobulin heavy chain, and the first and the second human immunoglobulin heavy chains are expressed in the presence of a single human immunoglobulin light chain derived from the same rearranged Vκ/Jκ sequence as present in the mouse to generate a bispecific antibody.

14. A method of using a genetically modified mouse in making a human common light chain antibody, the mouse being genetically modified in that its germline:
(a) is homozygous or heterozygous for an insertion at an endogenous mouse κ immunoglobulin light chain variable region locus, wherein the insertion includes a rearranged Vκ/Jκ sequence encoding a κ immunoglobulin light chain variable domain, wherein the rearranged Vκ/Jκ sequence consists of:
a human Vκ1-39 gene segment joined to a human Jκ5 gene segment as set forth in nucleotides 2362 through 2686 of SEQ ID NO: 1, or
a human Vκ3-20 gene segment joined to a human Jκ1 gene segment as set forth in nucleotides 2373 through 2697 of SEQ ID NO: 11;
wherein the rearranged Vκ/Jκ sequence is operably linked to the endogenous mouse κ constant region; and
(b) is homozygous or heterozygous for an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene;
the method comprising steps of:
identifying one or more human immunoglobulin heavy chain variable region sequence(s) from one or more B cells of the mouse, and expressing one or more human heavy chain(s) comprising the identified human immunoglobulin heavy chain variable region sequence(s) in a mammalian cell that also expresses a human immunoglobulin light chain, which human immunoglobulin heavy chain(s) pair with the human immunoglobulin light chain to form the human common light chain antibody.

15. The method of claim 14, wherein the mouse lacks an endogenous mouse κ immunoglobulin light chain variable region locus that is capable of rearranging and forming a mouse κ variable region that encodes a mouse κ variable domain.

16. The method of claim 14, wherein the mouse further comprises a mouse κ intronic enhancer upstream of the endogenous mouse κ constant region.

17. The method of claim 14, wherein the mouse further comprises a mouse κ 3' enhancer downstream of the endogenous mouse κ constant region.

18. The method of claim 14, wherein the plurality of human immunoglobulin heavy chain variable region gene segments comprises at least one gene segment selected from the group consisting of VH1-2, VH1-8, VH1-24, VH2-5, VH3-7, VH3-9, VH3-11, VH3-13, VH3-15, VH3-20, VH3-23, VH3-30, VH3-33, VH3-43, VH3-48, VH4-31, VH4-39, VH4-59, VH5-51 and VH6-1.

19. The method of claim 14, wherein the mouse comprises a population of B cells that together express a plurality of immunoglobulin heavy chains comprising human heavy chain variable domains expressed from rearranged human heavy chain variable region sequences comprising a VH1-2, VH1-8, VH1-24, VH2-5, VH3-7, VH3-9, VH3-11, VH3-13, VH3-15, VH3-20, VH3-23, VH3-30, VH3-33, VH3-43, VH3-48, VH4-31, VH4-39, VH4-59, VH5-51, VH6-1, or a somatically hypermutated variant thereof.

20. The mouse of claim 1, wherein
the insertion at the endogenous mouse κ immunoglobulin light chain variable region locus comprises replacement of endogenous mouse immunoglobulin κ light chain variable region gene segments with the rearranged Vκ/Jκ sequence; and/or the insertion at the endogenous mouse immunoglobulin heavy chain variable region locus comprises replacement of endogenous mouse immunoglobulin heavy chain variable region gene segments with the plurality of human immunoglobulin heavy chain variable region gene segments.

21. The method of claim 7, wherein
the insertion at the endogenous mouse κ immunoglobulin light chain variable region locus comprises replacement of endogenous mouse immunoglobulin κ light chain variable region gene segments with the rearranged Vκ/Jκ sequence; and/or
the insertion at the endogenous mouse immunoglobulin heavy chain variable region locus comprises replacement of endogenous mouse immunoglobulin heavy chain variable region gene segments with the plurality of human immunoglobulin heavy chain variable region gene segments.

22. A method of making a mouse that expresses a population of antigen-specific antibodies in response to challenge with an antigen, the method comprising steps of genetically engineering germline cells in the mouse so that, the genome of the germline cells is homozygous or heterozygous for:
(a) an insertion at an endogenous mouse κ immunoglobulin light chain variable region locus, wherein the insertion includes at least one mouse immunoglobulin light chain constant region gene operably linked to only a single immunoglobulin light chain variable region sequence, which single immunoglobulin light chain variable region sequence is a rearranged Vκ/Jκ sequence encoding a κ immunoglobulin light chain variable domain, wherein the rearranged Vκ/Jκ sequence consists of:
a human Vκ1-39 gene segment joined to a human Jκ5 gene segment as set forth in nucleotides 2362 through 2686 of SEQ ID NO: 1, or
a human Vκ3-20 gene segment joined to a human Jκ1 gene segment as set forth in nucleotides 2373 through 2697 of SEQ ID NO: 11; and
(b) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region gene and the human immunoglobulin heavy chain variable region gene segments are capable of rearranging and forming a rearranged human/mouse chimeric immunoglobulin heavy chain gene.

23. The mouse of claim 1, wherein the insertion at an endogenous mouse κ immunoglobulin light chain variable region locus of (a) further includes a human promoter and a mouse leader sequence.

24. The method of claim 7, wherein the insertion at an endogenous mouse κ immunoglobulin light chain variable region locus of (i) further includes a human promoter and a mouse leader sequence.

25. The method of claim 14, wherein the insertion at an endogenous mouse κ immunoglobulin light chain variable region locus of (a) further includes a human promoter and a mouse leader sequence.

26. The mouse of claim 1, wherein the insertion includes in 5' to 3' order: a promoter, a leader sequence, the rearranged Vκ/Jκ sequence, and a human Jκ-Cκ intron sequence.

27. The method of claim 7, wherein the insertion includes in 5' to 3' order: a promoter, a leader sequence, the rearranged Vκ/Jκ sequence, and a human Jκ-Cκ intron sequence.

28. The method of claim 14, wherein the insertion includes in 5' to 3' order: a promoter, a leader sequence, the rearranged Vκ/Jκ sequence, and a human Jκ-Cκ intron sequence.

* * * * *